US012806352B2

(12) United States Patent
Kenyon et al.

(10) Patent No.: US 12,806,352 B2
(45) Date of Patent: Nov. 24, 2026

(54) PNEUMATIC BLOCK FOR RESPIRATORY PRESSURE THERAPY DEVICE

(71) Applicant: ResMed Pty Ltd, Bella Vista (AU)

(72) Inventors: Barton John Kenyon, Sydney (AU); Michael James Dent, Sydney (AU); Emily Claire Shrubb, Sydney (AU); Melanie Lucia Cariola, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 759 days.

(21) Appl. No.: 18/207,841

(22) Filed: Jun. 9, 2023

(65) Prior Publication Data

US 2023/0310774 A1 Oct. 5, 2023

Related U.S. Application Data

(63) Continuation of application No. 16/711,999, filed on Dec. 12, 2019, now Pat. No. 11,712,529.

(Continued)

(51) Int. Cl.
*A61M 16/00* (2006.01)

(52) U.S. Cl.
CPC . *A61M 16/0069* (2014.02); *A61M 2016/0027* (2013.01); *A61M 2016/0039* (2013.01);
(Continued)

(58) Field of Classification Search
CPC .......... A61M 16/0066; A61M 16/0069; A61M 16/1095; A61M 16/0057
See application file for complete search history.

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

AU 2005271658 B9 6/2011
AU 2006294953 B2 4/2012
(Continued)

OTHER PUBLICATIONS

Notification of the First Office Action mailed Feb. 7, 2024 in Chinse Application No. 201980082926.0, with English translation, 13 pages.

(Continued)

*Primary Examiner* — Margaret M Luarca
(74) *Attorney, Agent, or Firm* — Nixon & Vanderhye P.C.

(57) ABSTRACT

Apparatus for providing air at positive pressure for respiratory therapy to a patient includes a pneumatic block including at least first and second blower sub-assemblies and a common chassis assembly configured to support each of the at least first and second blower sub-assemblies. The at least first and second blower sub-assemblies are different structurally from one another in at least one aspect. Each of the at least first and second blower sub-assemblies includes a corresponding blower configured to produce a flow of air at a therapeutic pressure. The common chassis assembly and the first blower sub-assembly form a first configuration of the pneumatic block, and the common chassis assembly and the second blower sub-assembly form a second configuration of the pneumatic block. The air flow path and the chamber arrangement of the first configuration is different than the air flow path and the chamber arrangement of the second configuration.

15 Claims, 69 Drawing Sheets

Related U.S. Application Data

(60) Provisional application No. 62/779,135, filed on Dec. 13, 2018.

(52) U.S. Cl.
CPC ............... *A61M 2016/0042* (2013.01); *A61M 2210/0618* (2013.01); *A61M 2210/0625* (2013.01)

(56) References Cited

U.S. PATENT DOCUMENTS

| | | | |
|---|---|---|---|
| 5,577,497 | A | 11/1996 | Mecikalski et al. |
| 6,532,959 | B1 | 3/2003 | Berthon-Jones |
| 6,581,594 | B1 | 6/2003 | Drew et al. |
| 6,837,260 | B1 | 1/2005 | Kuehn |
| 7,032,589 | B2 | 4/2006 | Kerechanin, II et al. |
| 7,096,864 | B1 | 8/2006 | Mayer et al. |
| 7,527,053 | B2 | 5/2009 | DeVries et al. |
| 7,677,246 | B2 | 3/2010 | Kepler et al. |
| 7,789,194 | B2 | 9/2010 | Lathrop et al. |
| 7,866,944 | B2 | 1/2011 | Kenyon et al. |
| 7,909,032 | B2 | 3/2011 | Feldhahn et al. |
| 8,375,945 | B2 | 2/2013 | Kepler et al. |
| 8,427,020 | B2 | 4/2013 | Hoffman et al. |
| 8,453,640 | B2 | 6/2013 | Martin et al. |
| 8,636,479 | B2 | 1/2014 | Kenyon et al. |
| 8,638,014 | B2 | 1/2014 | Sears et al. |
| 8,702,379 | B2 | 4/2014 | Frater et al. |
| 8,733,349 | B2 | 5/2014 | Bath et al. |
| 9,375,543 | B2 | 6/2016 | Librett et al. |
| 9,427,538 | B2 | 8/2016 | Daly et al. |
| 9,616,188 | B2 | 4/2017 | Grasmuck |
| 9,649,459 | B2 | 5/2017 | Taylor et al. |
| 9,656,034 | B2 | 5/2017 | Kepler et al. |
| 9,981,099 | B2 | 5/2018 | Feldhahn et al. |
| 10,092,716 | B2 | 10/2018 | Velzy et al. |
| 10,124,135 | B2 | 11/2018 | Kenyon et al. |
| 2005/0098179 | A1 | 5/2005 | Burton et al. |
| 2005/0166921 | A1 | 8/2005 | DeVries et al. |
| 2008/0310978 | A1 | 12/2008 | Hoffman |
| 2009/0007912 | A1 | 1/2009 | Lindell et al. |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2012/0301267 | A1 | 11/2012 | Baecke et al. |
| 2014/0102449 | A1 | 4/2014 | Lalonde |
| 2014/0158131 | A1 | 6/2014 | Kenyon |
| 2016/0310691 | A1 | 10/2016 | Bath et al. |
| 2017/0259019 | A1* | 9/2017 | Cariola ............. A61M 16/1055 |
| 2018/0140792 | A1 | 5/2018 | Lithgow et al. |
| 2018/0193577 | A1 | 7/2018 | Cariola et al. |
| 2018/0264215 | A1 | 9/2018 | Feldhahn et al. |
| 2018/0264222 | A1 | 9/2018 | Dantanarayana et al. |
| 2018/0369521 | A1 | 12/2018 | Velzy et al. |
| 2020/0188616 | A1 | 6/2020 | Kenyon et al. |

FOREIGN PATENT DOCUMENTS

| | | | |
|---|---|---|---|
| AU | 2012203574 | B2 | 10/2014 |
| CN | 101296721 | B | 5/2013 |
| EP | 2026863 | B1 | 6/2013 |
| EP | 1 773 455 | B1 | 11/2016 |
| EP | 1 933 910 | B1 | 11/2016 |
| EP | 2 968 804 | B1 | 8/2018 |
| JP | 2008-517682 | A | 5/2008 |
| JP | 2009-508647 | A | 3/2009 |
| JP | 4773443 | B2 | 9/2011 |
| JP | 5033803 | B2 | 9/2012 |
| JP | 2013-509219 | A | 3/2013 |
| JP | 2015-188764 | A | 11/2015 |
| JP | 2016-540599 | A | 12/2016 |
| JP | 2018-519925 | A | 7/2018 |
| WO | WO 98/04310 | A1 | 2/1998 |
| WO | WO 98/34665 | A1 | 8/1998 |
| WO | WO 00/78381 | A1 | 12/2000 |
| WO | WO 2004/073778 | A1 | 9/2004 |
| WO | WO 2005/063328 | A1 | 7/2005 |
| WO | WO 2005/097244 | A1 | 10/2005 |
| WO | WO 2006/074513 | A1 | 7/2006 |
| WO | WO 2006/130903 | A1 | 12/2006 |
| WO | WO 2009/052560 | A1 | 4/2009 |
| WO | WO 2010/135785 | A1 | 12/2010 |
| WO | WO 2011/022779 | A1 | 3/2011 |
| WO | WO 2011/086434 | A1 | 7/2011 |
| WO | WO 2012/171072 | A1 | 12/2012 |
| WO | WO 2013/020167 | A1 | 2/2013 |
| WO | WO 2016/086273 | A1 | 6/2016 |
| WO | WO 2017/006189 | A1 | 1/2017 |

OTHER PUBLICATIONS

Notice of Reasons for Refusal mailed Mar. 4, 2024 in Japanese Application No. 2023-094152, with English translation, 9 pages.
"Respiratory Physiology", by John B. West, Lippincott Williams & Wilkins, 9th edition published 2012 (8 pages).
Kenyon et al., U.S. Appl. No. 16/711,999, filed Dec. 12, 2019, for "Pneumatic Block for Respiratory Pressure Therapy Device," (parent application).
Notification of Transmittal of the International Search Report and the Written Opinion of the International Searching Authority, or the Declaration mailed Feb. 20, 2020 in International Application No. PCT/IB2019/060726, 5 pages.
Written Opinion of the International Searching Authority mailed Feb. 20, 2020 in International Application No. PCT/IB2019/060726, 6 pages.
Written Opinion of the International Preliminary Searching Authority mailed Nov. 12, 2020 in International Application No. PCT/IB2019/060726, 7 pages.
Written Opinion of the International Preliminary Searching Authority mailed Feb. 9, 2021 in International Application No. PCT/IB2019/060726, 8 pages.
Notification of Transmittal of International Preliminary Report on Patentability mailed Mar. 26, 2021 in International Application No. PCT/IB2019/060726, 7 pages.
Notice of Reasons for Rejection mailed Jun. 20, 2022 in Japanese Application No. 2021-533624, with English translation, 15 pages.
Notice of Reasons for Rejection mailed Dec. 5, 2022 in Japanese Application No. 2021-533624, with English translation, 22 pages.
Notice of Reasons for Refusal mailed Apr. 7, 2026 in Japanese Application No. 2024-224340, with English translation, 11 pages.
Examination Report mailed Aug. 4, 2026 in Australian Application No. 2025220788, 6 pages.

* cited by examiner

Copyright 2012 ResMed Limited

Copyright 2012 ResMed Limited

Copyright 2015 ResMed Limited

PNEUMATIC BLOCK FOR RESPIRATORY PRESSURE THERAPY DEVICE

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

1 CROSS-REFERENCE TO RELATED APPLICATIONS

This application is a continuation of U.S. application Ser. No. 16/711,999, filed Dec. 12, 2019, which claims the benefit of U.S. Provisional Application No. 62/779,135, filed Dec. 13, 2018, each of which is incorporated herein by reference in their entirety.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/ or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 $cmH_2O$).

| RPT Device name | A-weighted sound pressure level dB (A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers.

While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of the present technology relates to an apparatus for providing air at positive pressure for respiratory therapy to a patient. The apparatus includes a pneumatic block including a chassis assembly configured to support each of multiple blower sub-assemblies, with corresponding mounting plates of the blower sub-assemblies dividing the pneumatic block into different muffler chambers.

Another aspect of the present technology relates to an apparatus for providing air at positive pressure for respiratory therapy to a patient. The apparatus includes a pneumatic block including at least first and second blower sub-assemblies and a common chassis assembly configured to support each of the at least first and second blower sub-assemblies. The at least first and second blower sub-assemblies are different structurally from one another in at least one aspect. Each of the at least first and second blower sub-assemblies includes a corresponding blower configured to produce a flow of air at a therapeutic pressure. The common chassis assembly and the first blower sub-assembly form a first configuration of the pneumatic block, and the common chassis assembly and the second blower sub-assembly form a second configuration of the pneumatic block. Each of the first and second configurations of the pneumatic block form an air flow path extending from a chassis inlet to a chassis outlet. Each of the first and second configurations of the pneumatic block form a chamber arrangement including a plurality of chambers along the air flow path. The air flow path and the chamber arrangement of the first configuration of the pneumatic block is different than the air flow path and the chamber arrangement of the second configuration of the pneumatic block.

Another aspect of the present technology relates to an apparatus for providing air at positive pressure for respiratory therapy to a patient. The apparatus includes a pneumatic block. The pneumatic block forms a chamber arrangement including a plurality of chambers along an air flow path. In an example, the plurality of chambers are arranged in more than one plane. In an example, at least one chamber extends in a first plane and at least one chamber extends in a second plane that is vertically spaced from the first plane. In an example, the chamber arrangement includes three inlet muffler chambers and an outlet chamber along the air flow path. In an example, one of the three inlet muffler chambers extends in a first plane, and the remaining two of the three inlet muffler chambers and the outlet chamber extend in a second plane that is vertically spaced from the first plane.

Another aspect of the present technology relates to an apparatus for providing air at positive pressure for respiratory therapy to a patient. The apparatus includes a pneumatic block. The pneumatic block forms a chamber arrangement including a plurality of chambers along an air flow path. In an example, the chamber arrangement includes at least one inlet muffler chamber positioned upstream of a blower inlet of the blower and an outlet chamber positioned downstream of a blower outlet of the blower. In an example, the chamber arrangement includes at least two inlet muffler chambers positioned upstream of a blower inlet of the blower and an outlet chamber positioned downstream of a blower outlet of the blower. In an example, the chamber arrangement includes three inlet muffler chambers positioned upstream of a blower inlet of the blower and an outlet chamber positioned downstream of a blower outlet of the blower. In an example, a first of the three inlet muffler chambers receives air from a chassis inlet, and the blower is provided in a second of the three inlet muffler chambers and receives air at the blower inlet from a third of the three inlet muffler chambers. In an example, the outlet chamber is adapted to communicate with an inlet of a water reservoir for humidification.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

4.3 Patient Interface

Figure 3A:
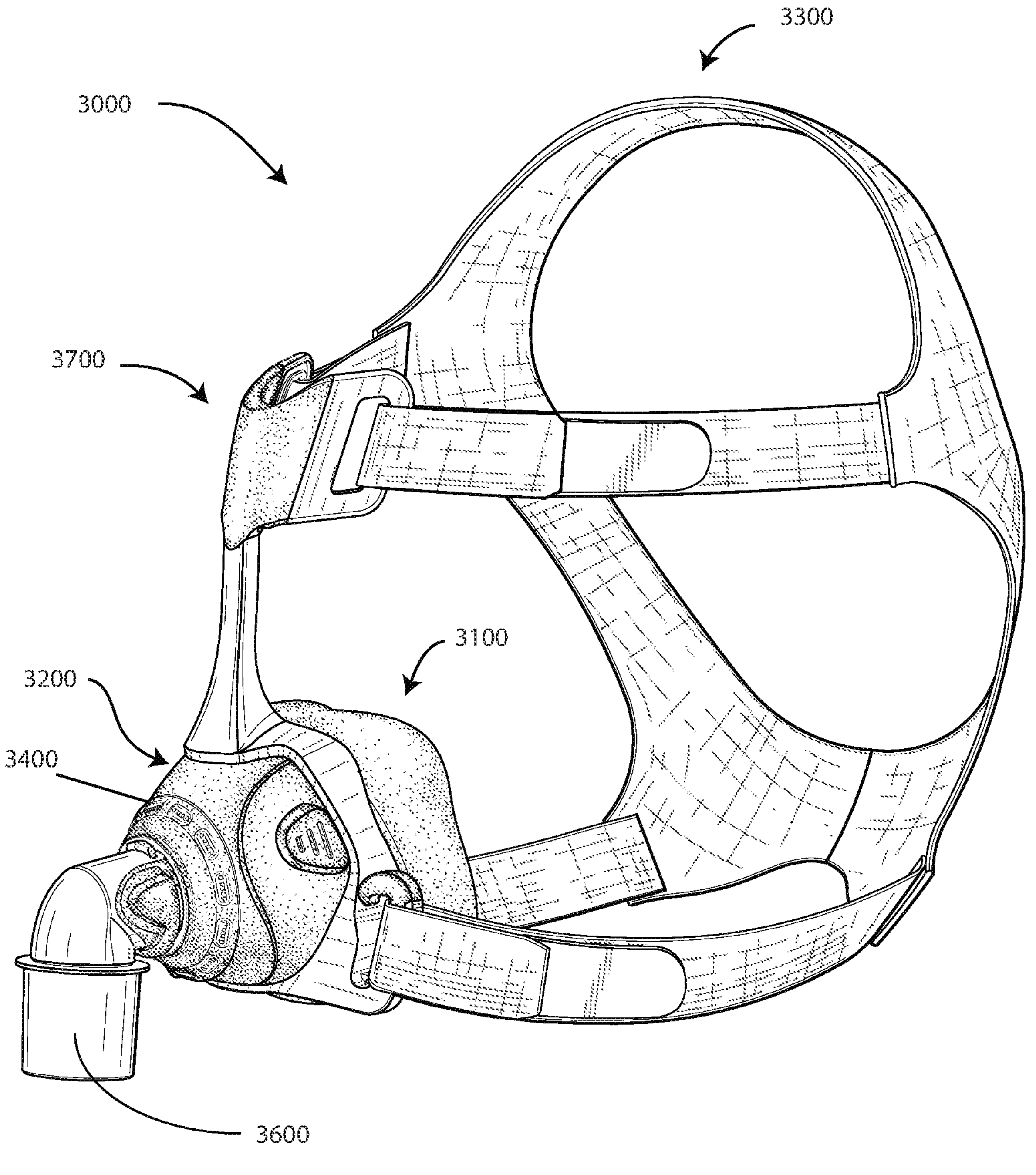

FIG. 3A shows a patient interface in the form of a nasal mask in accordance with one form of the present technology.

Figure 3B:
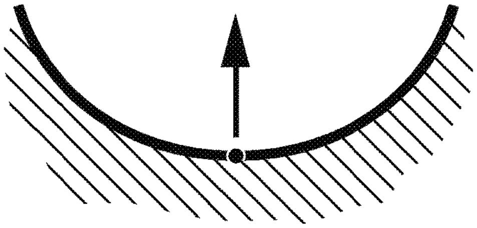

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
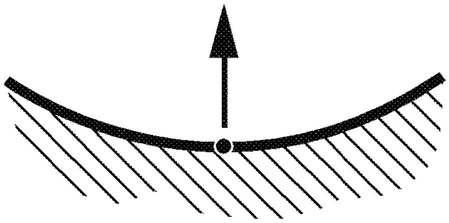

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
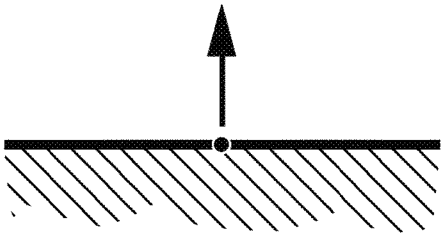

FIG. 3D shows a schematic of a cross-section through a structure at a point. An outward normal at the point is indicated. The curvature at the point has a value of zero.

Figure 3E:
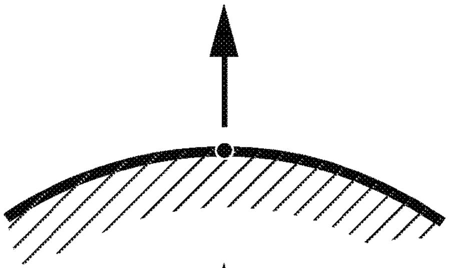

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
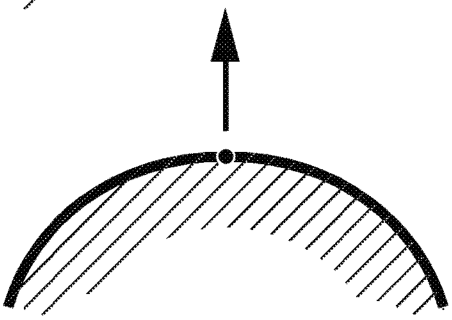

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3G:
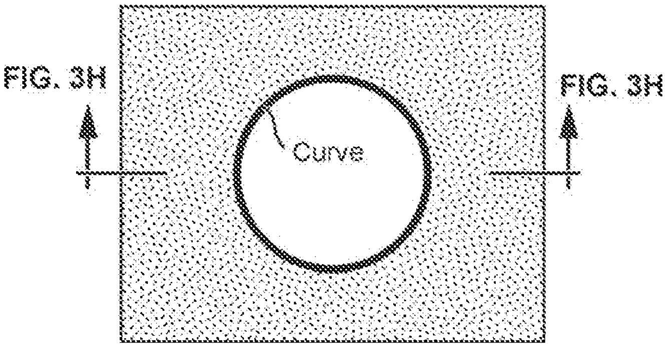

FIG. 3G shows the surface of a structure, with a one dimensional hole in the surface. The illustrated plane curve forms the boundary of a one dimensional hole.

Figure 3H:
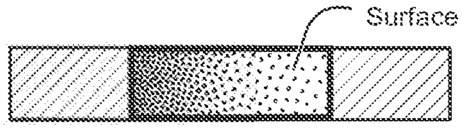

FIG. 3H shows a cross-section through the structure of FIG. 3G. The illustrated surface bounds a two dimensional hole in the structure of FIG. 3G.

Figure 3I:
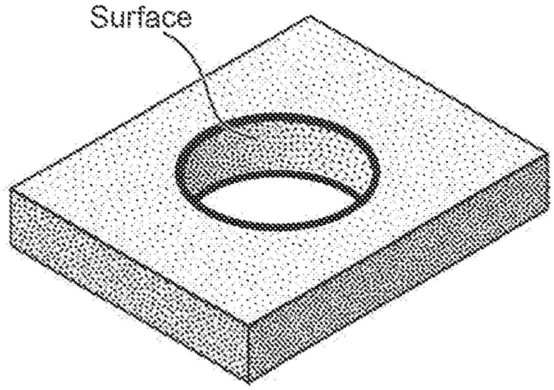

FIG. 3I shows a perspective view of the structure of FIG. 3G, including the two dimensional hole and the one dimensional hole. Also shown is the surface that bounds a two dimensional hole in the structure of FIG. 3G.

4.4 Breathing Waveforms

Figure 4:
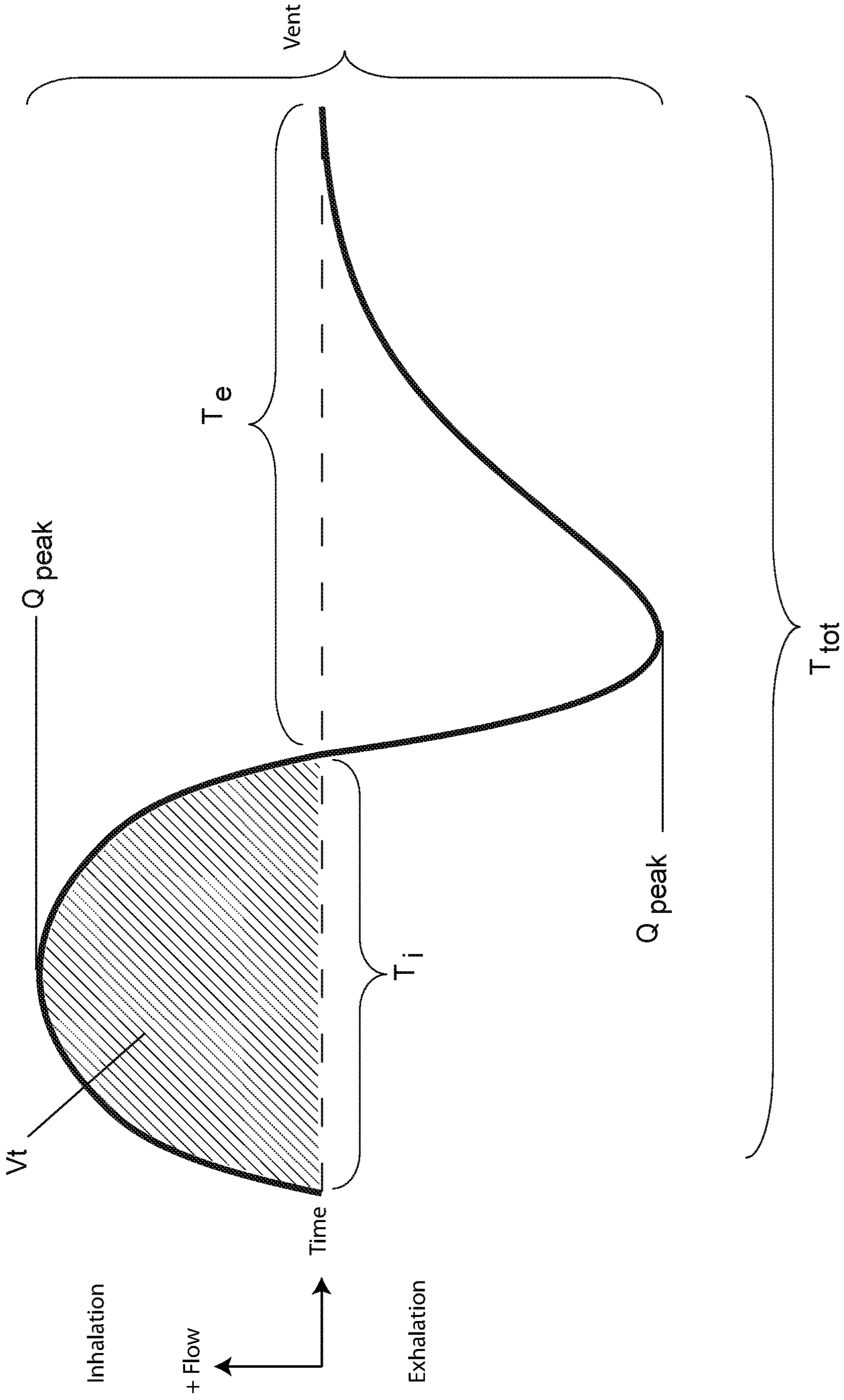

FIG. 4 shows a model typical breath waveform of a person while sleeping.

4.5 RPT Device and Humidifier

Figure 5A:
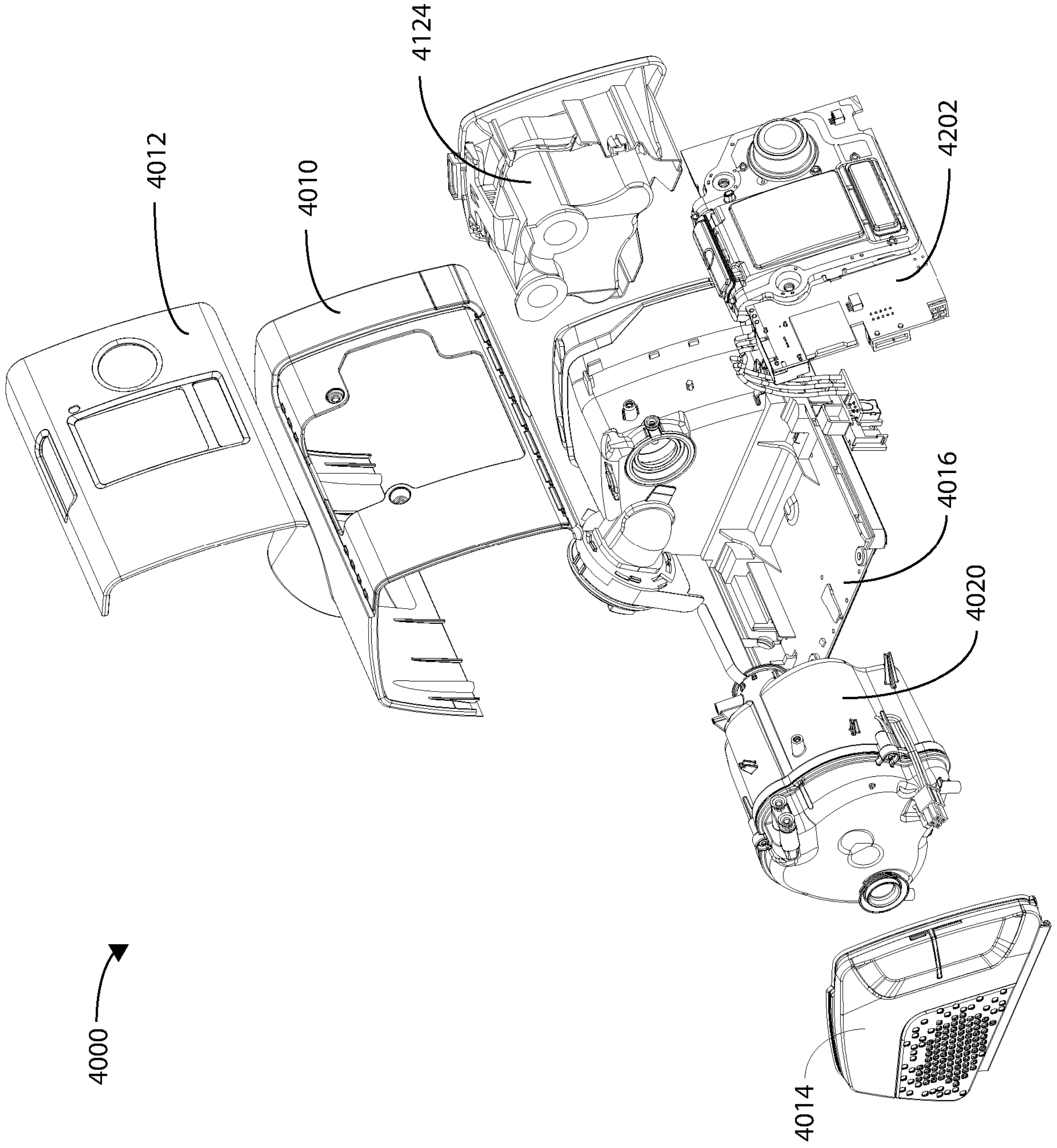

FIG. 5A shows an exploded perspective view of an RPT device in accordance with one form of the present technology.

Figure 5B:
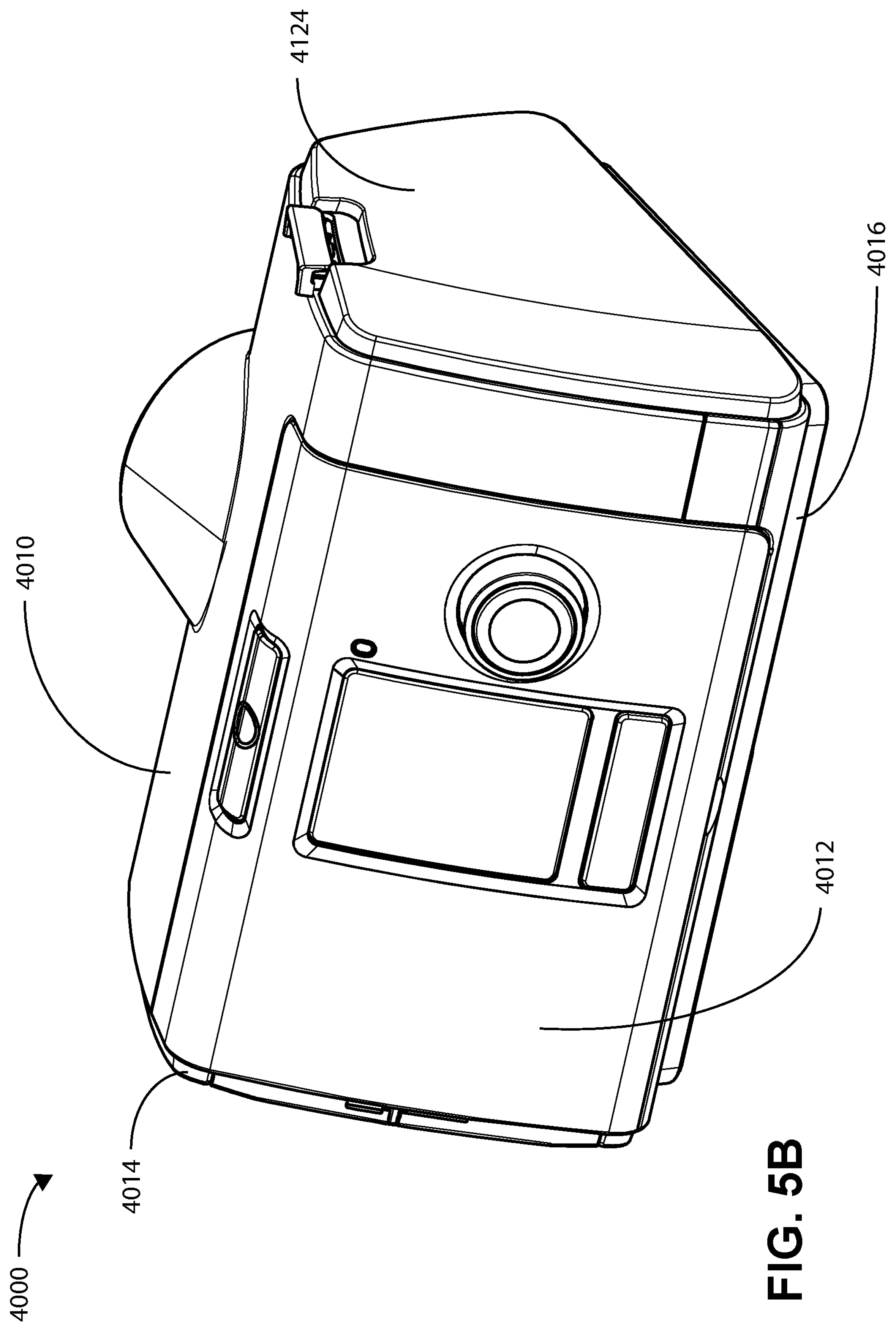

FIG. 5B shows a perspective view of an RPT device 4000 comprising an outlet muffler 4124 in accordance with one form of the present technology.

Figure 5C:
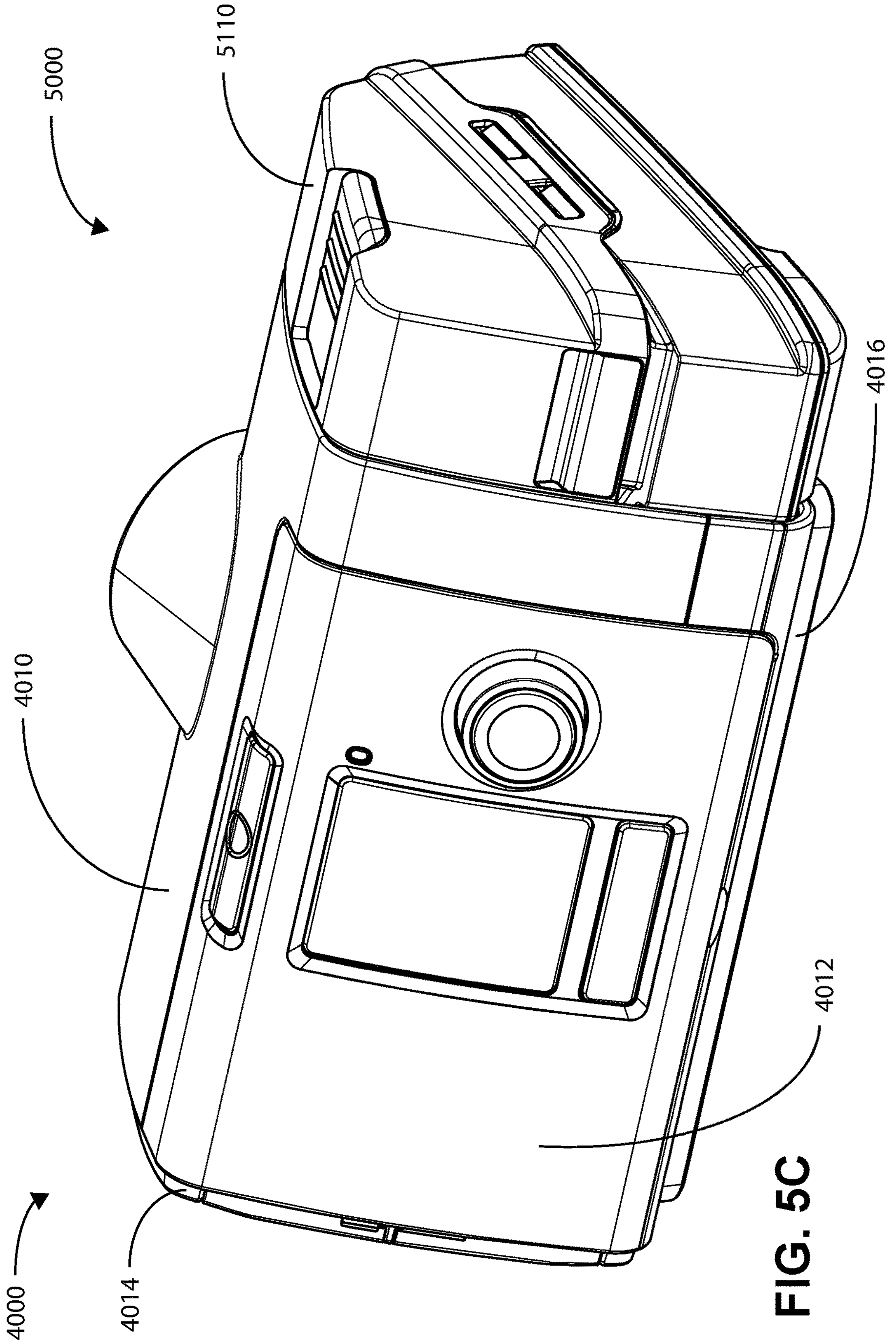

FIG. 5C shows a perspective view of an RPT device 4000 with an integrated humidifier 5000 comprising a water reservoir 5110 in accordance with one form of the present technology.

Figure 5D:
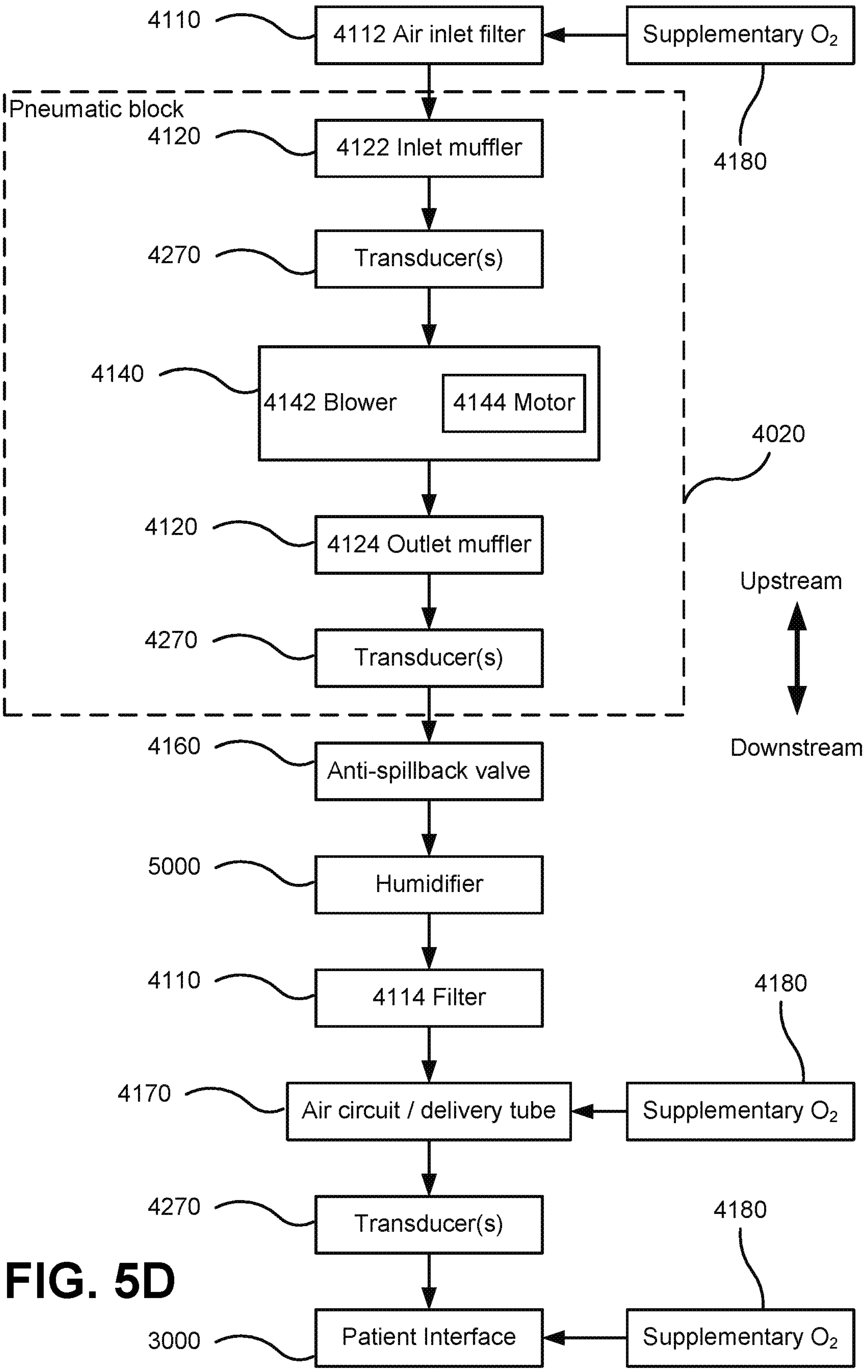

FIG. 5D is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 5E:
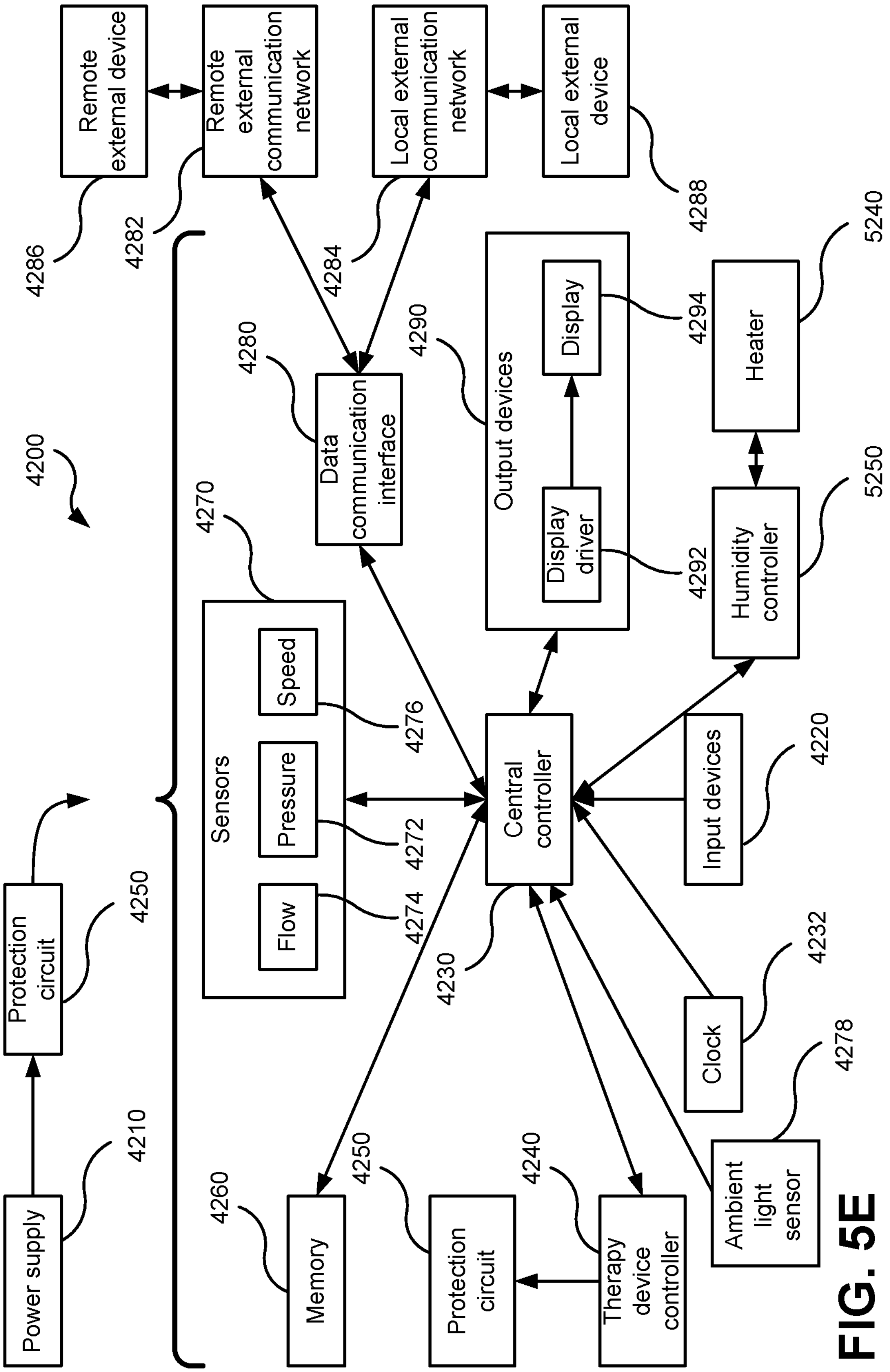

FIG. 5E is a schematic diagram of the electrical components of an RPT device in accordance with one form of the present technology.

Figure 5F:
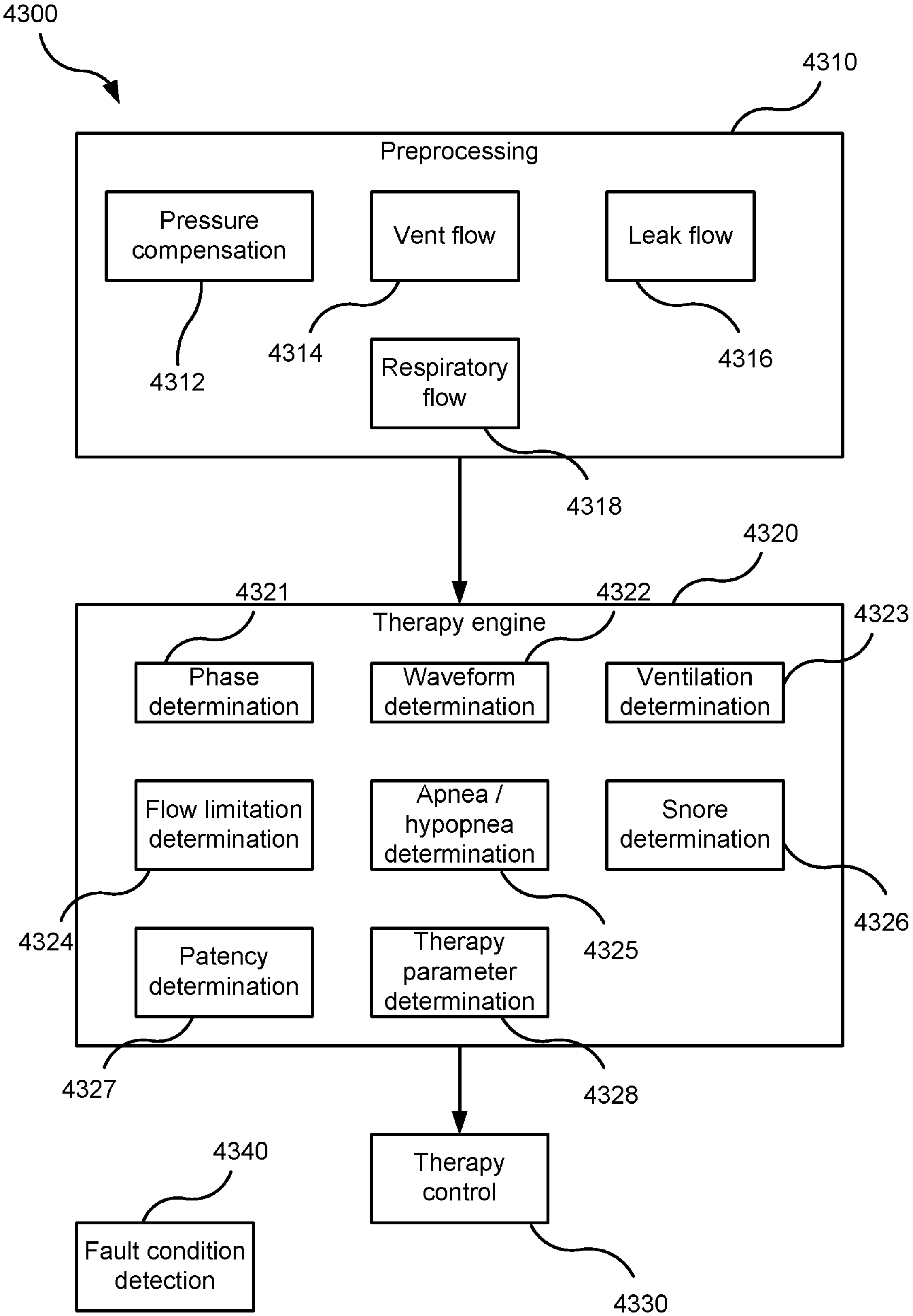

FIG. 5F is a schematic diagram of the algorithms implemented in an RPT device in accordance with one form of the present technology.

Figure 5G:
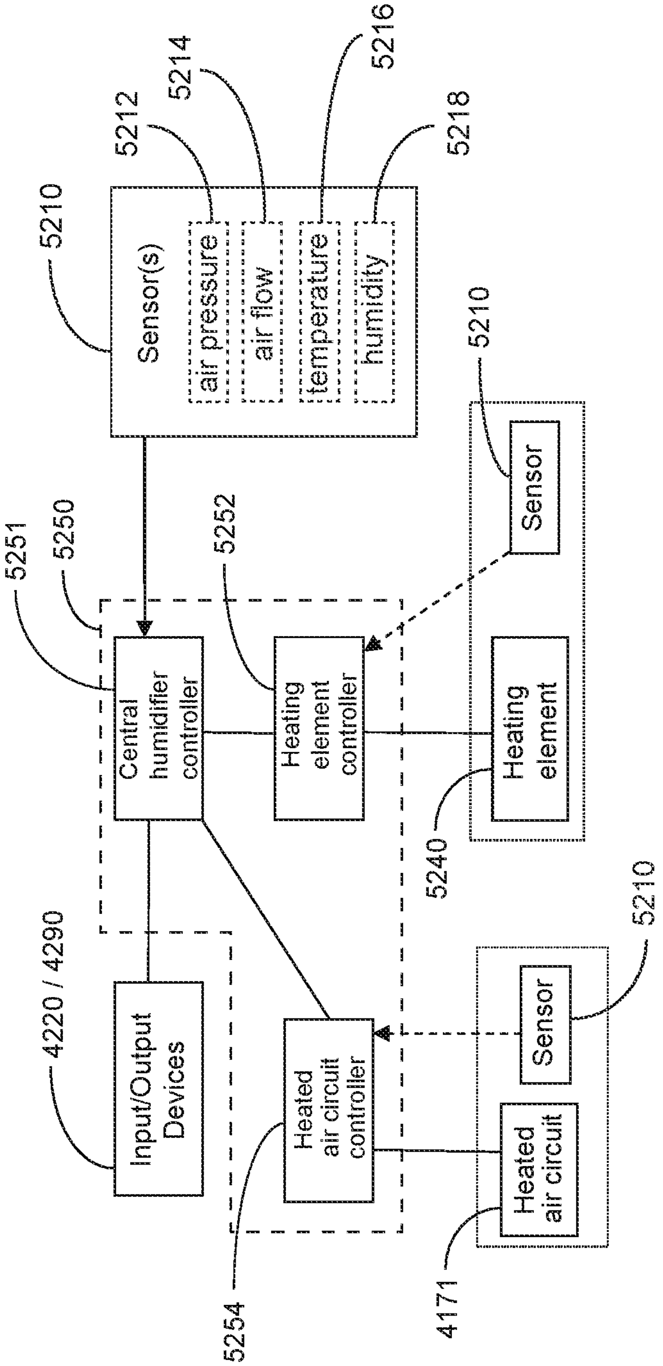

FIG. 5G shows a schematic of a humidifier in accordance with one form of the present technology.

Figure 6:
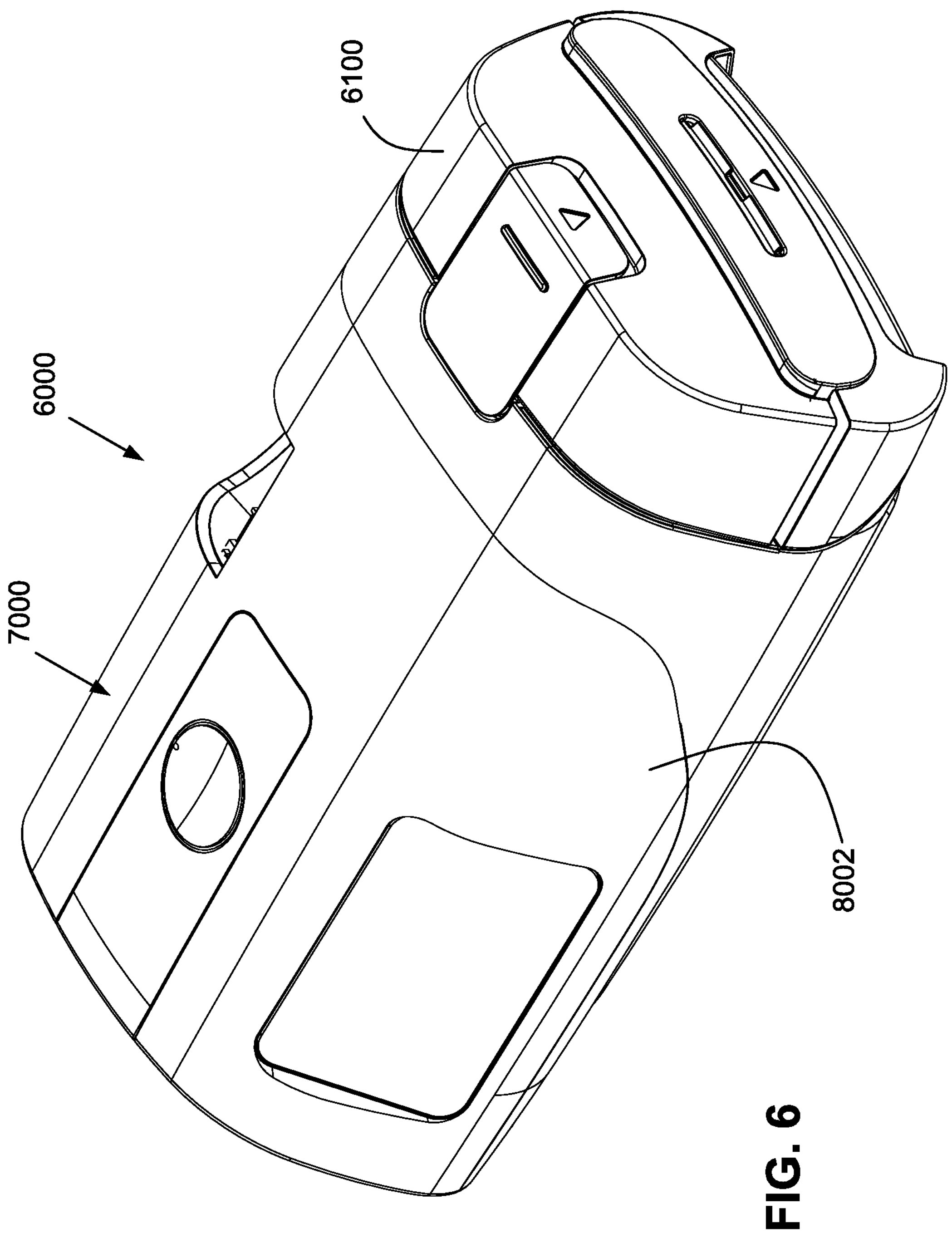

FIG. 6 is a perspective view of an RPT device with an integrated humidifier comprising a water reservoir according to an example of the present technology.

Figure 7:
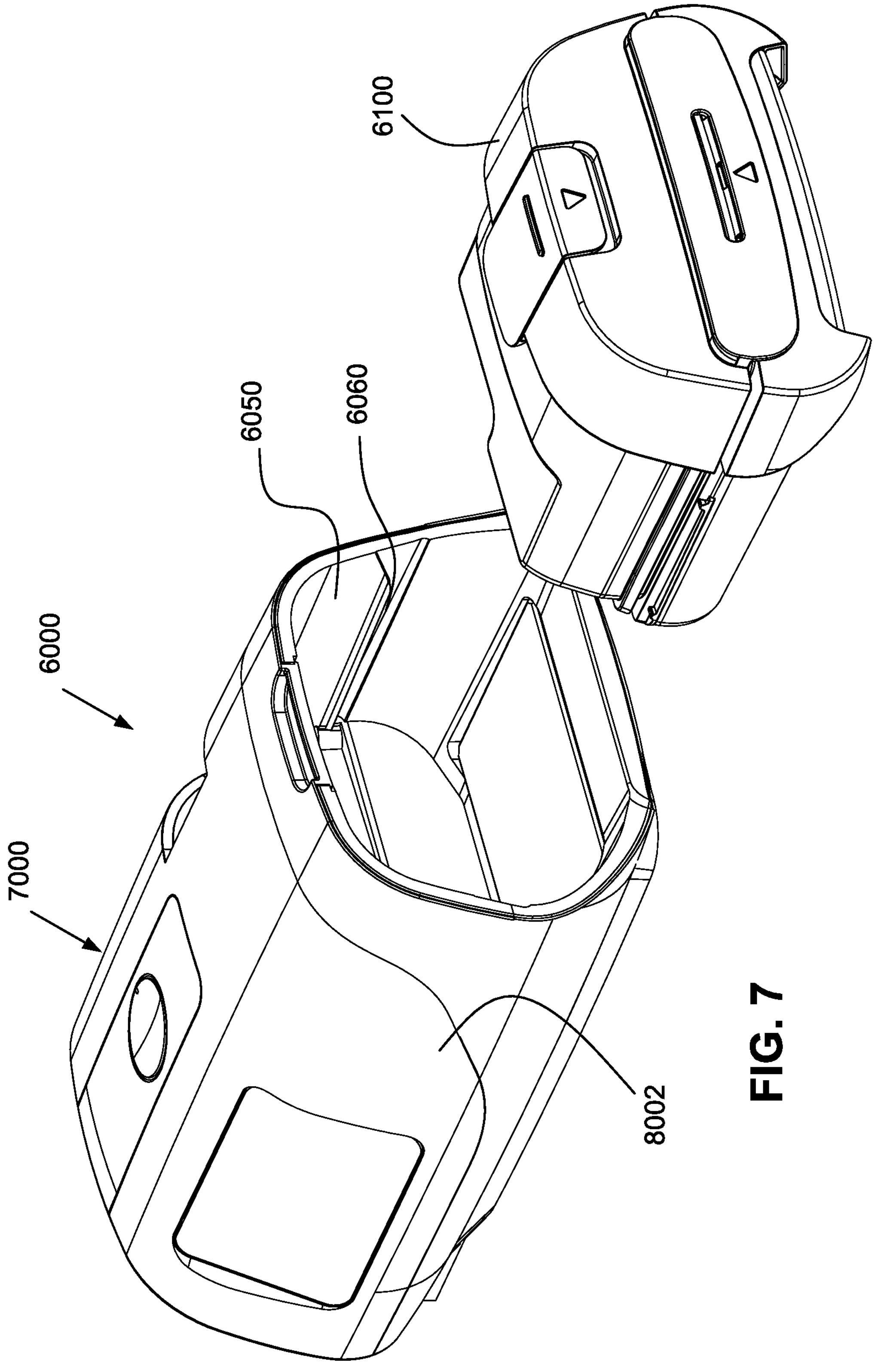

FIG. 7 is a perspective view of the RPT device and integrated humidifier of FIG. 6 with the water reservoir removed from the reservoir dock.

Figure 8:
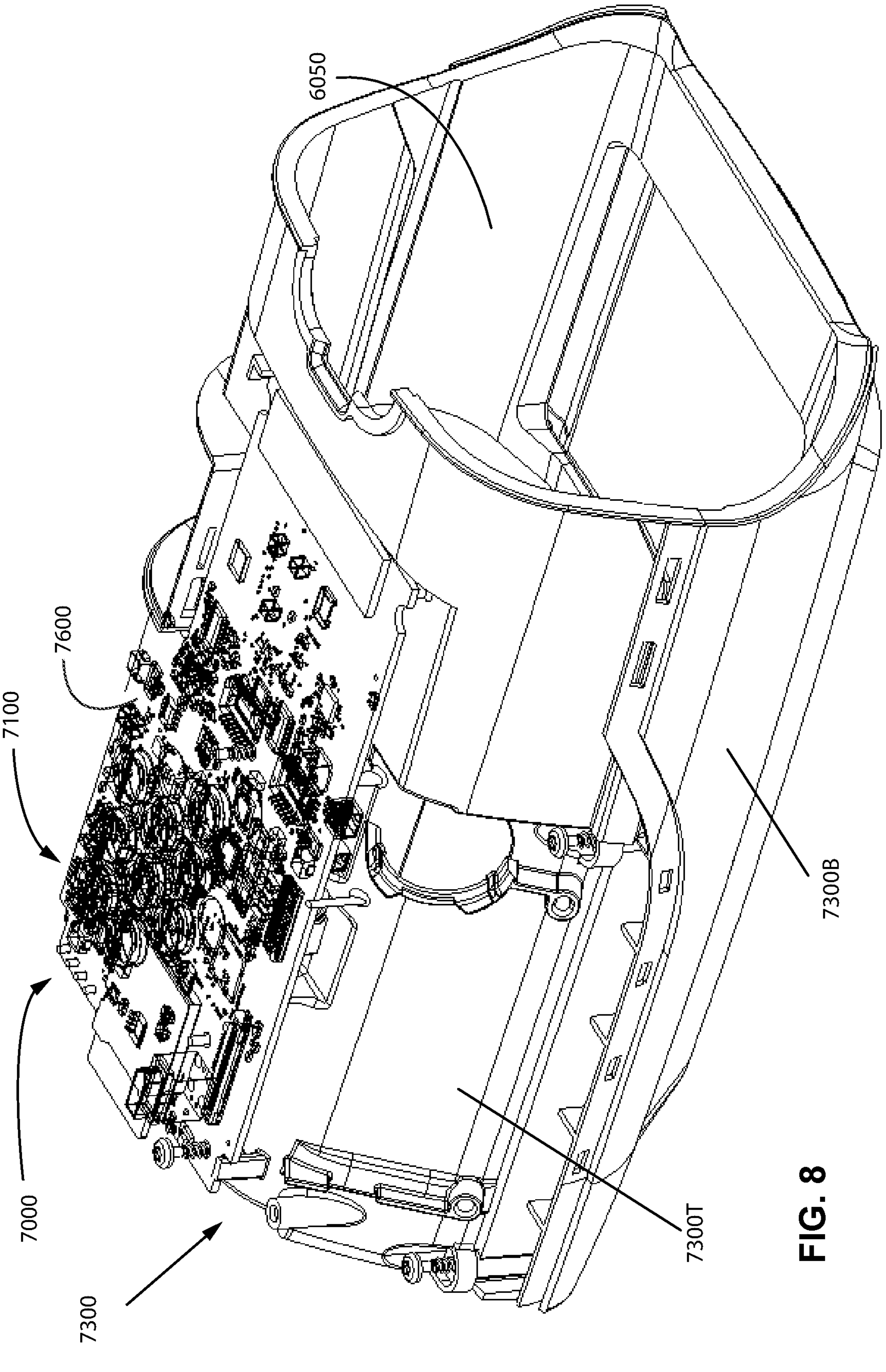

FIG. 8 is a perspective view of a pneumatic block and PCBA according to an example of the present technology.

Figure 9:
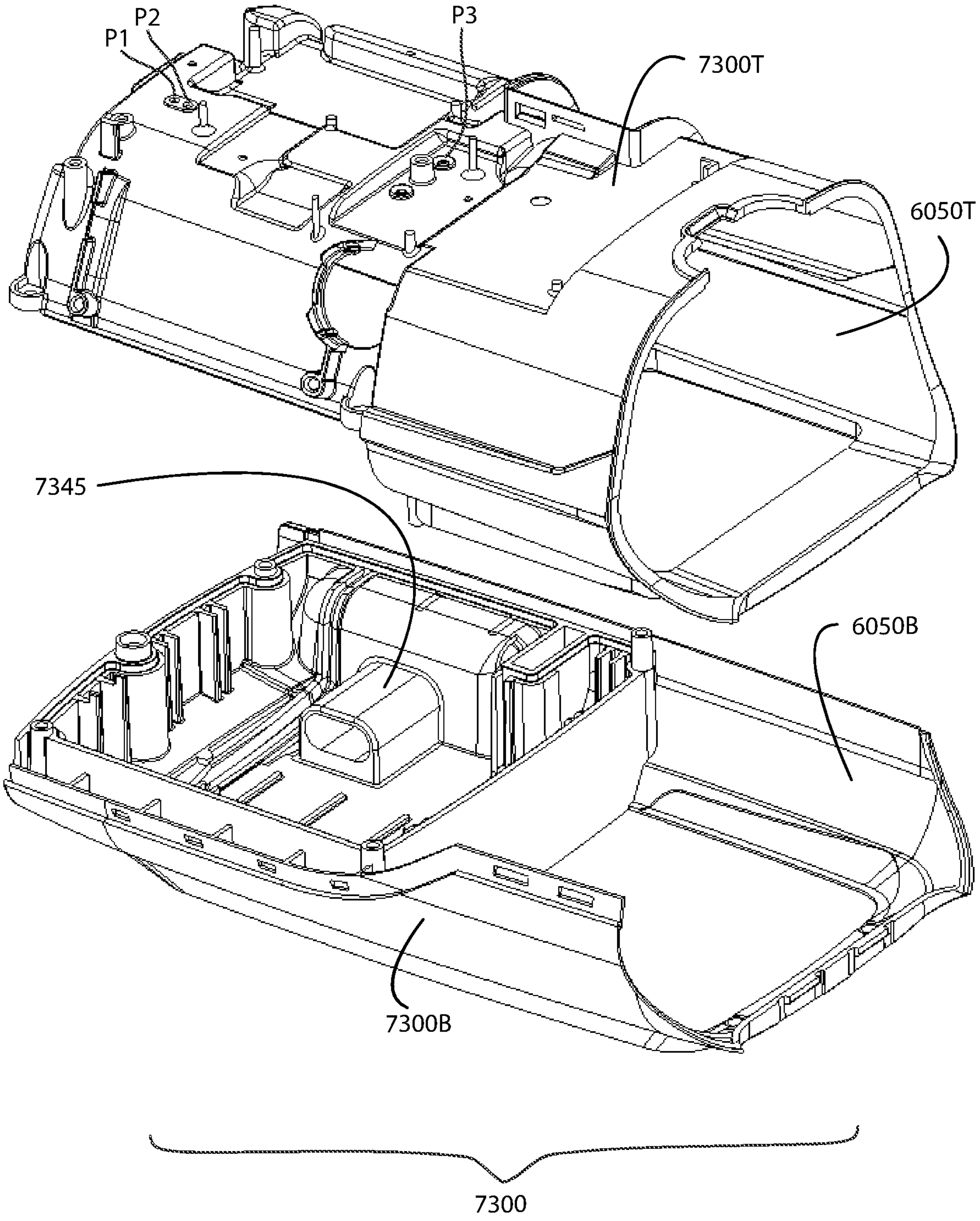

FIG. 9 is an exploded view of the pneumatic block of FIG. 8.

Figure 10:
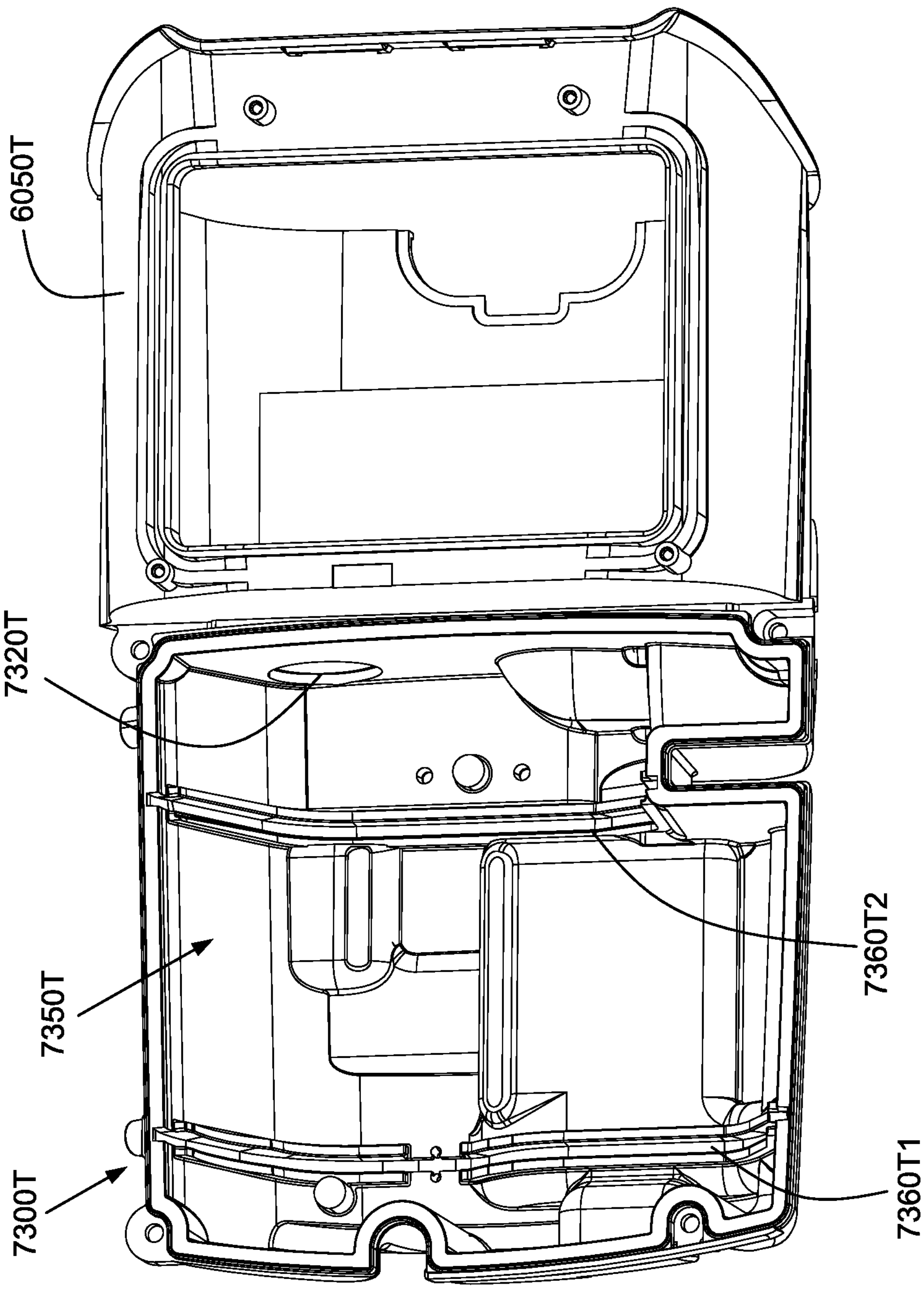

FIG. 10 is a bottom view of a top chassis of a chassis assembly according to an example of the present technology.

Figure 11:
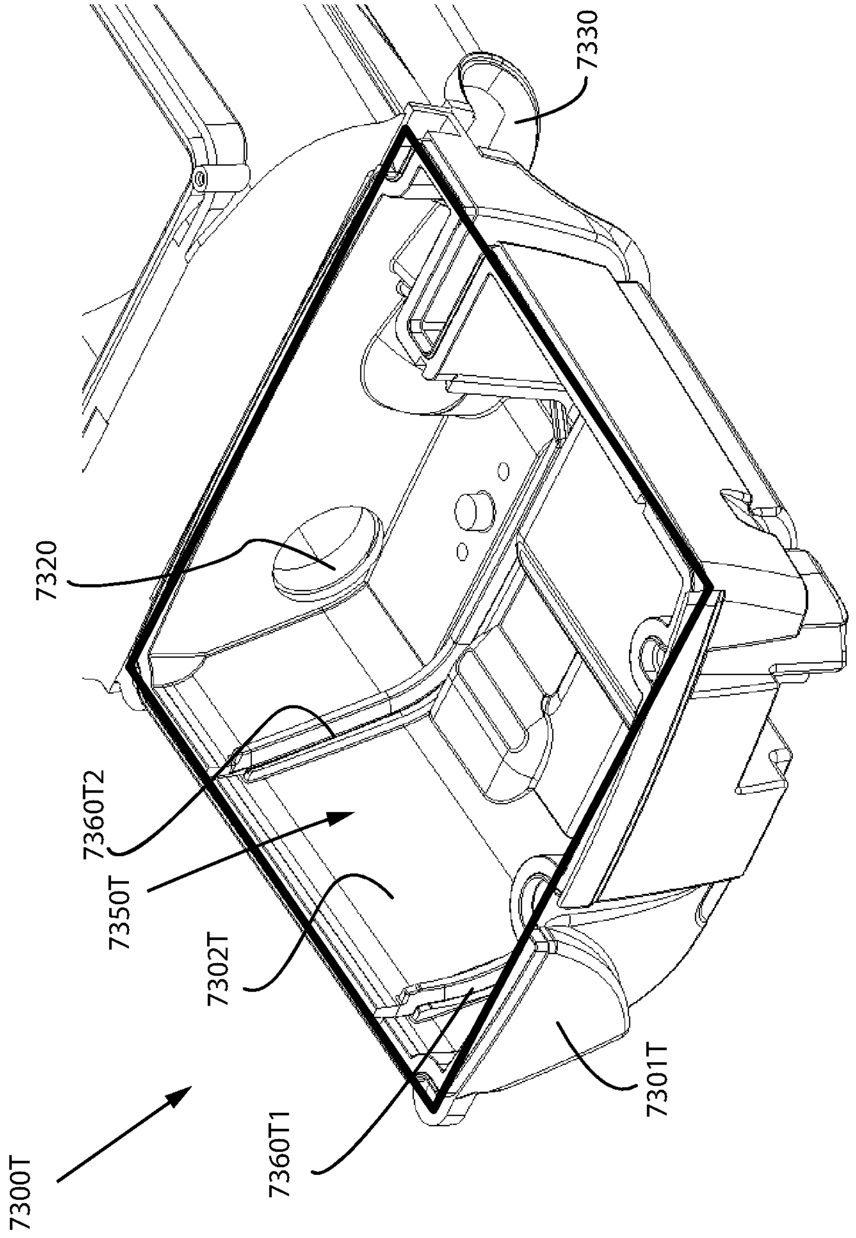

FIG. 11 is a bottom perspective view of the top chassis of FIG. 10.

Figure 12:
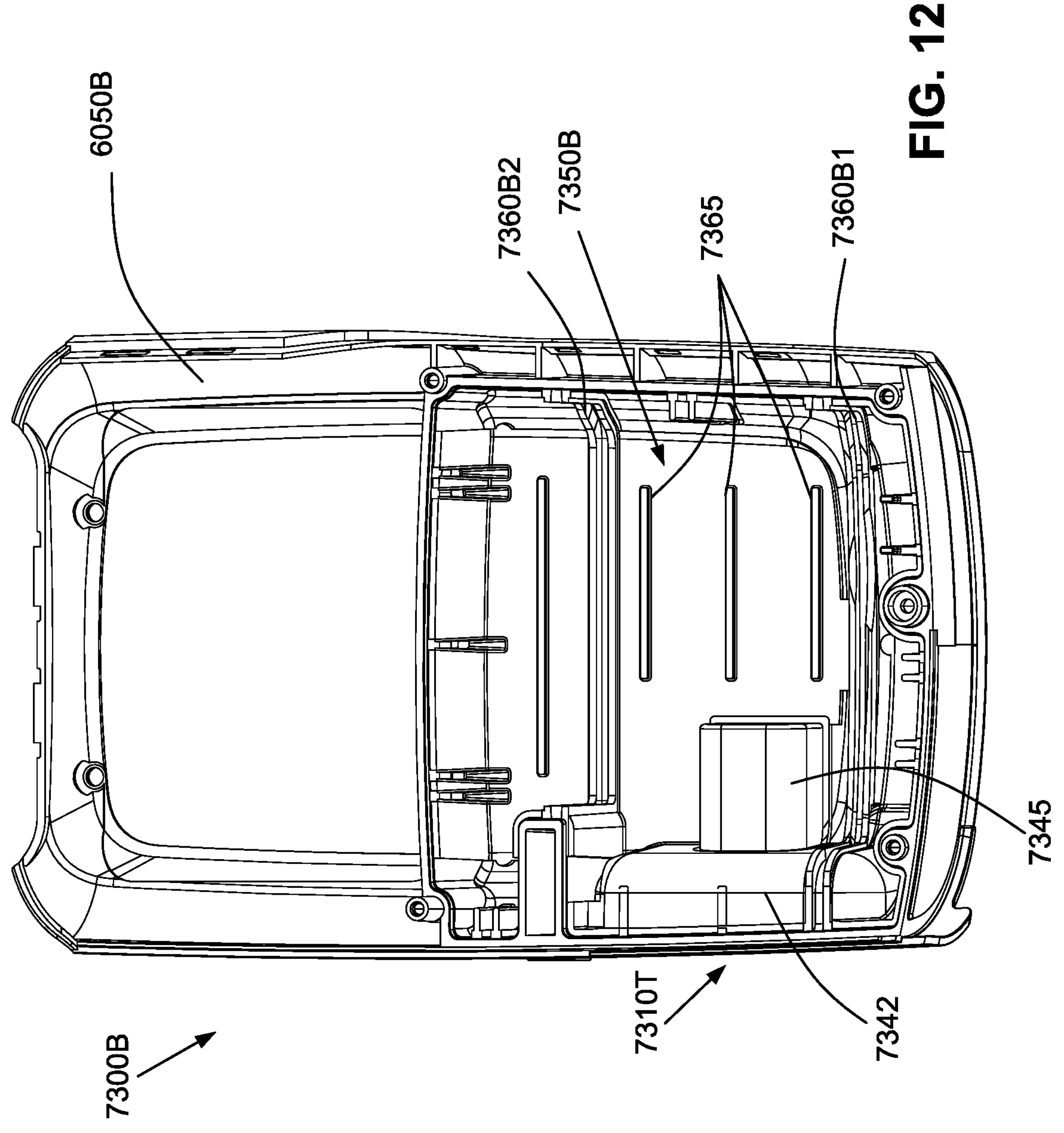

FIG. 12 is a top view of a bottom chassis of a chassis assembly according to an example of the present technology.

Figure 13:
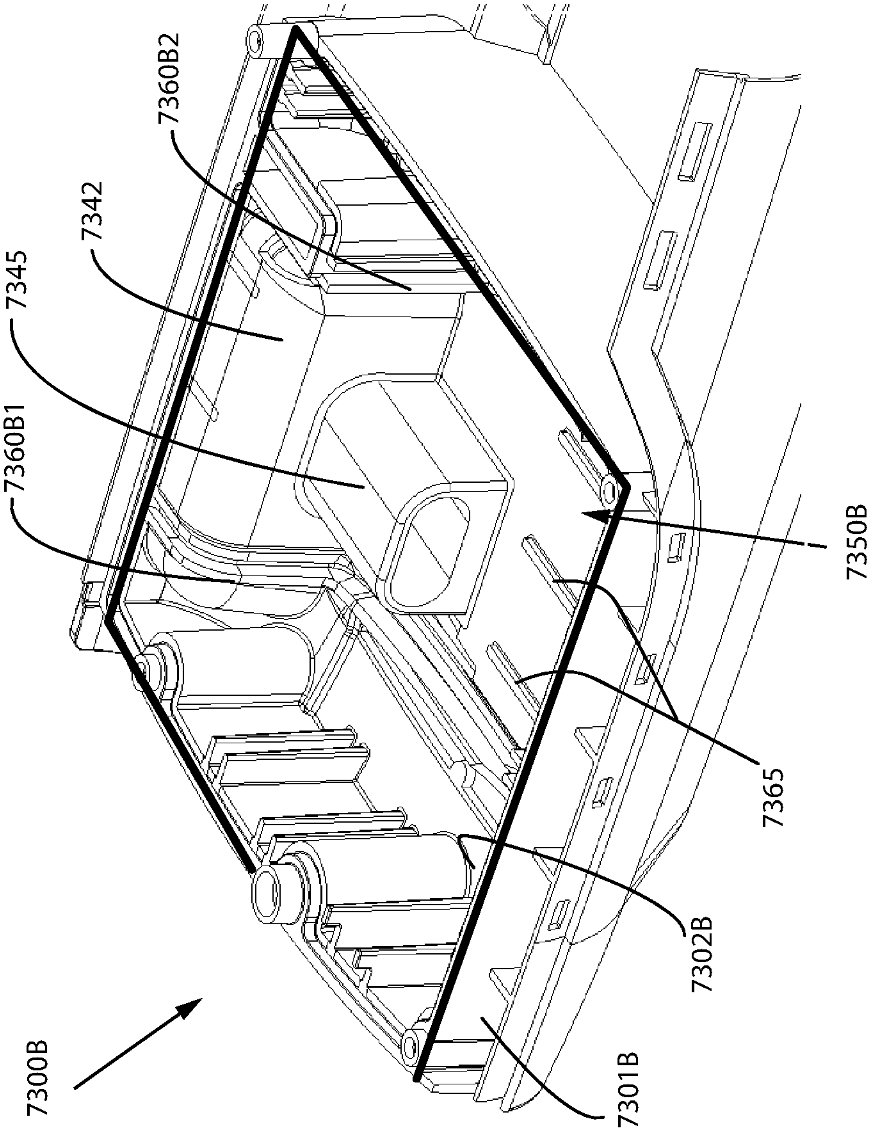

FIG. 13 is a top perspective view of the bottom chassis of FIG. 12.

Figure 14:
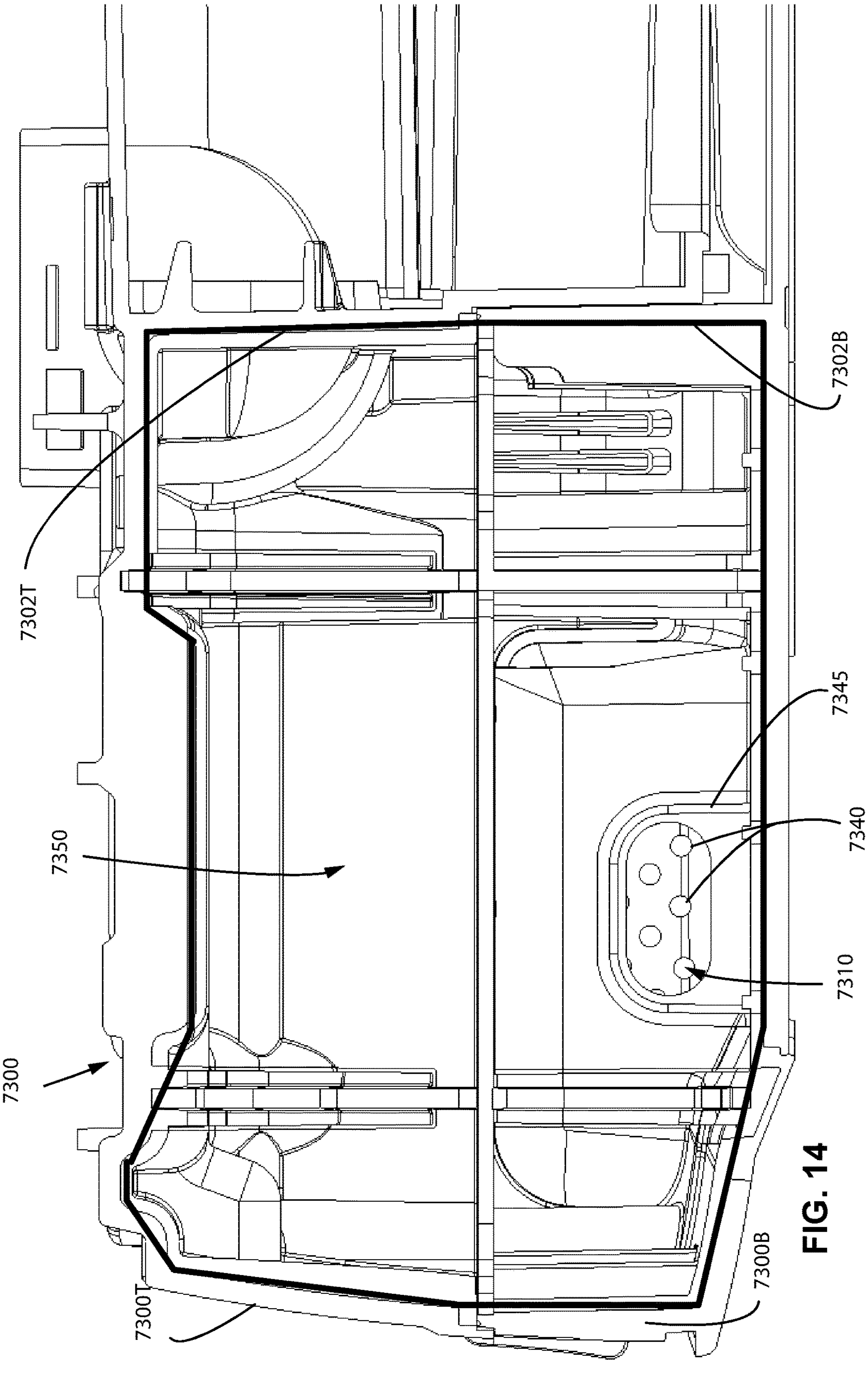

FIG. 14 is a cross-sectional view of a chassis assembly according to an example of the present technology.

Figure 15:
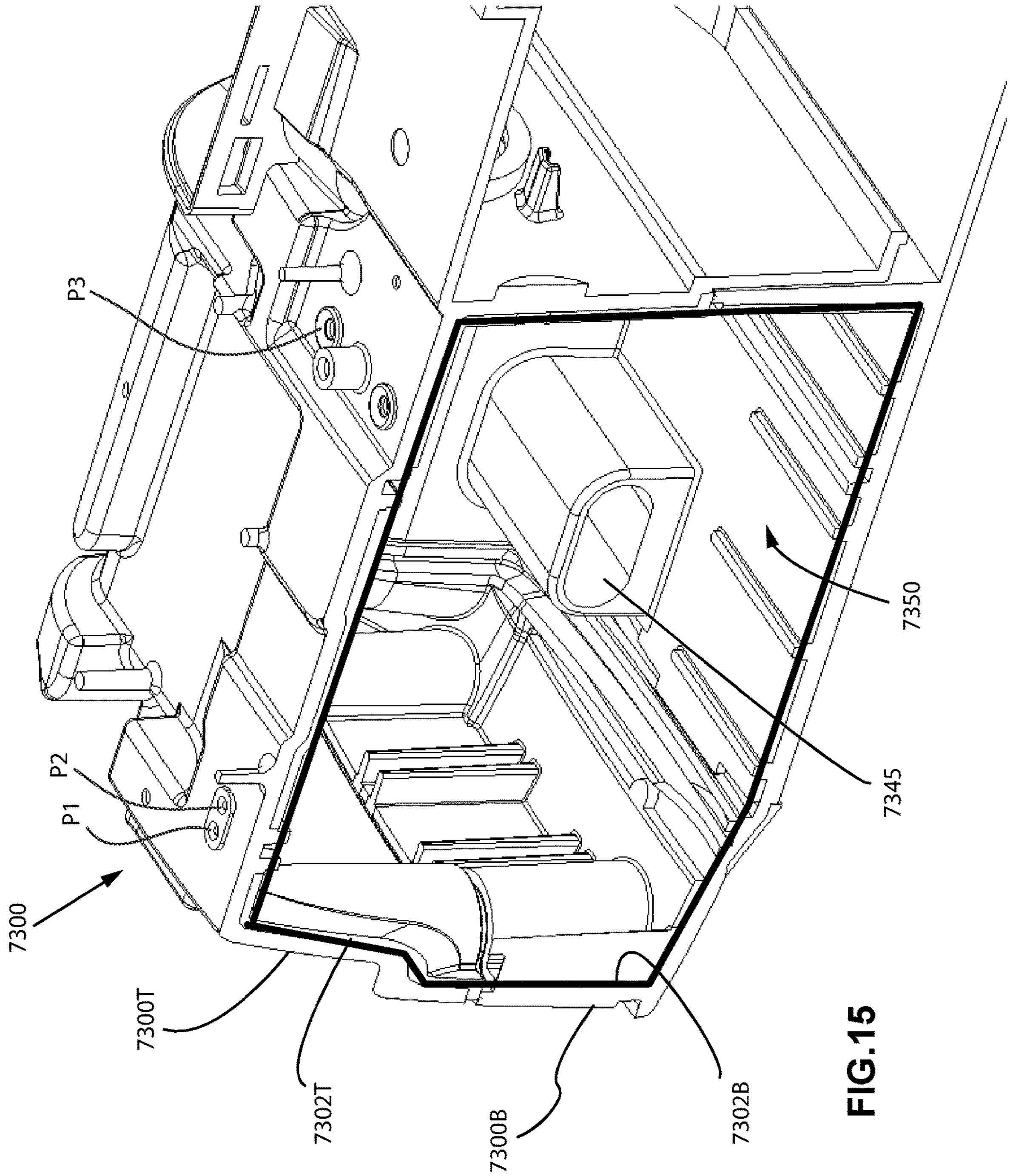

FIG. 15 is a cross-sectional view of a chassis assembly according to an example of the present technology.

Figure 16:
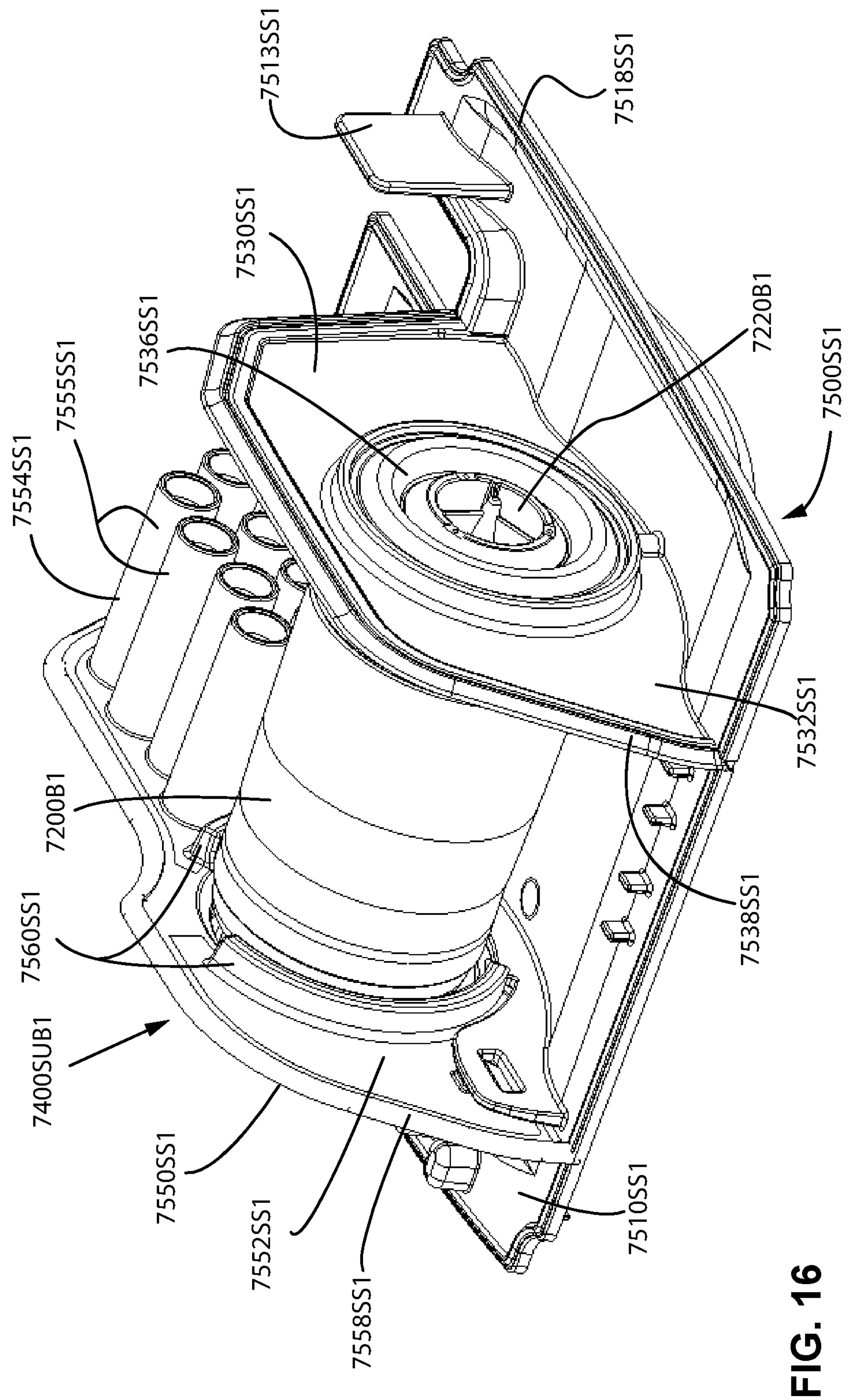

FIG. 16 is a perspective view of a first blower sub-assembly according to an example of the present technology.

Figure 17:
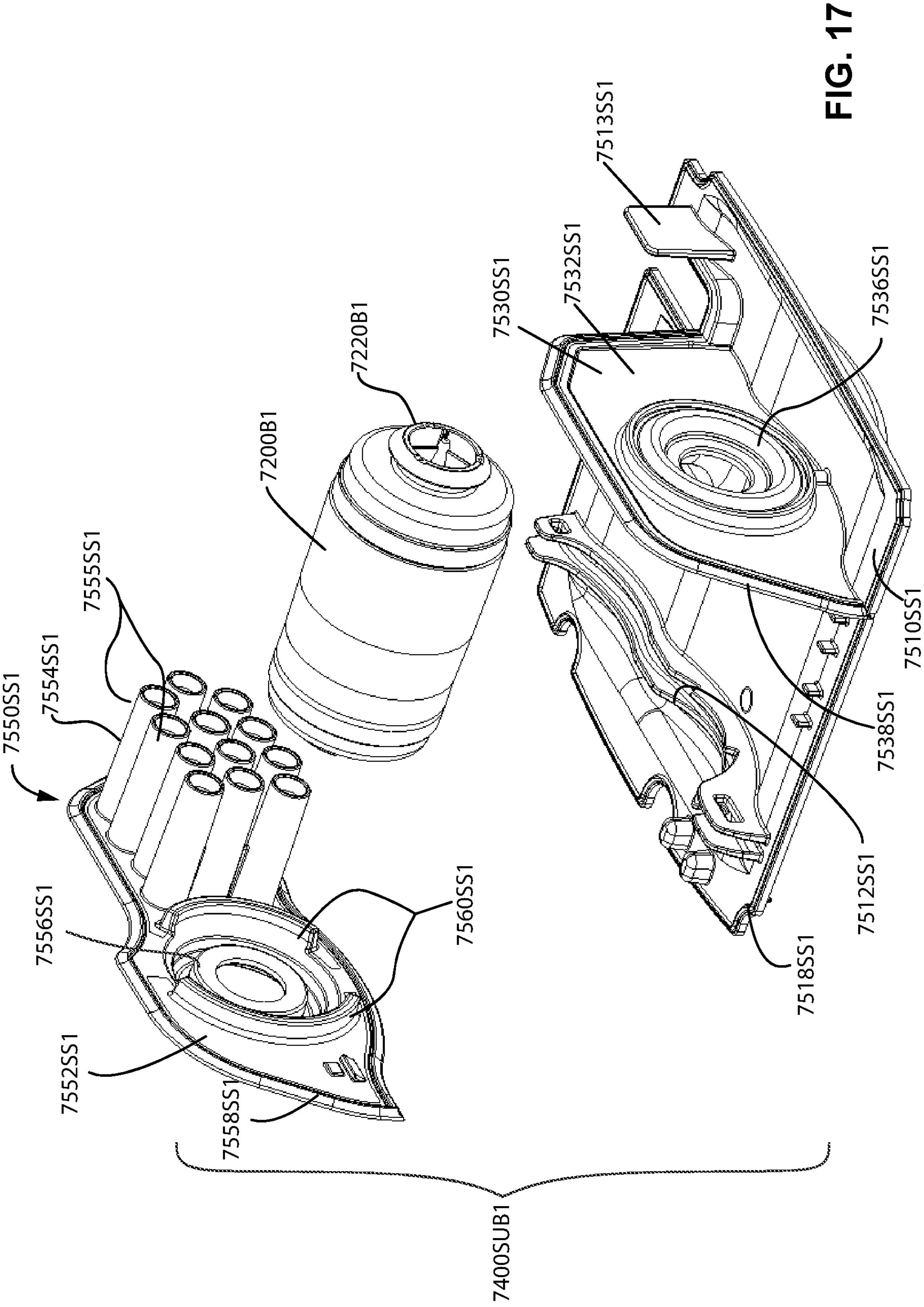

FIG. 17 is an exploded view of the first blower sub-assembly of FIG. 16.

Figure 18:
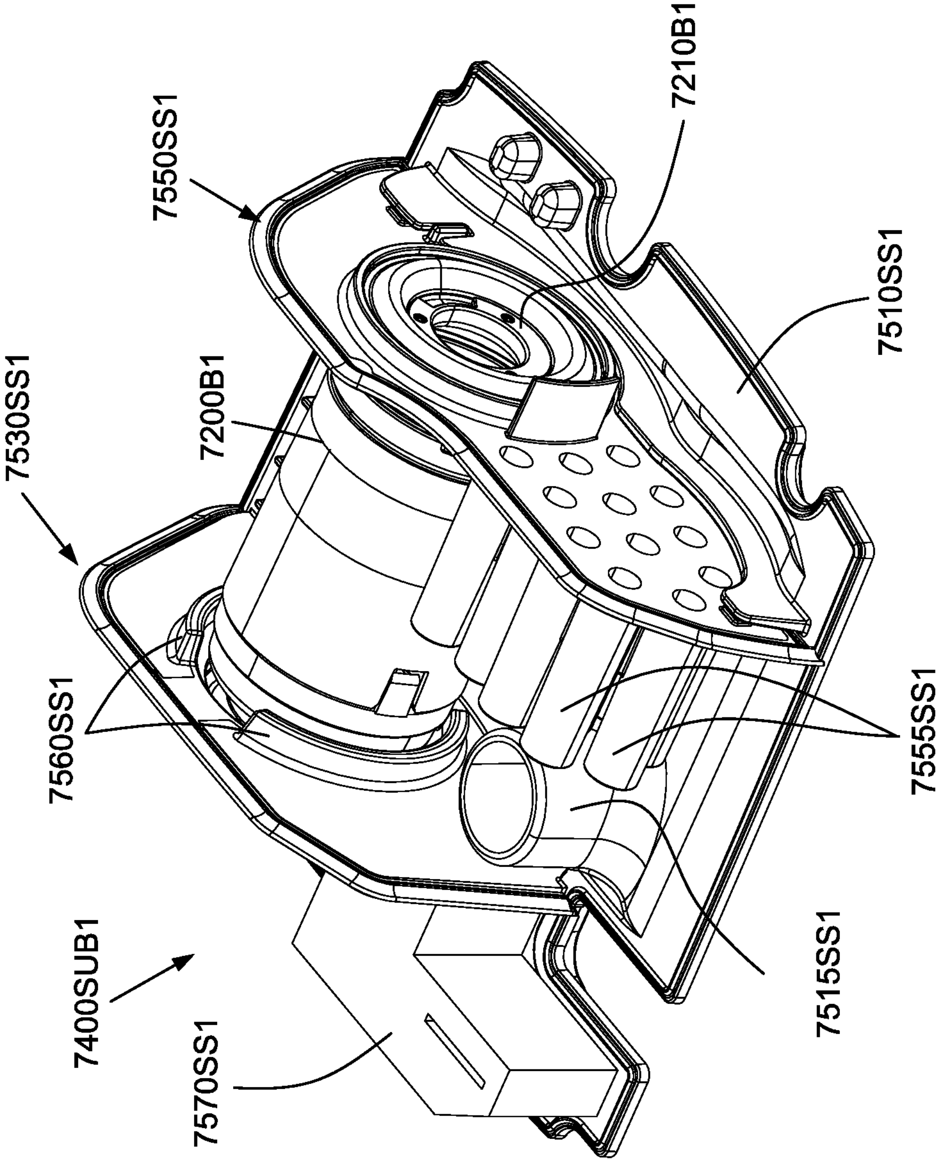

FIG. 18 is a perspective view of the first blower sub-assembly with outlet foam according to an example of the present technology.

Figure 19:
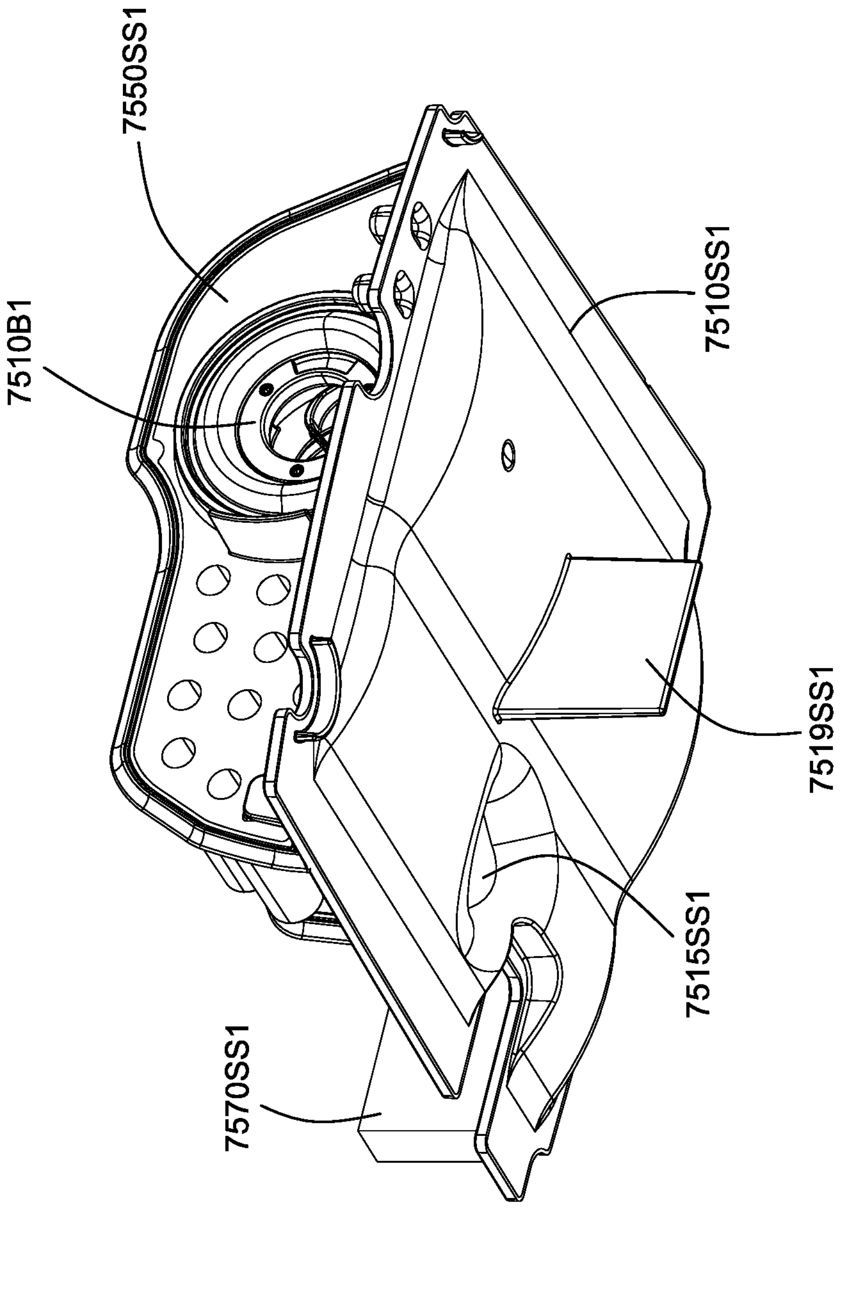

FIG. 19 is another perspective view of the first blower sub-assembly with outlet foam according to an example of the present technology.

Figure 20:
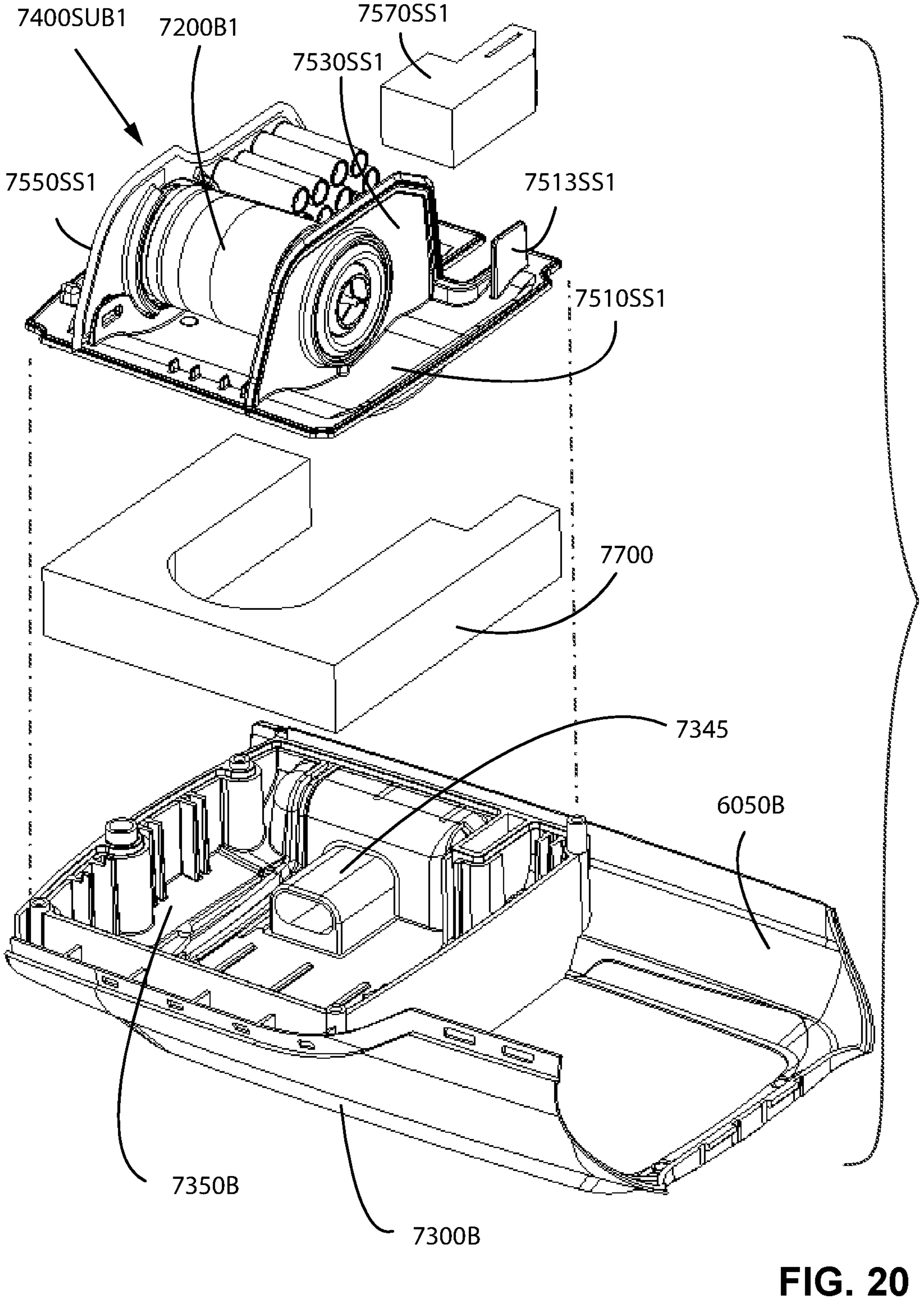

FIG. 20 is a perspective view showing assembly of inlet foam, outlet foam and a first blower sub-assembly to the bottom chassis of a chassis assembly according to an example of the present technology.

Figure 21:
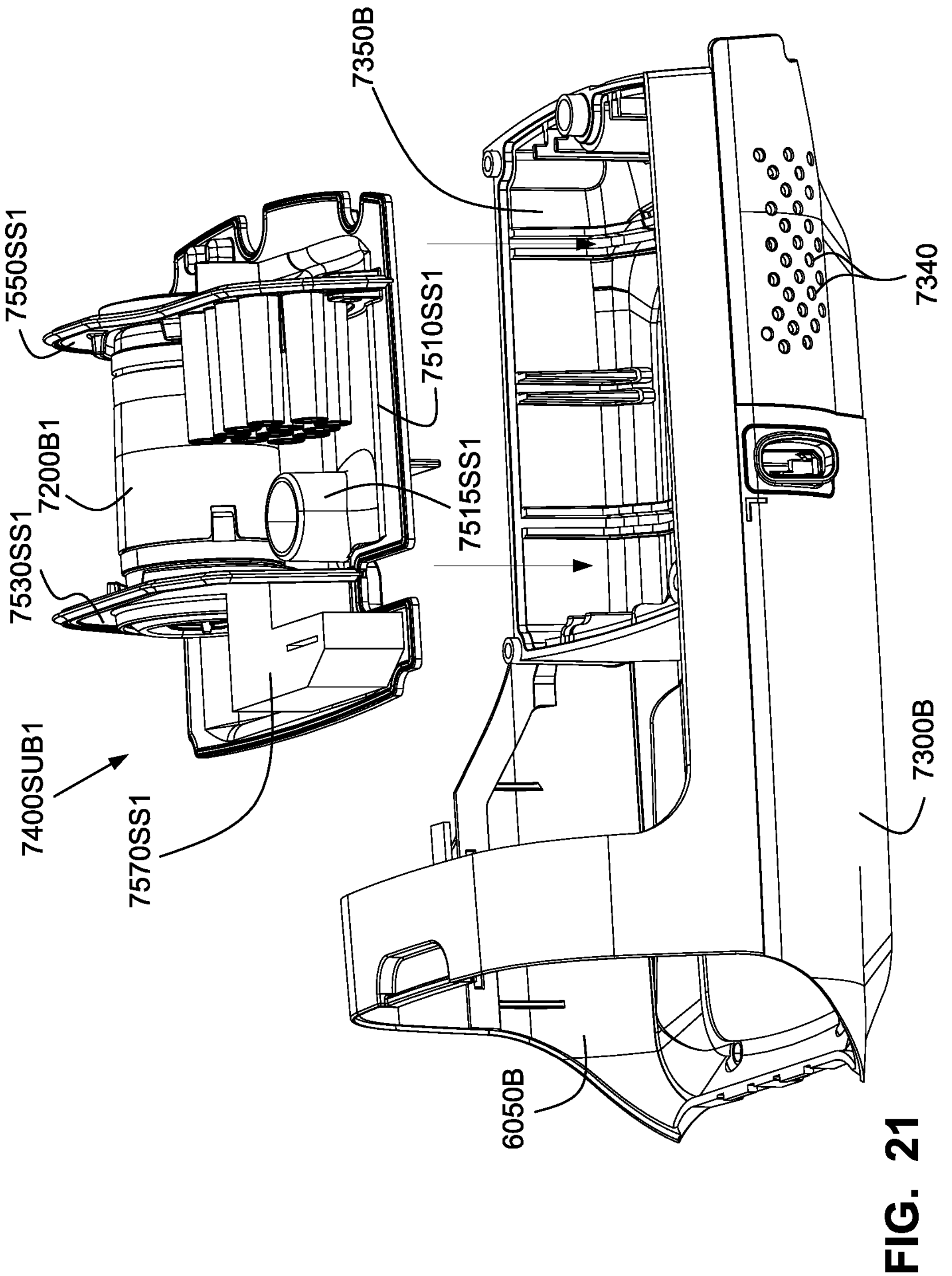

FIG. 21 is another perspective view showing assembly of a first blower sub-assembly to the bottom chassis of a chassis assembly according to an example of the present technology.

Figure 22:
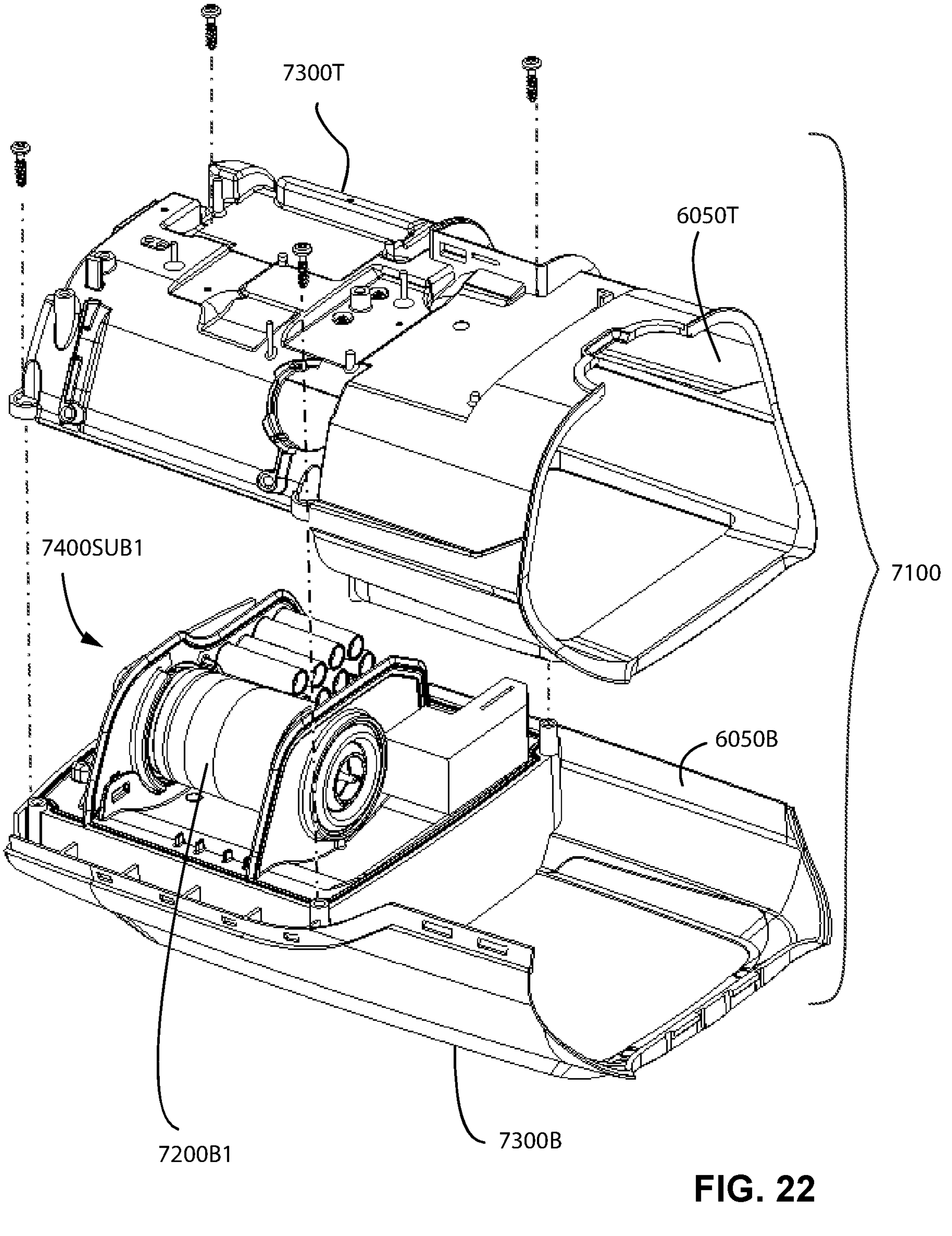

FIG. 22 is a perspective view showing assembly of a top chassis to a bottom chassis with a first blower sub-assembly according to an example of the present technology.

Figure 23:
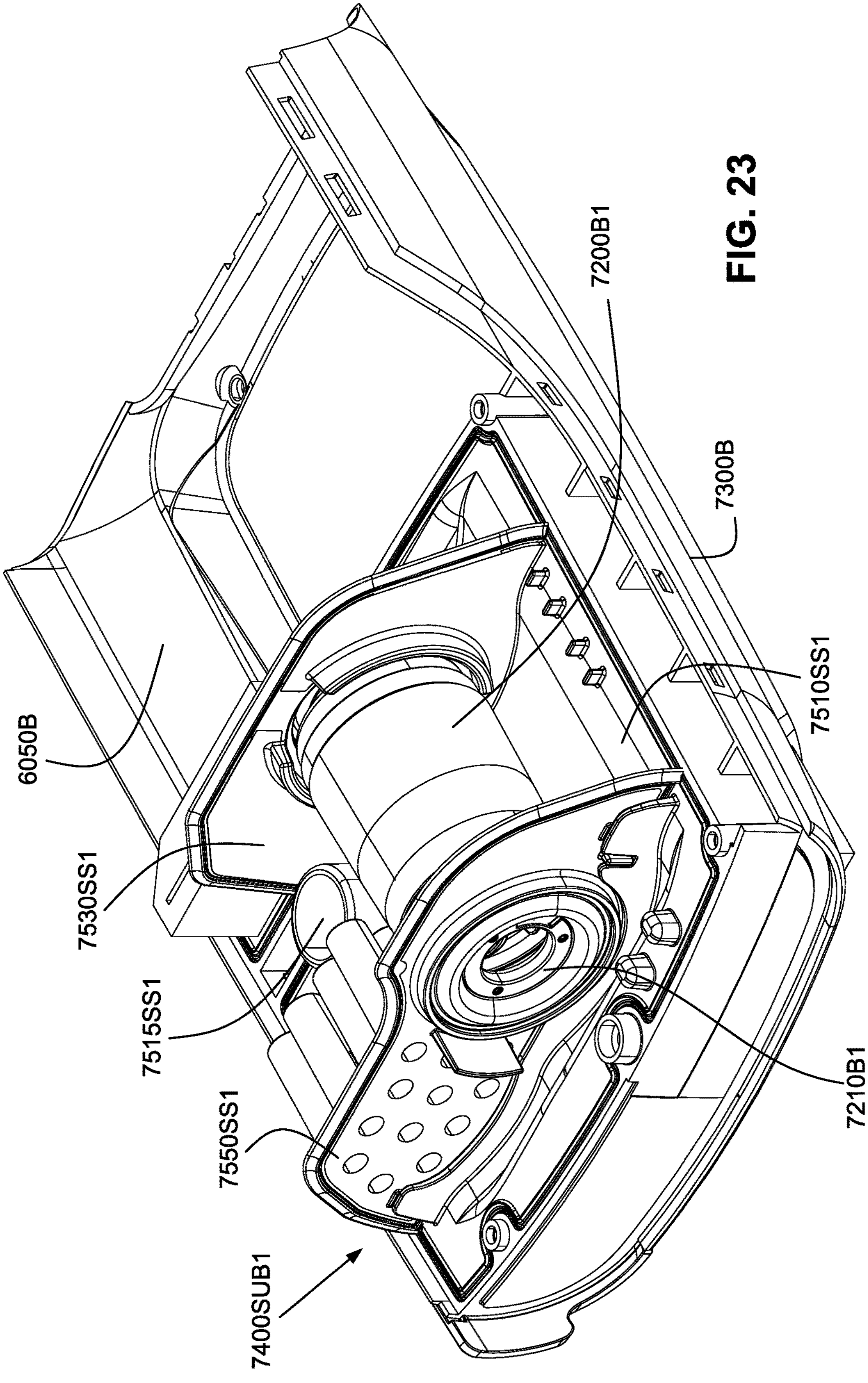

FIG. 23 is a perspective view showing a bottom chassis with a first blower sub-assembly according to an example of the present technology.

Figure 24:
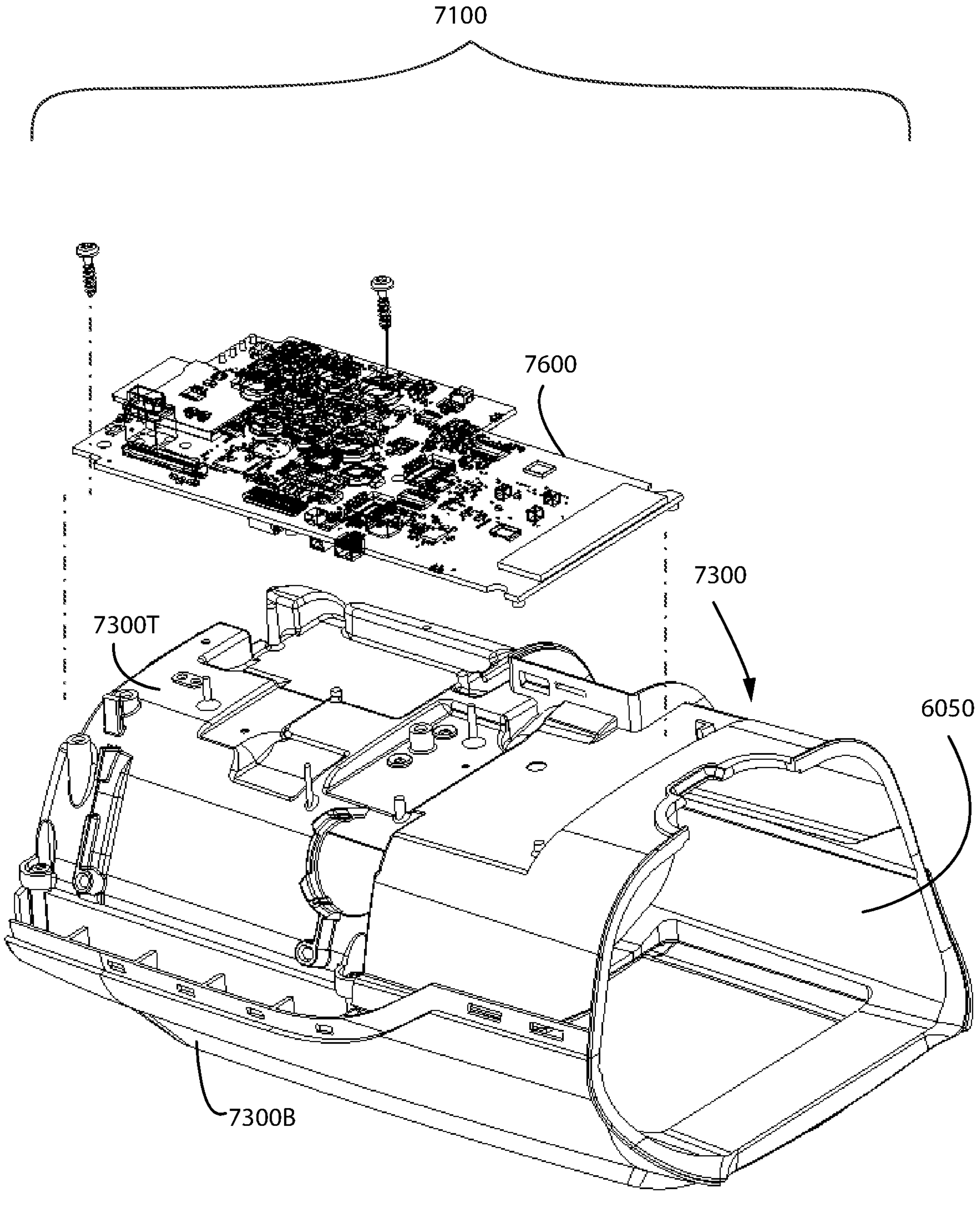

FIG. 24 is a perspective view showing assembly of a PCBA to a chassis assembly according to an example of the present technology.

Figure 25:
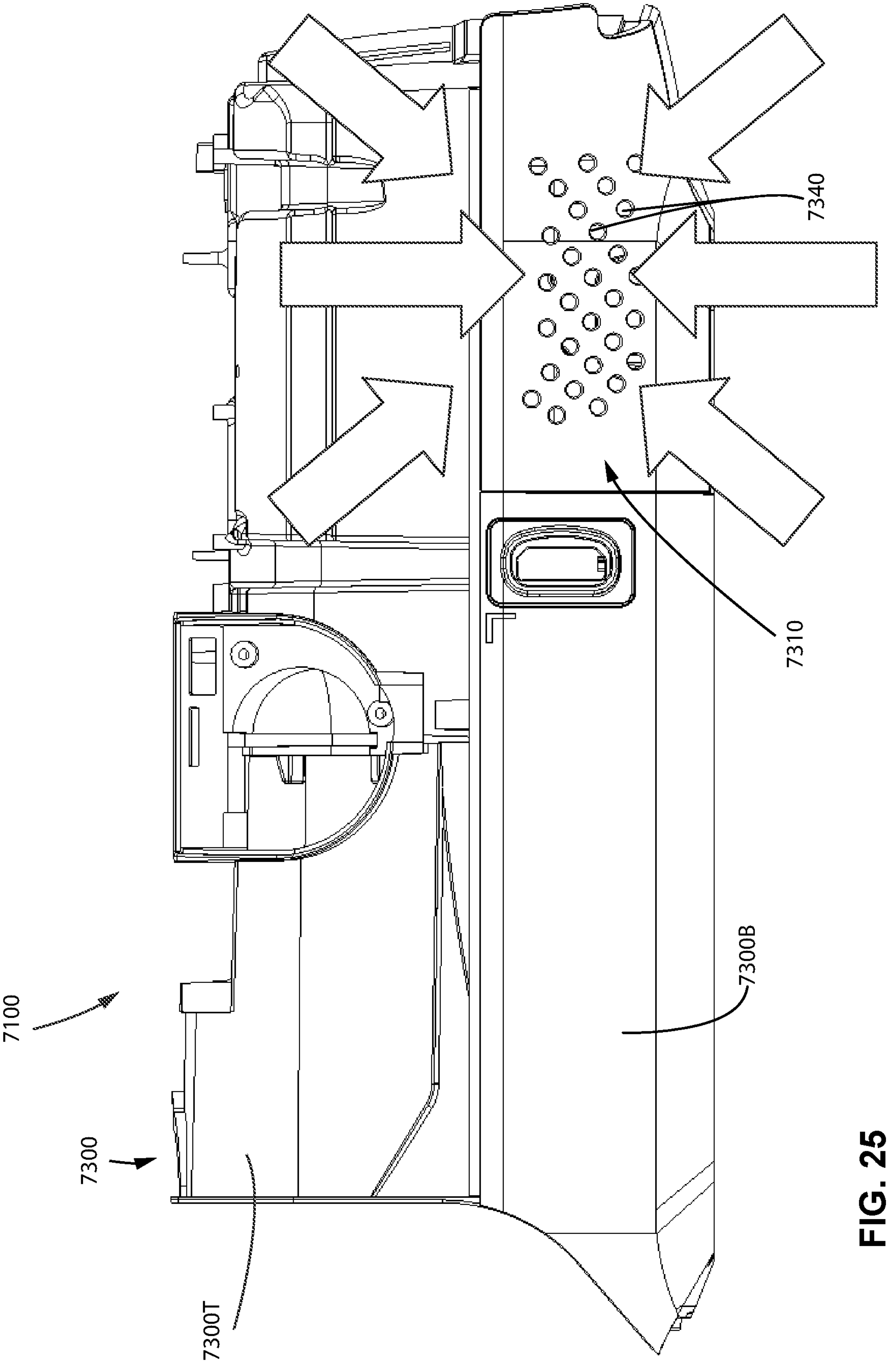

FIG. 25 is a side view showing air entering a pneumatic block via inlet openings according to an example of the present technology.

Figure 26:
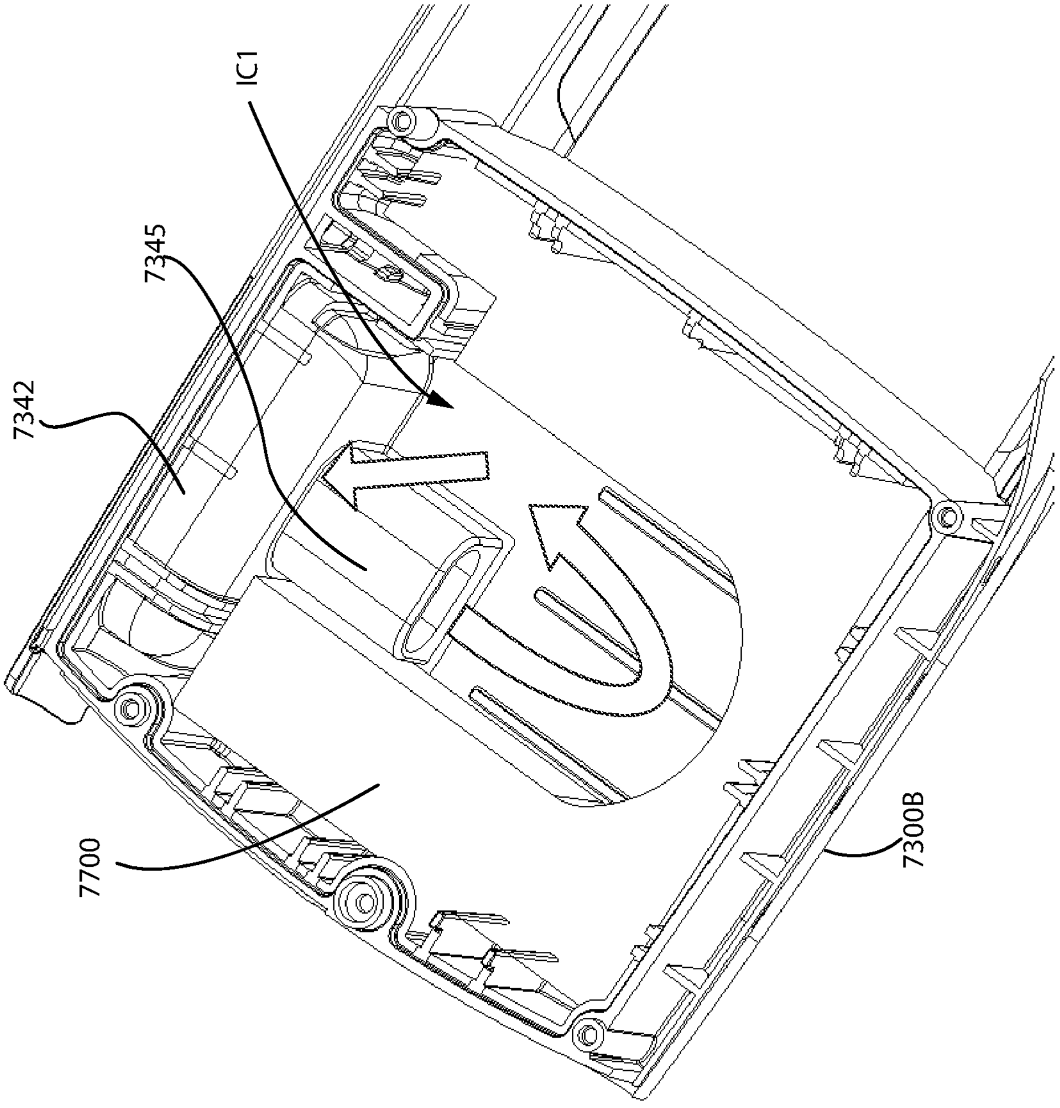

FIG. 26 is a cross-sectional view showing air circulating within a first inlet muffler chamber of a pneumatic block according to an example of the present technology.

Figure 27:
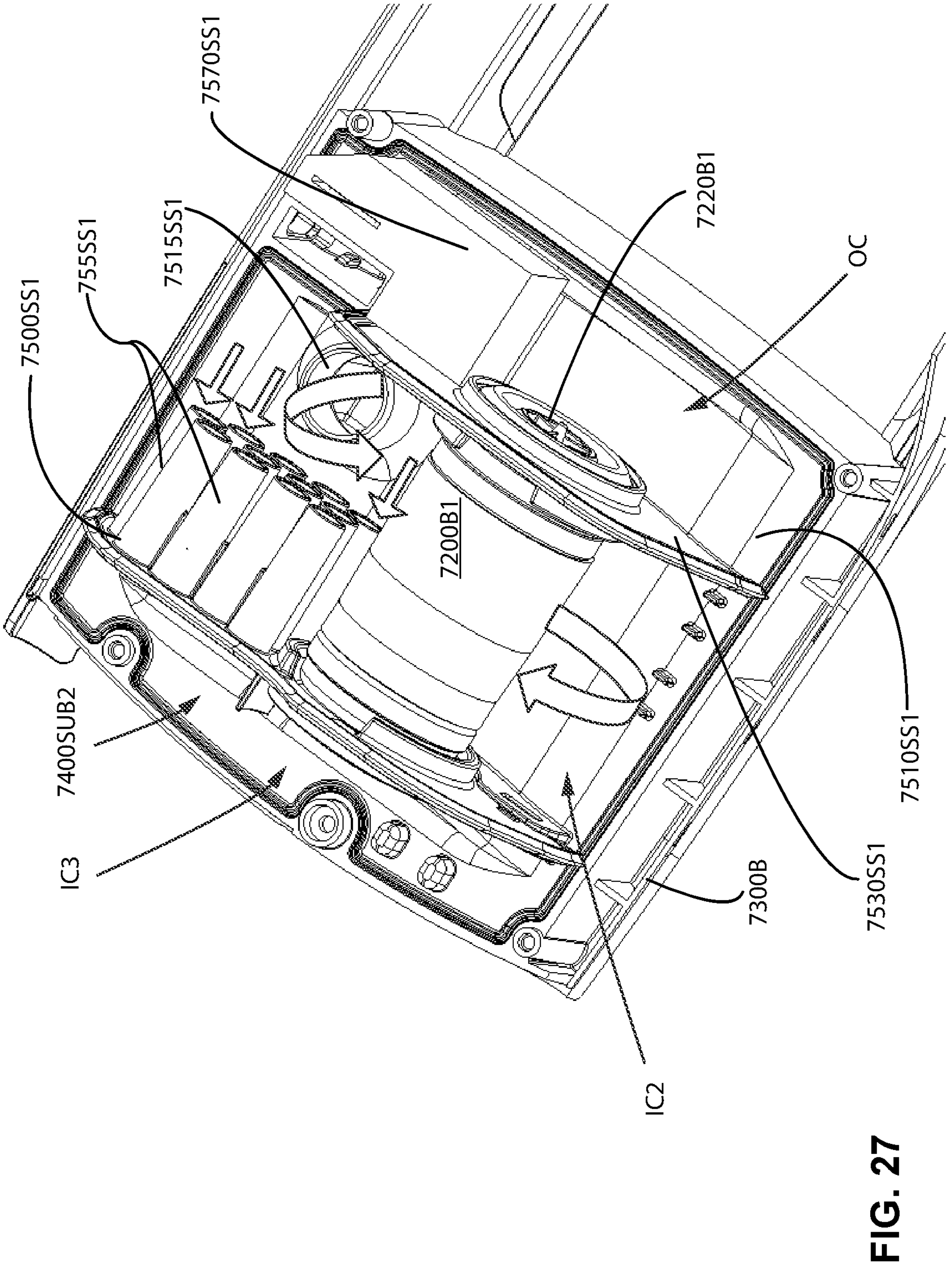

FIG. 27 is a cross-sectional view showing air circulating within a second inlet muffler chamber of a pneumatic block according to an example of the present technology.

Figure 28:
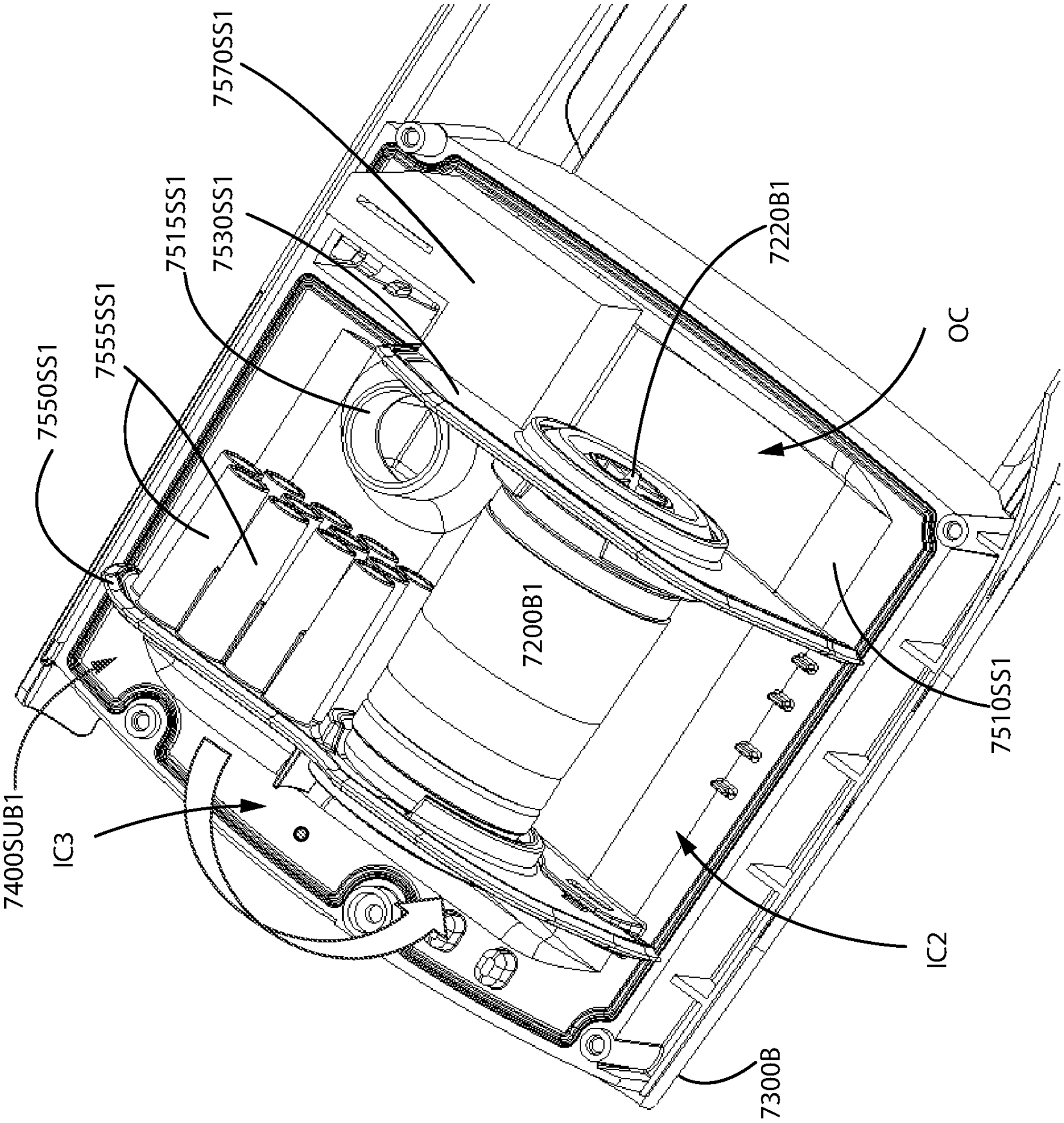

FIG. 28 is a cross-sectional view showing air circulating within a third inlet muffler chamber of a pneumatic block according to an example of the present technology.

Figure 29:
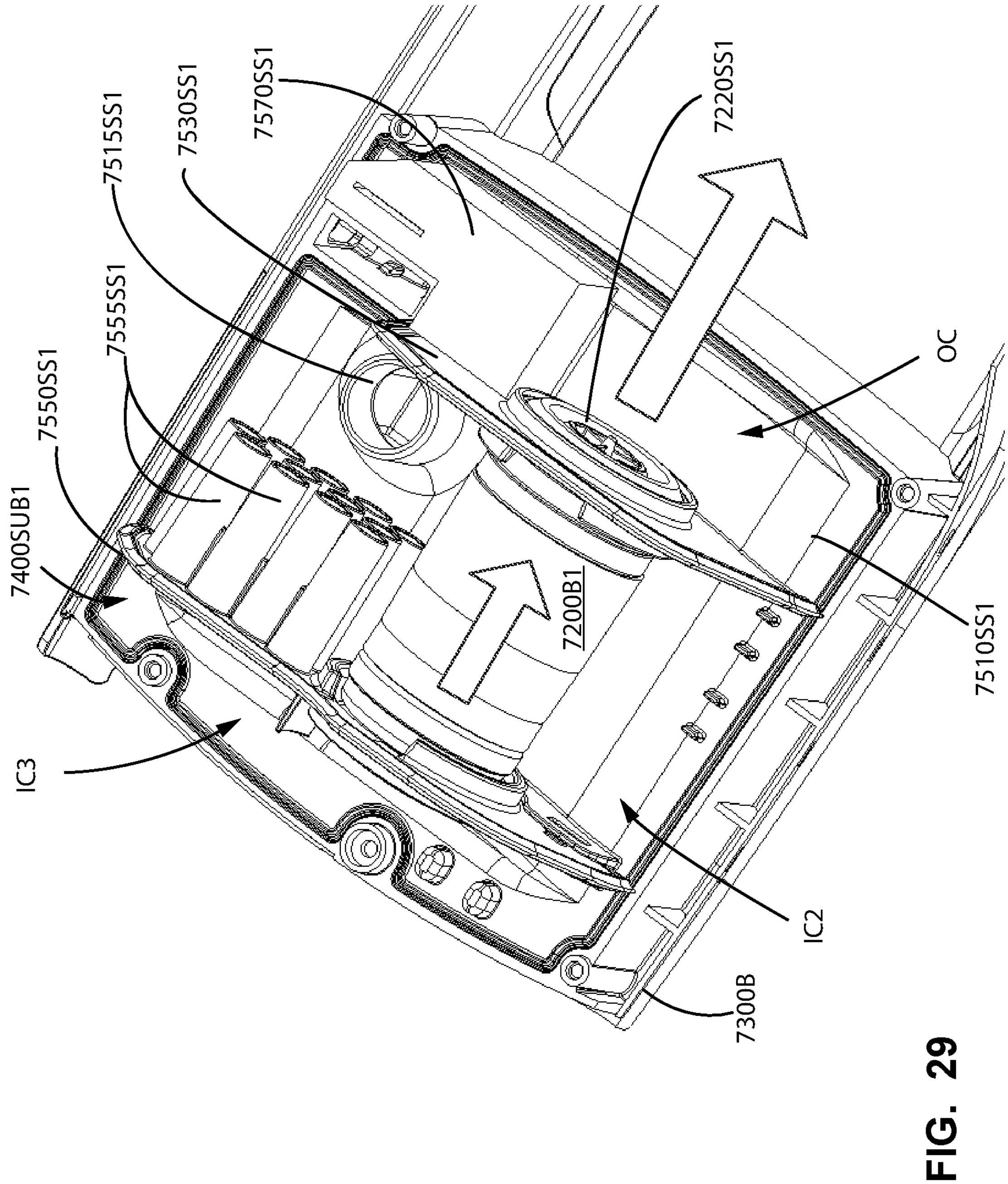

FIG. 29 is a cross-sectional view showing air passing through a blower, and entering and exiting an outlet chamber of a pneumatic block according to an example of the present technology.

Figure 30:
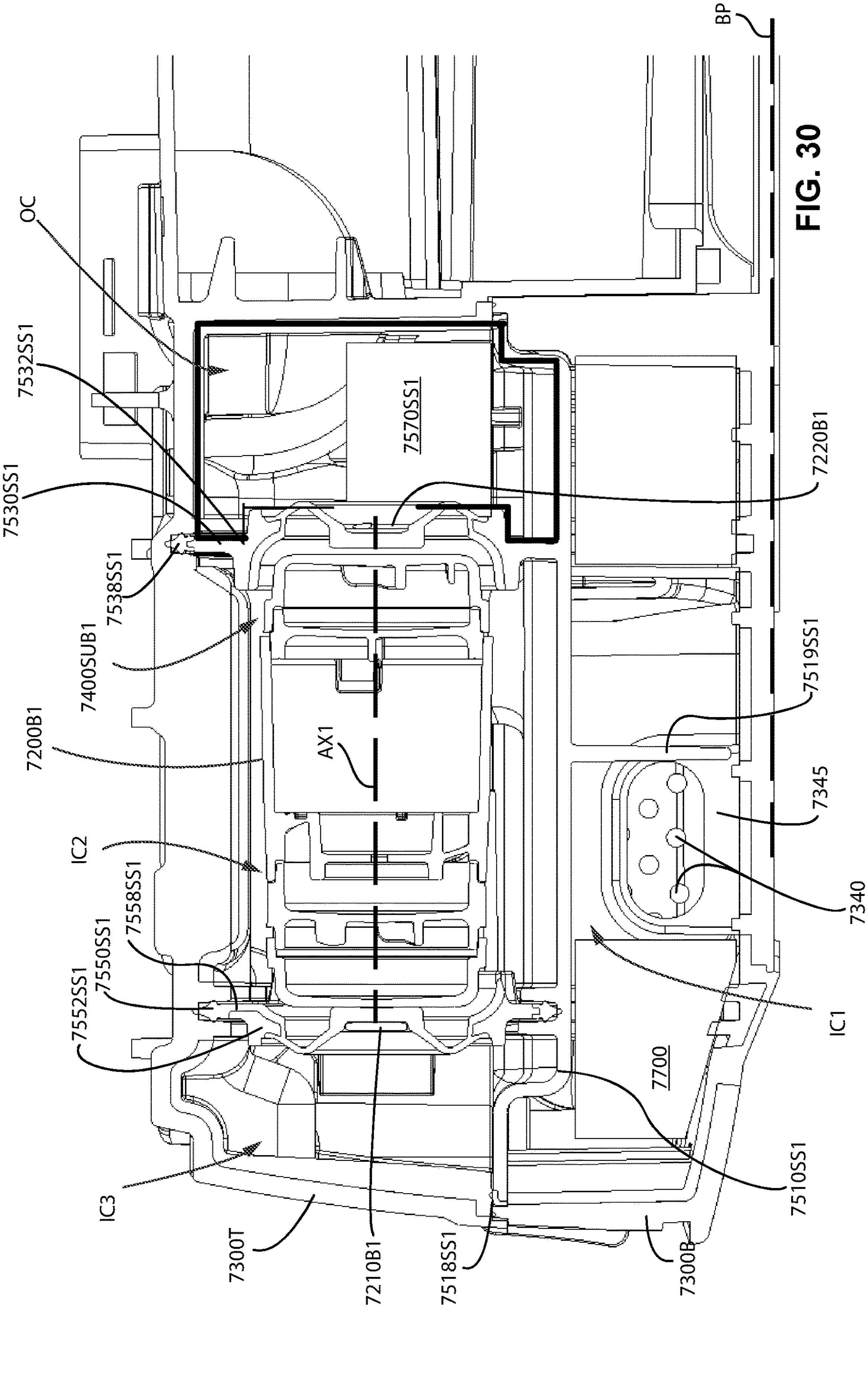

FIG. 30 is a cross-sectional view of a complete pneumatic block including first blower sub-assembly and highlighted outlet chamber according to an example of the present technology.

Figure 31:
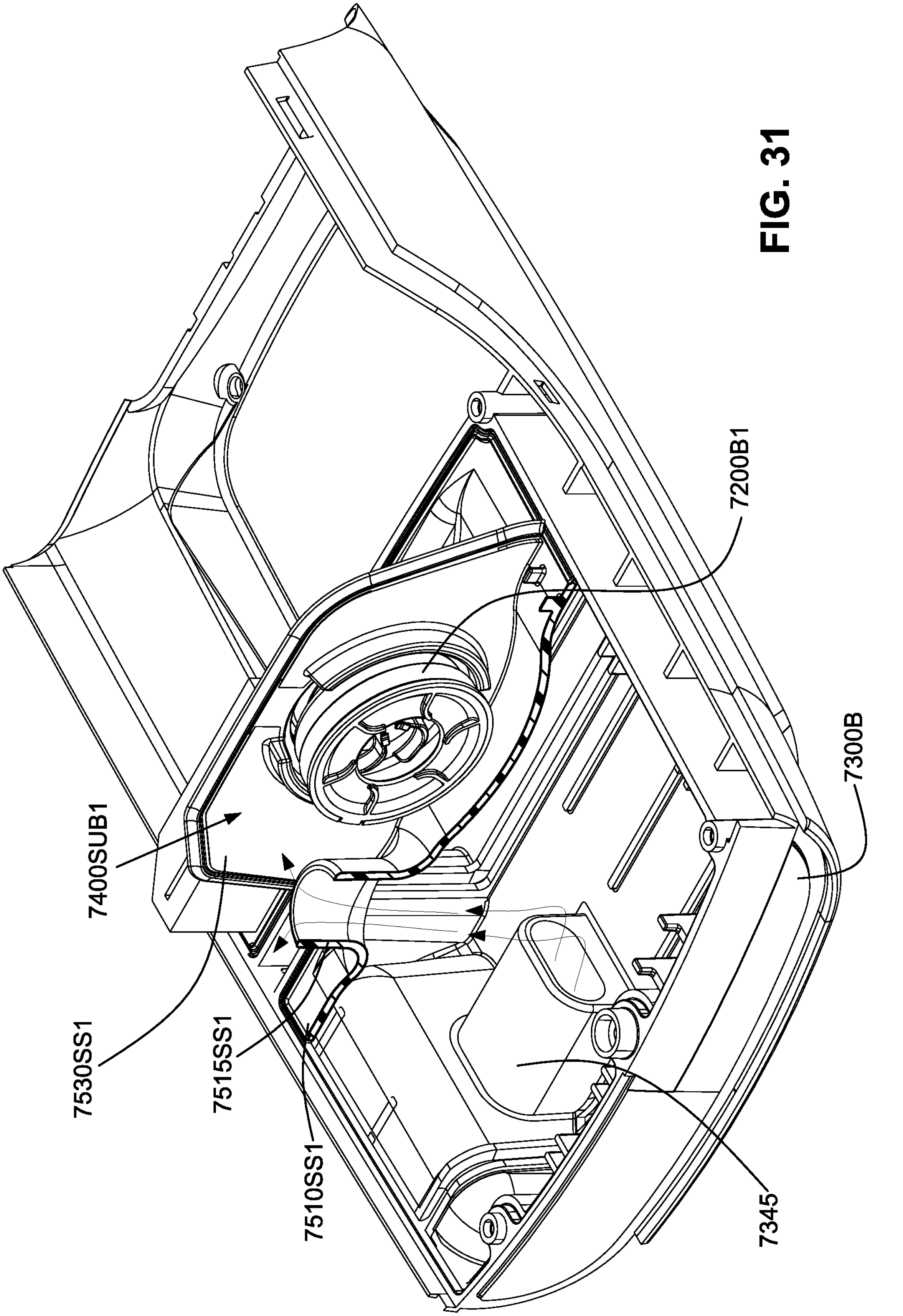

FIG. 31 is another cross-sectional view of a complete pneumatic block including first blower sub-assembly according to an example of the present technology.

Figure 32:
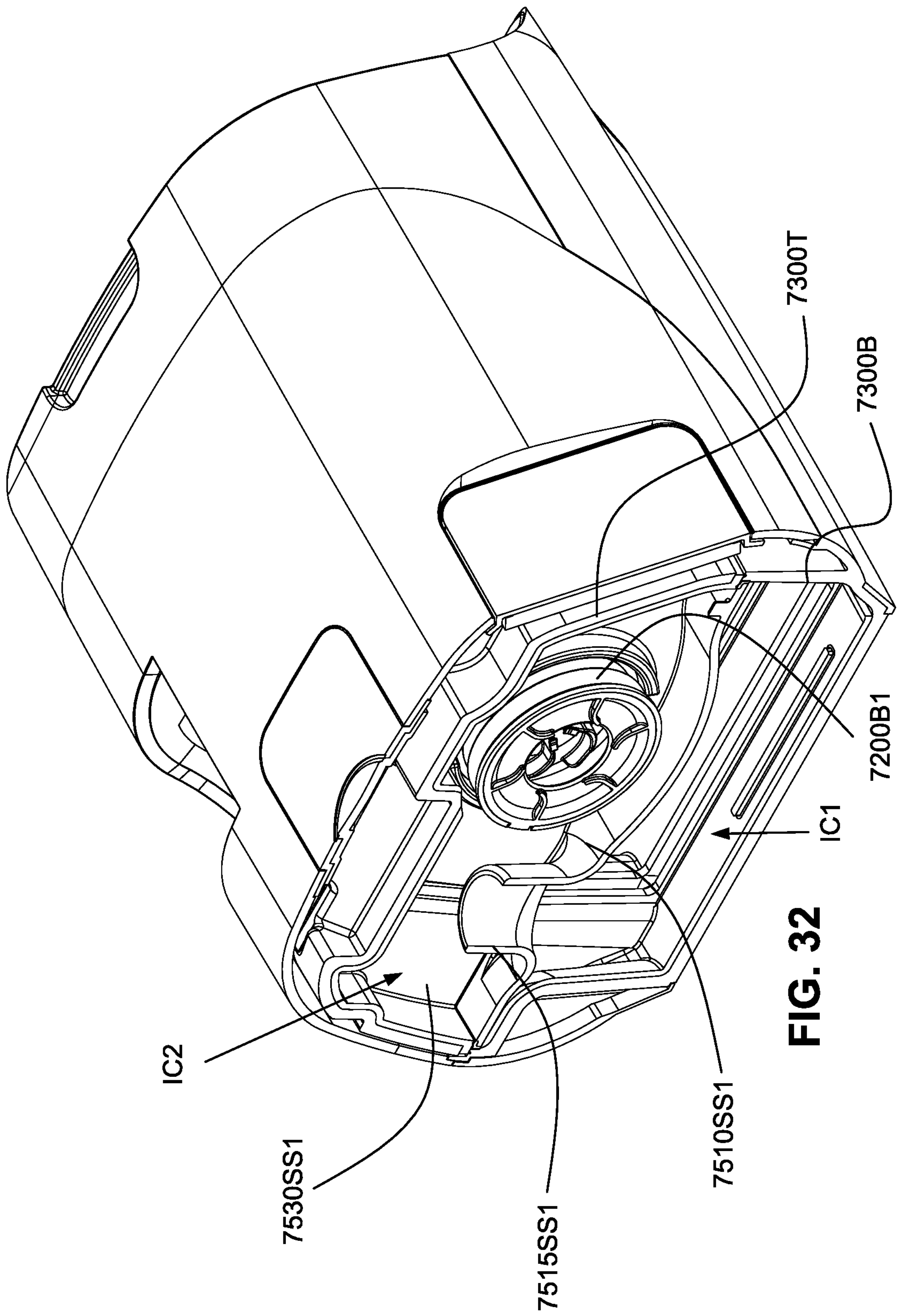

FIG. 32 is another cross-sectional view of a complete pneumatic block including first blower sub-assembly according to an example of the present technology.

Figure 33:
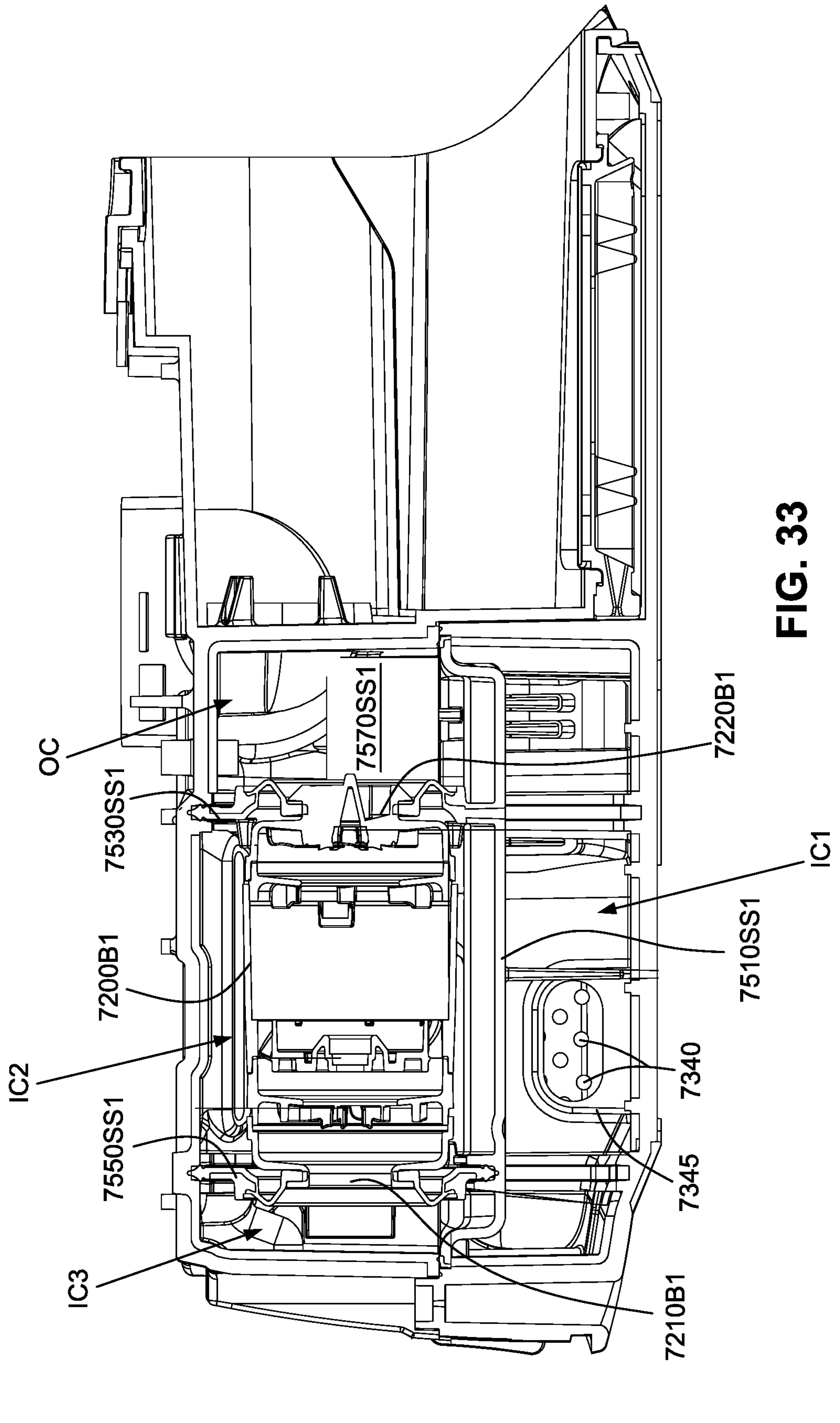

FIG. 33 is another cross-sectional view of a complete pneumatic block including first blower sub-assembly according to an example of the present technology.

Figure 34:
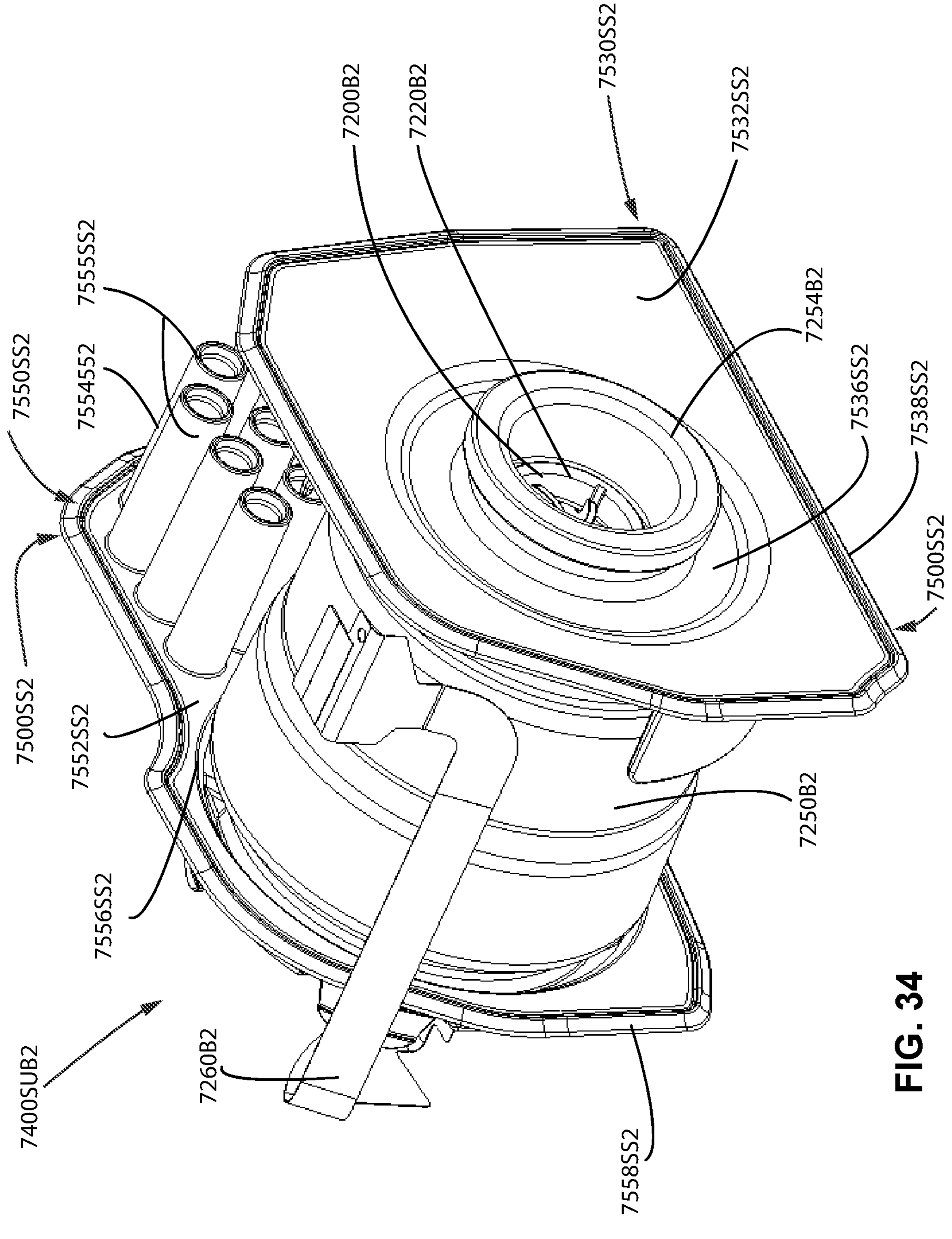

FIG. 34 is a perspective view of a second blower sub-assembly according to an example of the present technology.

Figure 35:
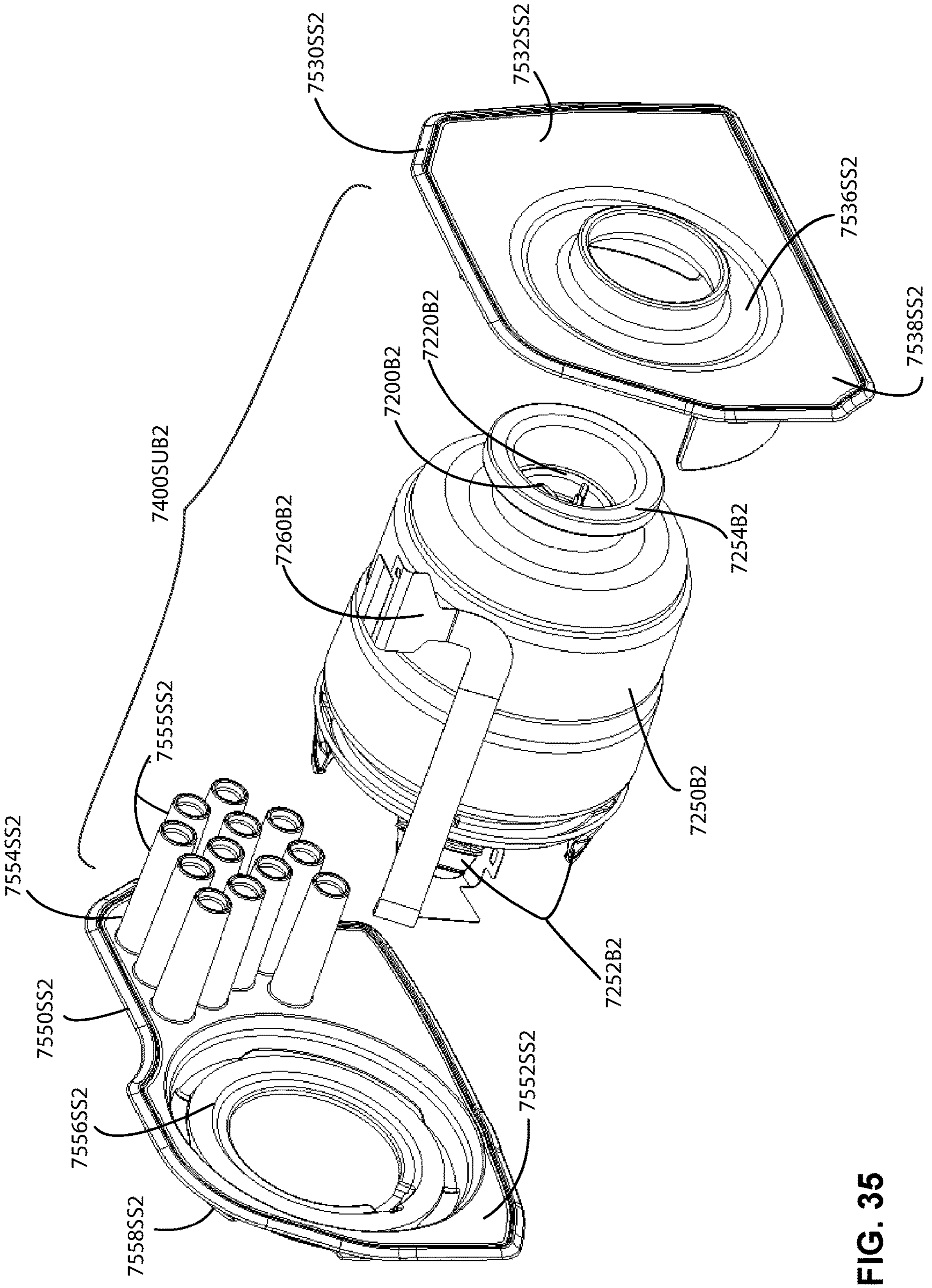

FIG. 35 is an exploded view of the second blower sub-assembly of FIG. 34.

Figure 36:
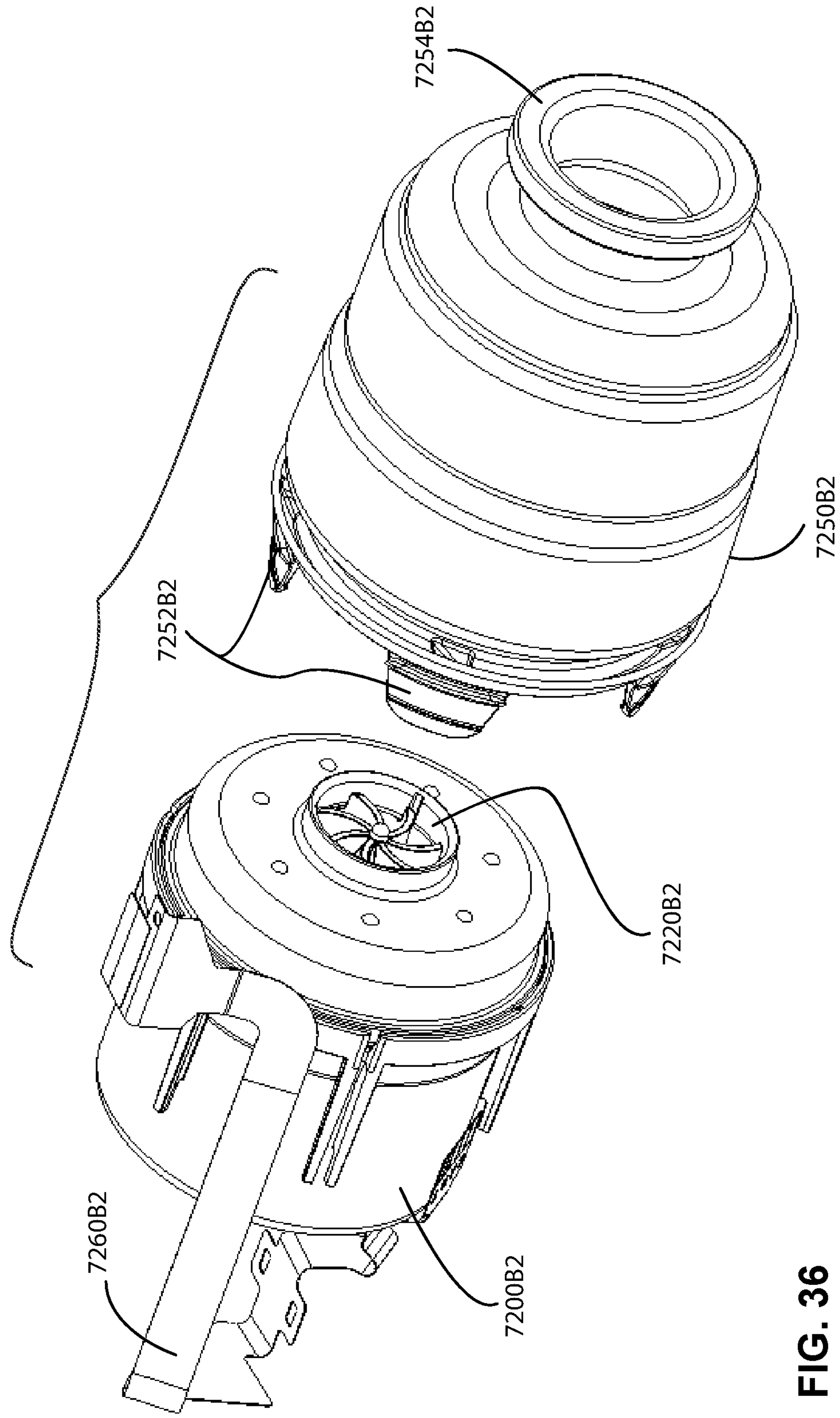

FIG. 36 is an exploded view of a blower and a suspension of the second blower sub-assembly according to an example of the present technology.

Figure 37:
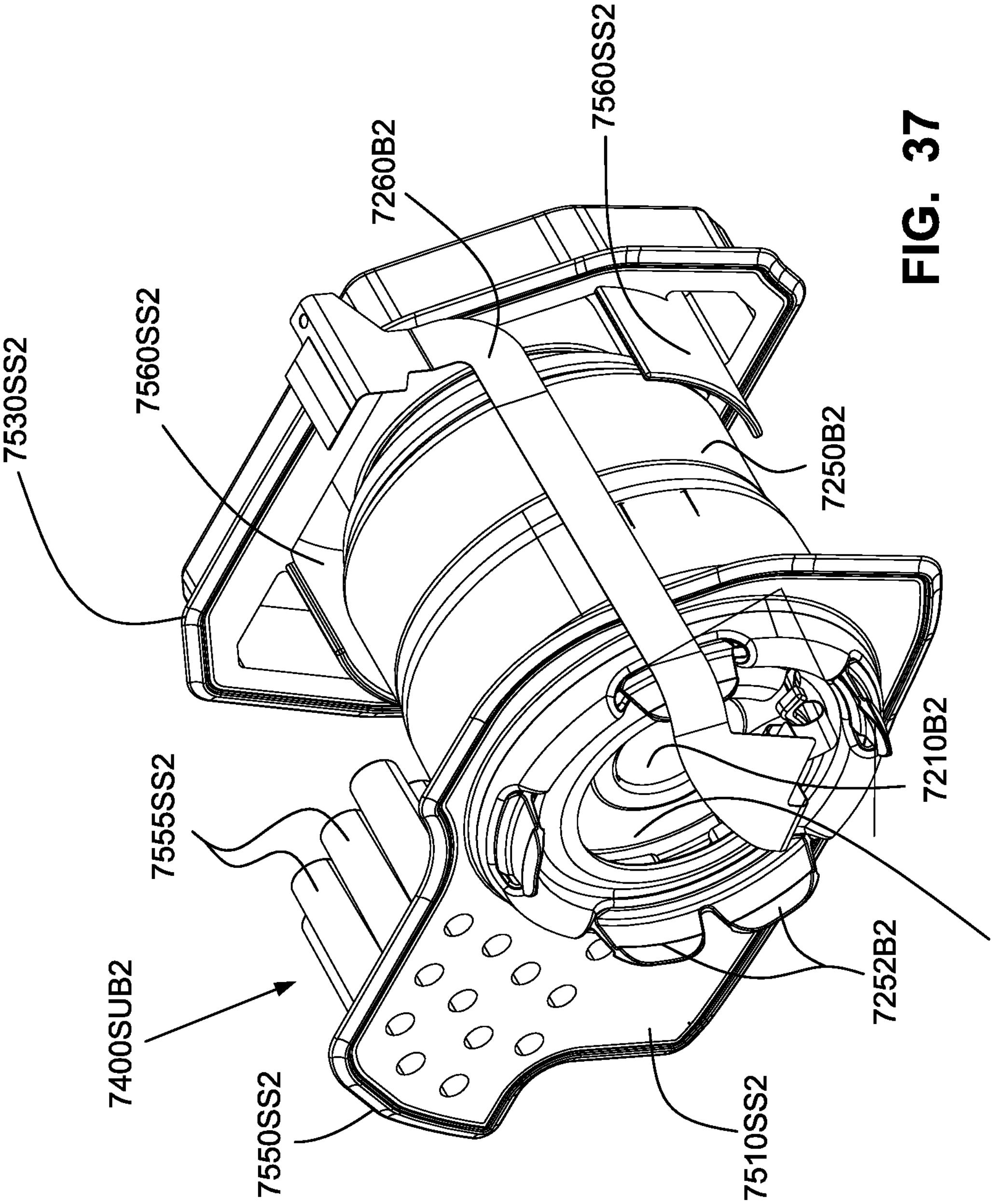

FIG. 37 is another perspective view of the second blower sub-assembly according to an example of the present technology.

Figure 38:
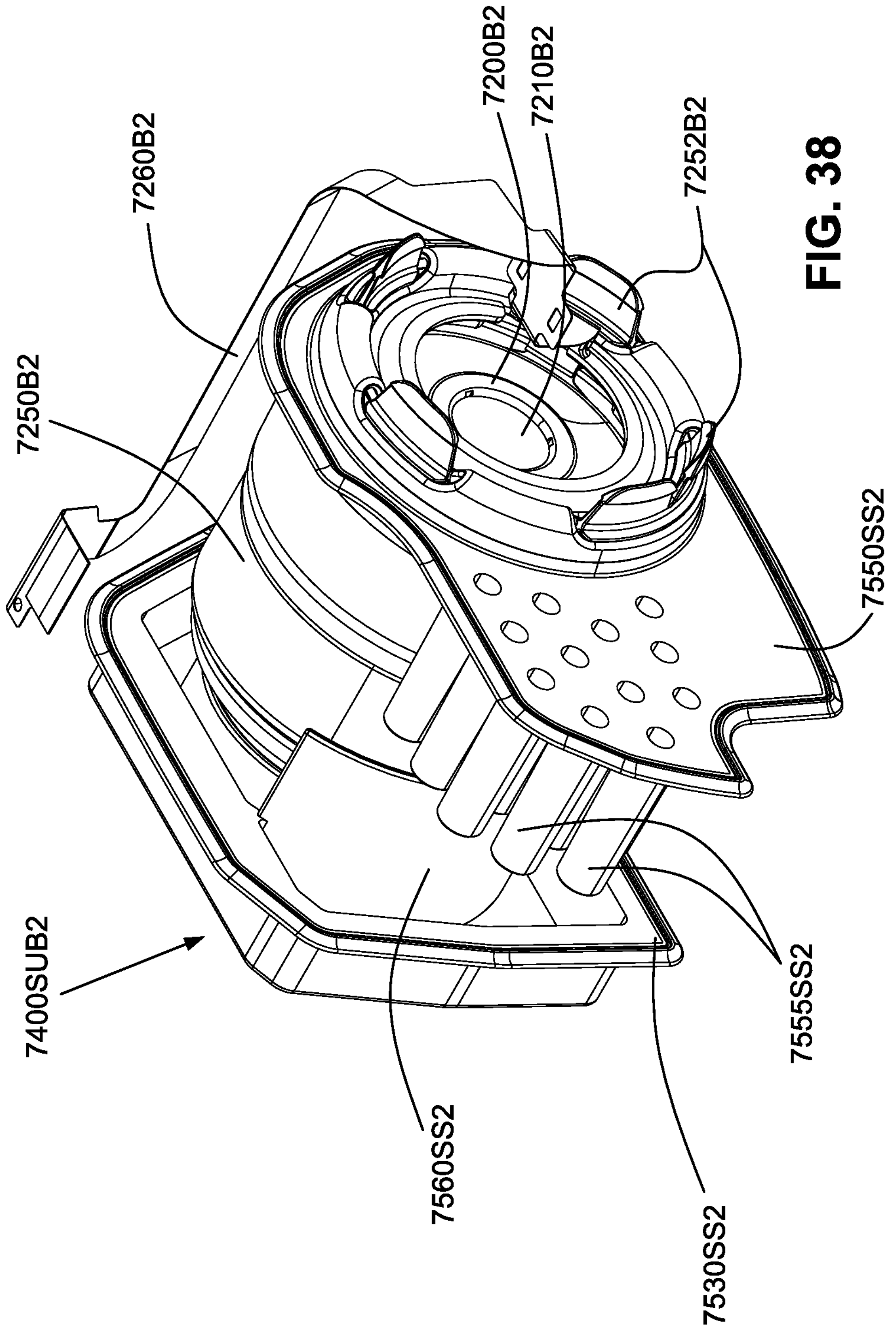

FIG. 38 is another perspective view of the second blower sub-assembly according to an example of the present technology.

Figure 39:
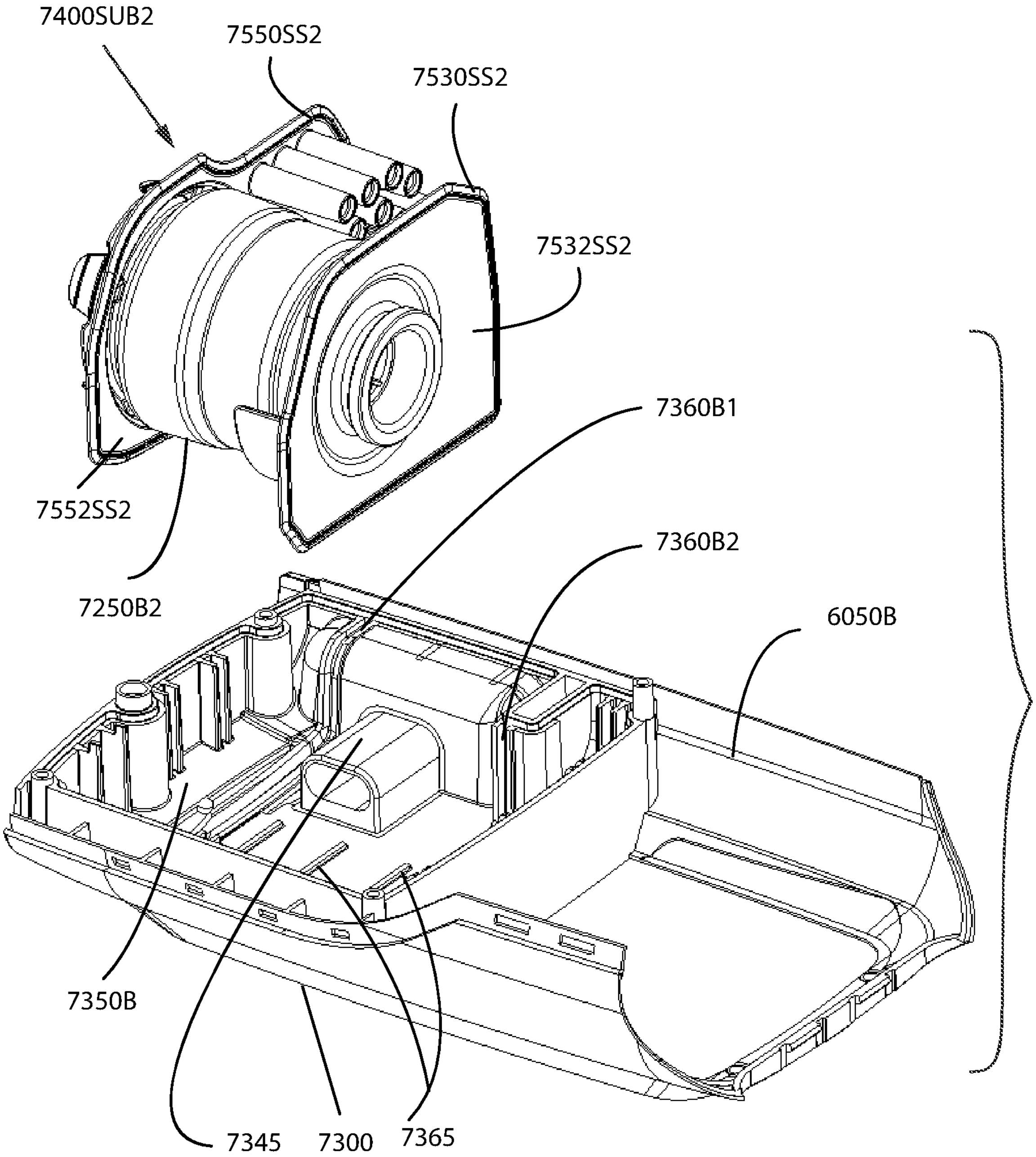

FIG. 39 is a perspective view showing assembly of a second blower sub-assembly to the bottom chassis of a chassis assembly according to an example of the present technology.

Figure 40:
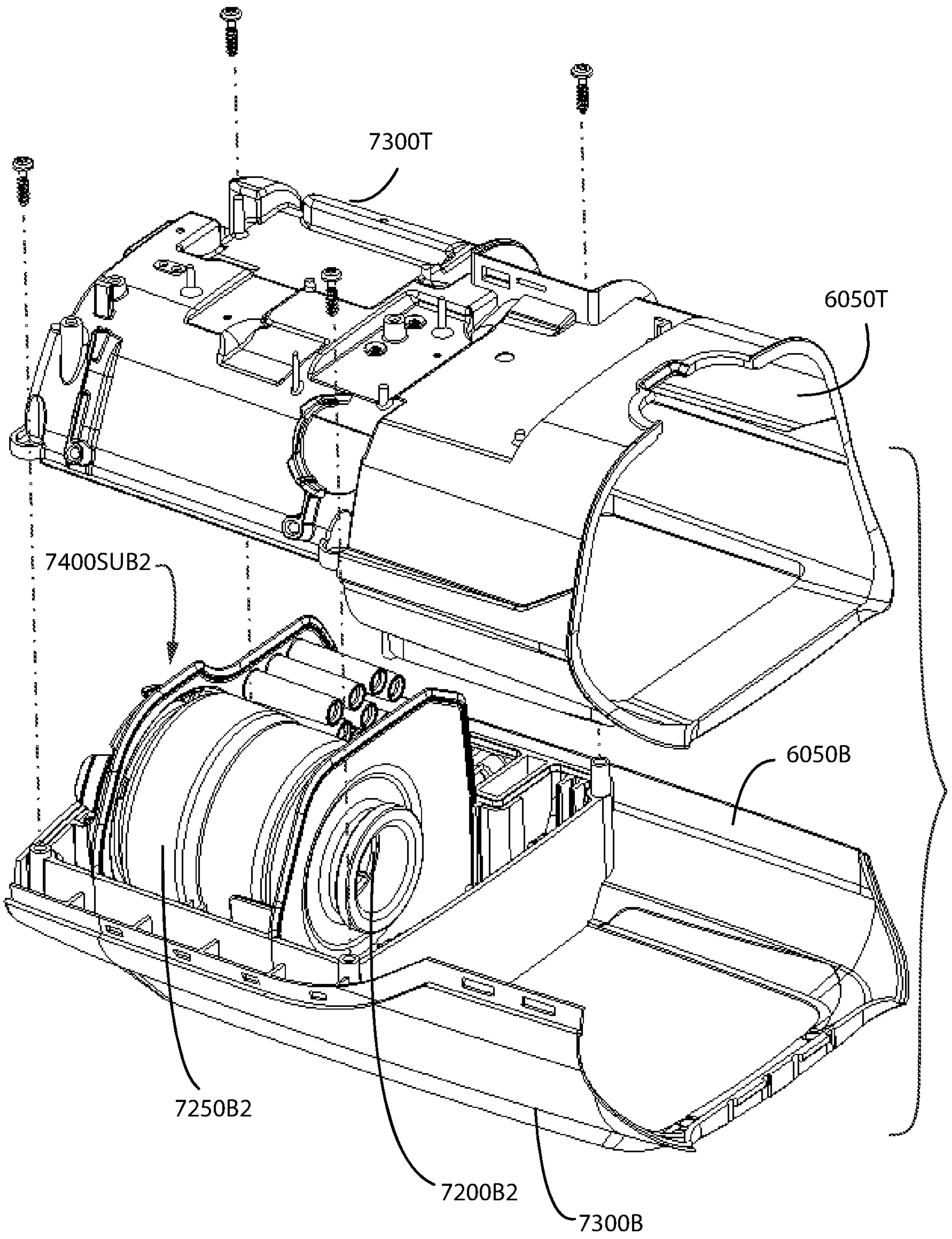

FIG. 40 is a perspective view showing assembly of a top chassis to a bottom chassis with a second blower sub-assembly according to an example of the present technology.

Figure 41:
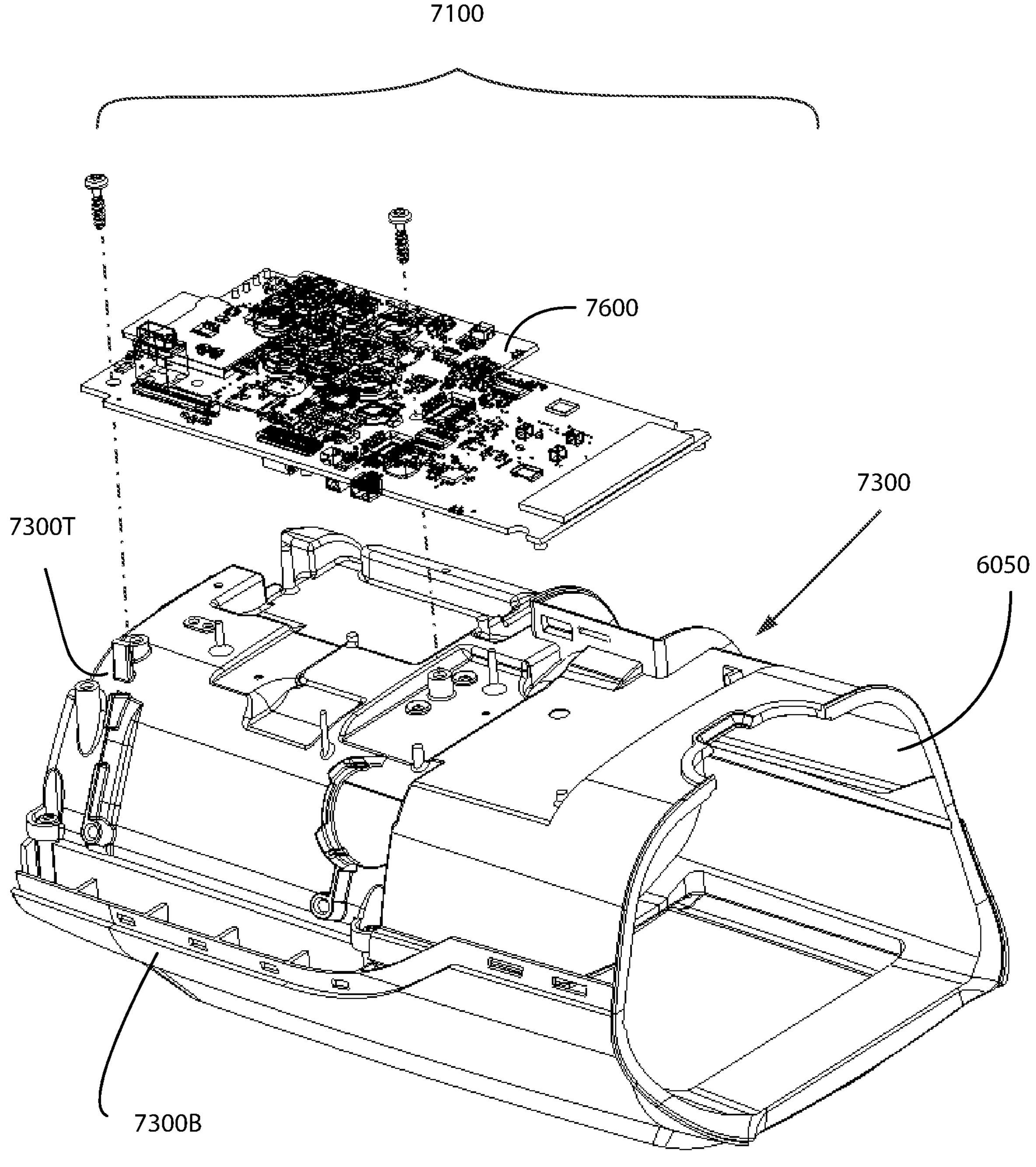

FIG. 41 is a perspective view showing assembly of a PCBA to a chassis assembly according to an example of the present technology.

Figure 42:
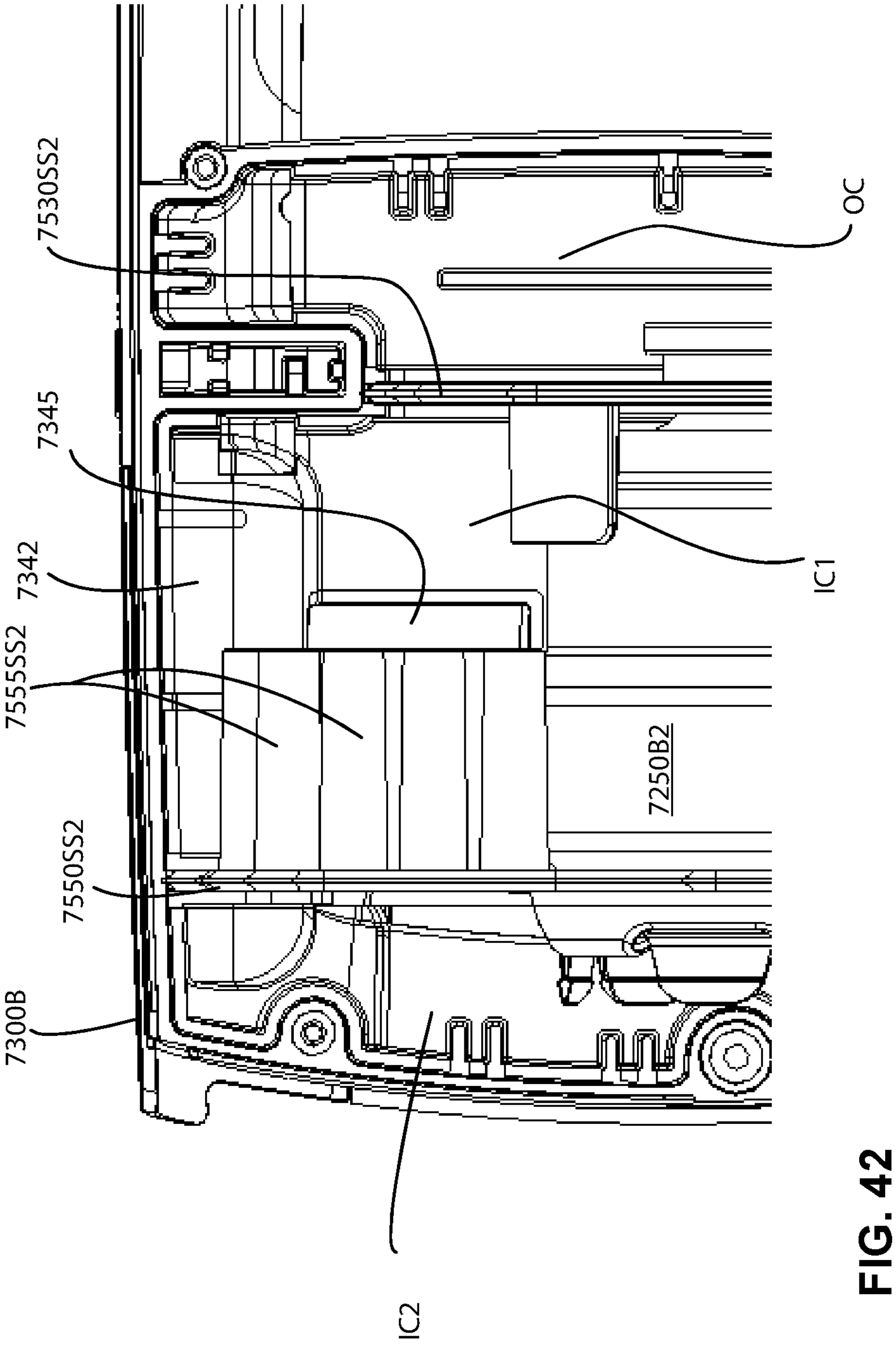

FIG. 42 is a cross-sectional view showing a complete pneumatic block including second blower sub-assembly according to an example of the present technology.

Figure 43:
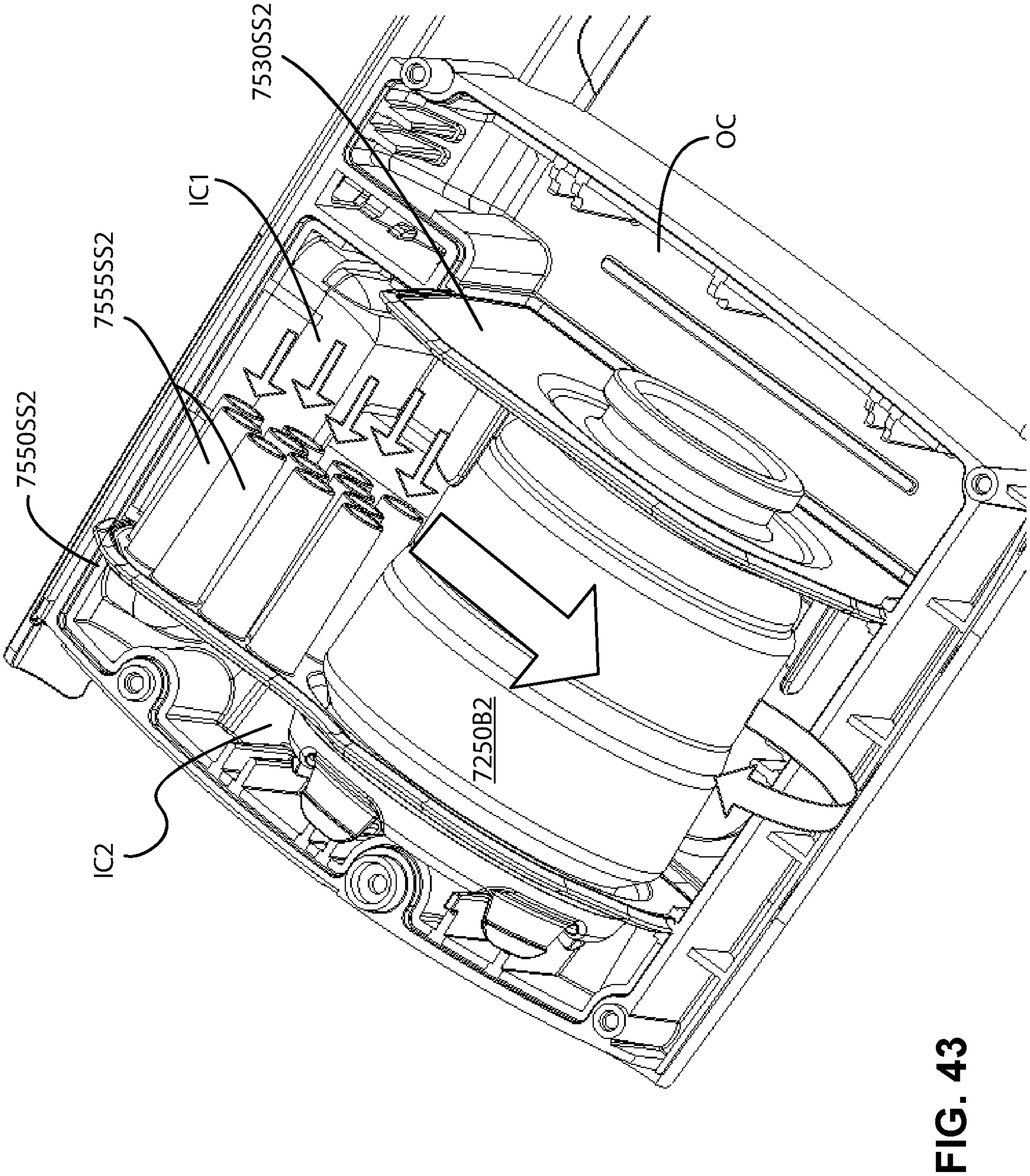

FIG. 43 is a cross-sectional view showing air circulating within a first inlet muffler chamber of a pneumatic block according to an example of the present technology.

Figure 44:
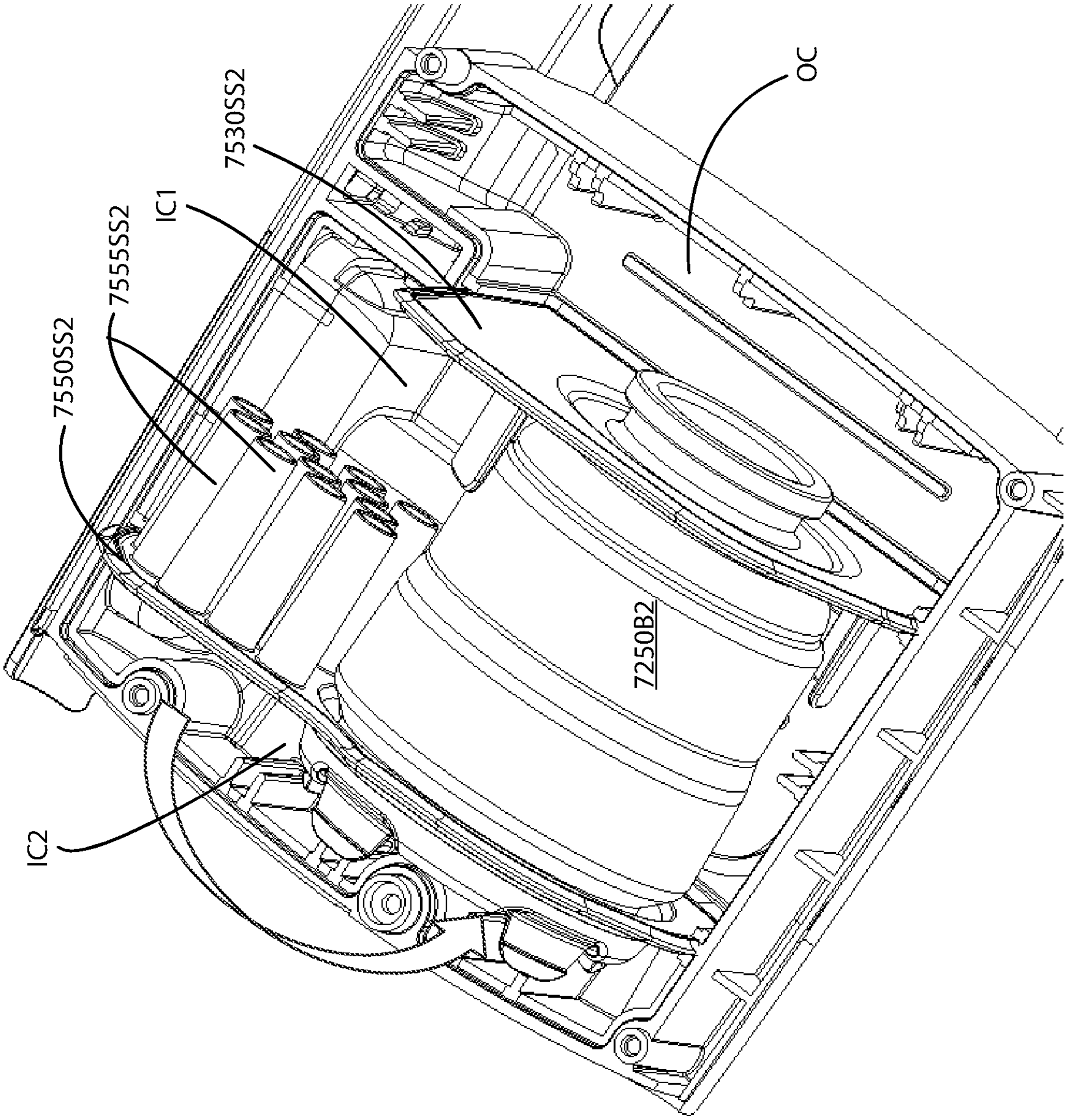

FIG. 44 is a cross-sectional view showing air circulating within a second inlet muffler chamber of a pneumatic block according to an example of the present technology.

Figure 45:
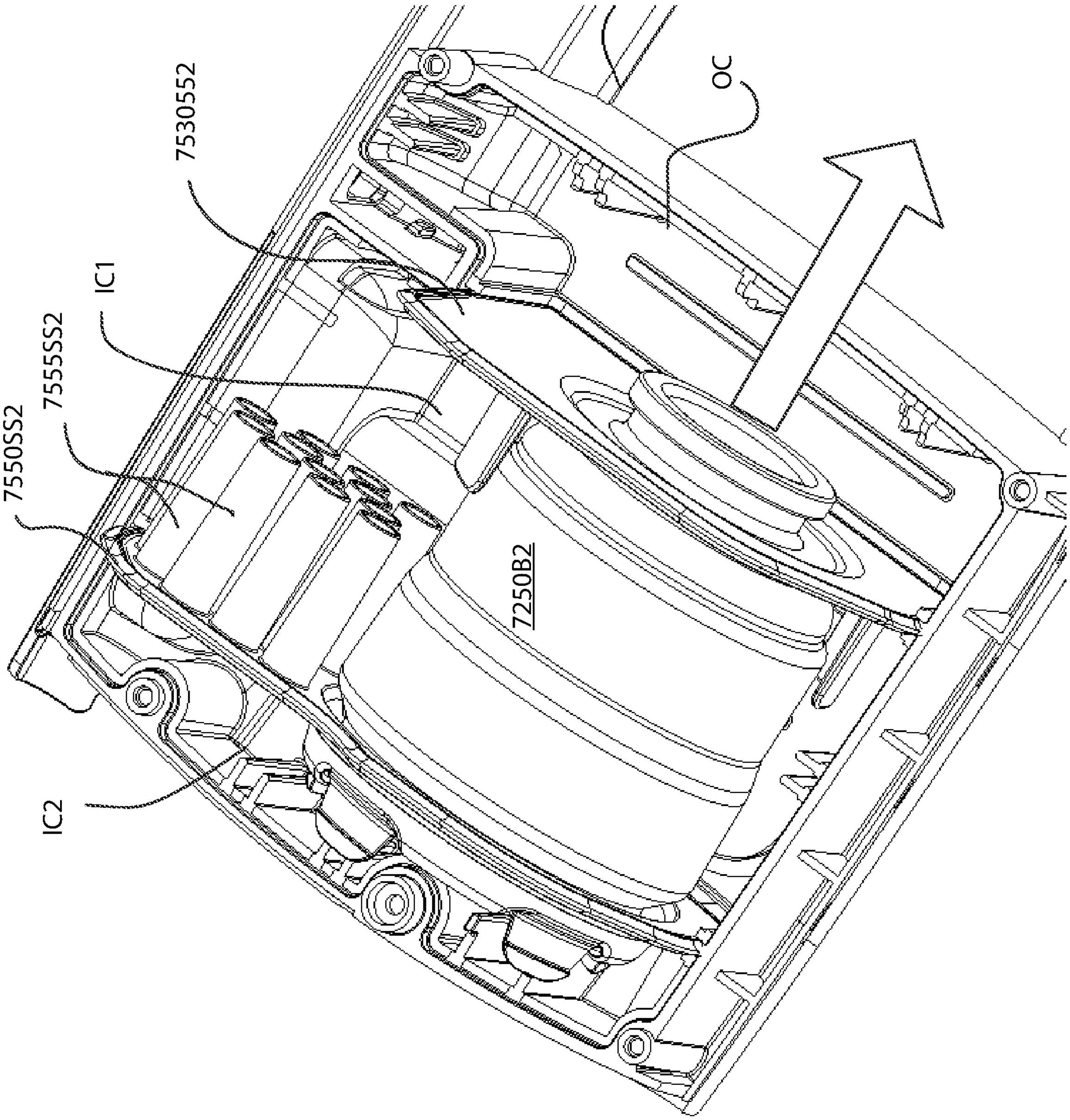

FIG. 45 is a cross-sectional view showing air passing through a blower, and entering and exiting an outlet chamber of a pneumatic block according to an example of the present technology.

Figure 46:
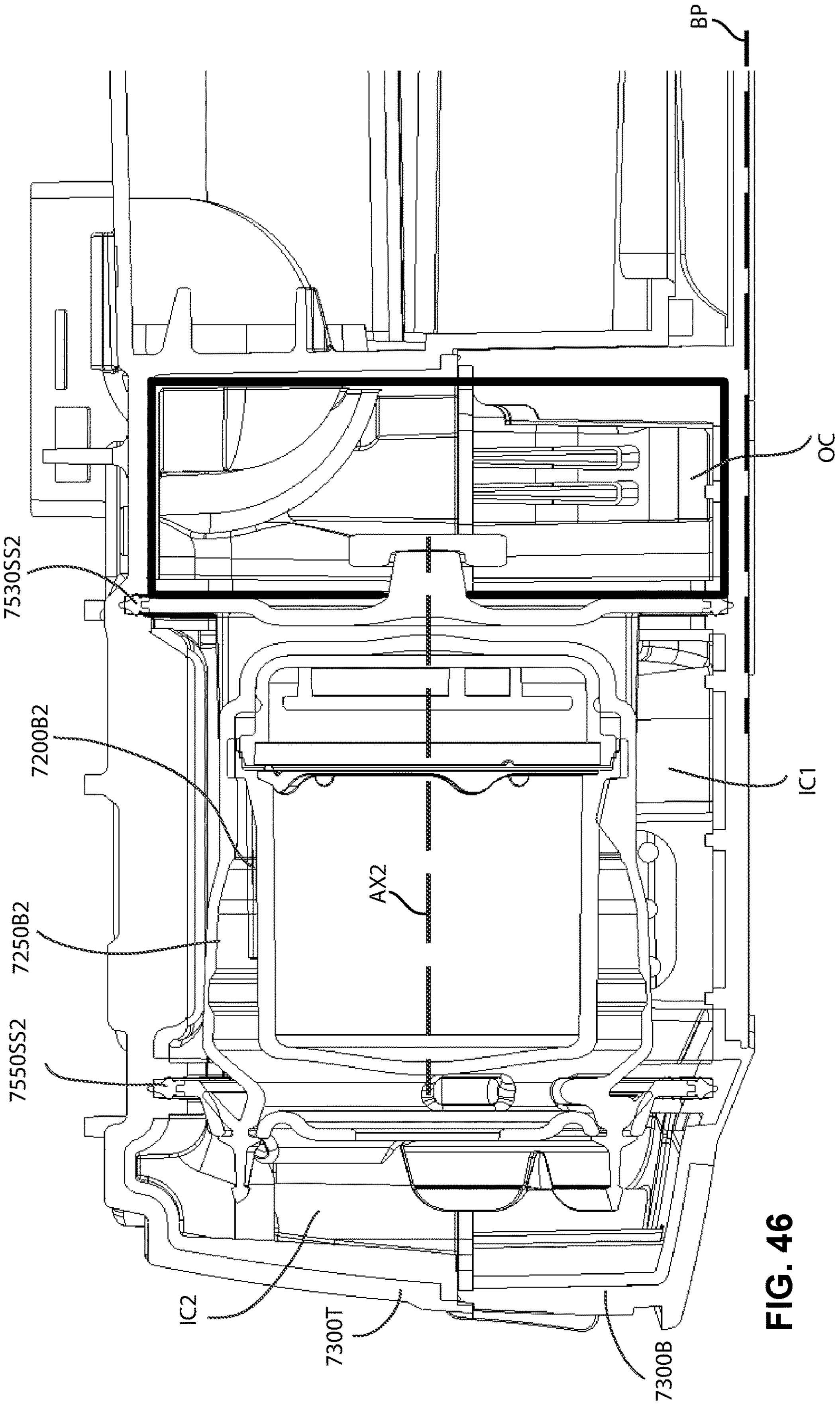

FIG. 46 is a cross-sectional view of a complete pneumatic block including second blower sub-assembly and highlighted outlet chamber according to an example of the present technology.

Figure 47:
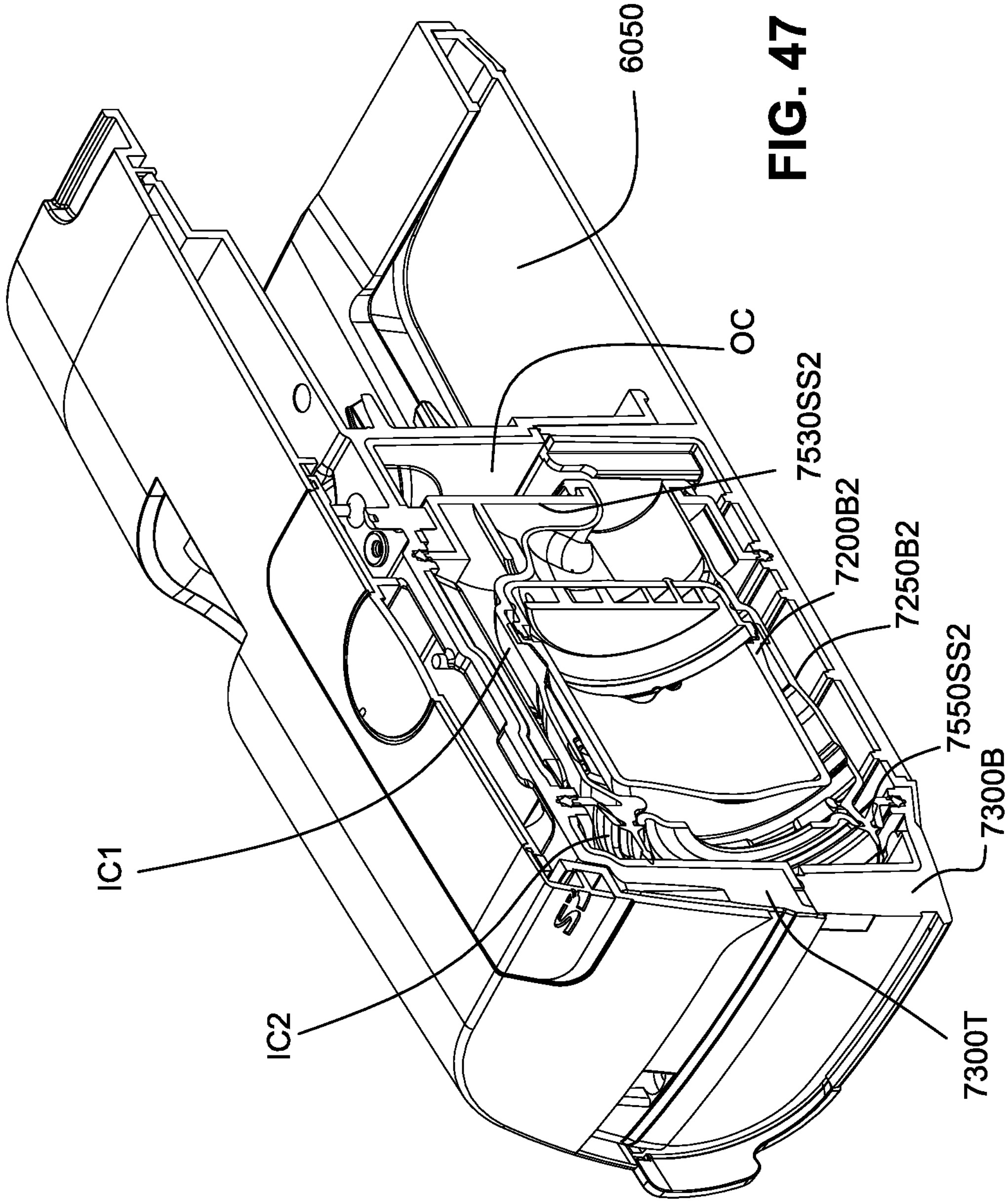

FIG. 47 is another cross-sectional view of a complete pneumatic block including second blower sub-assembly according to an example of the present technology.

Figure 48:
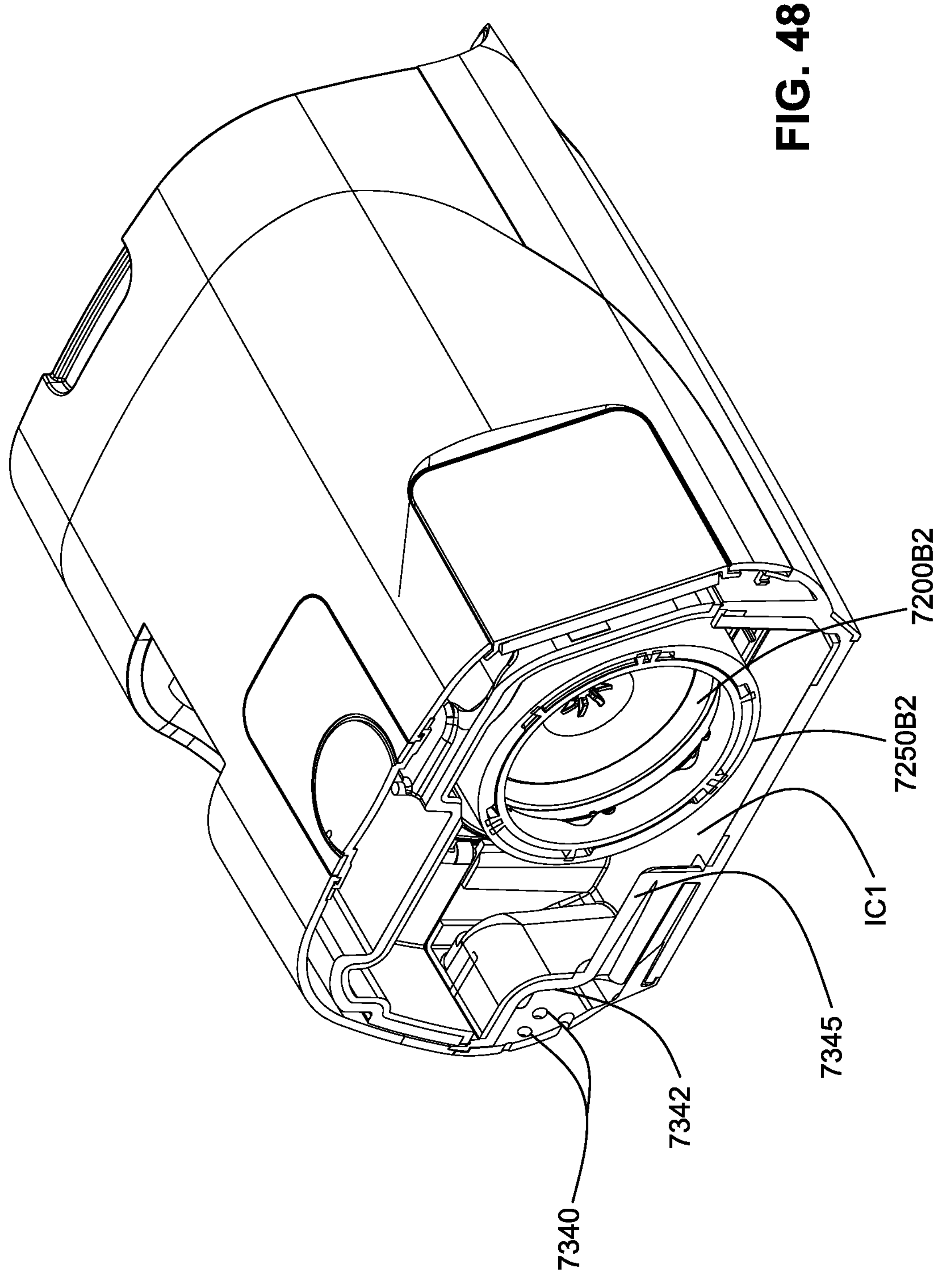

FIG. 48 is another cross-sectional view of a complete pneumatic block including second blower sub-assembly according to an example of the present technology.

Figure 49:
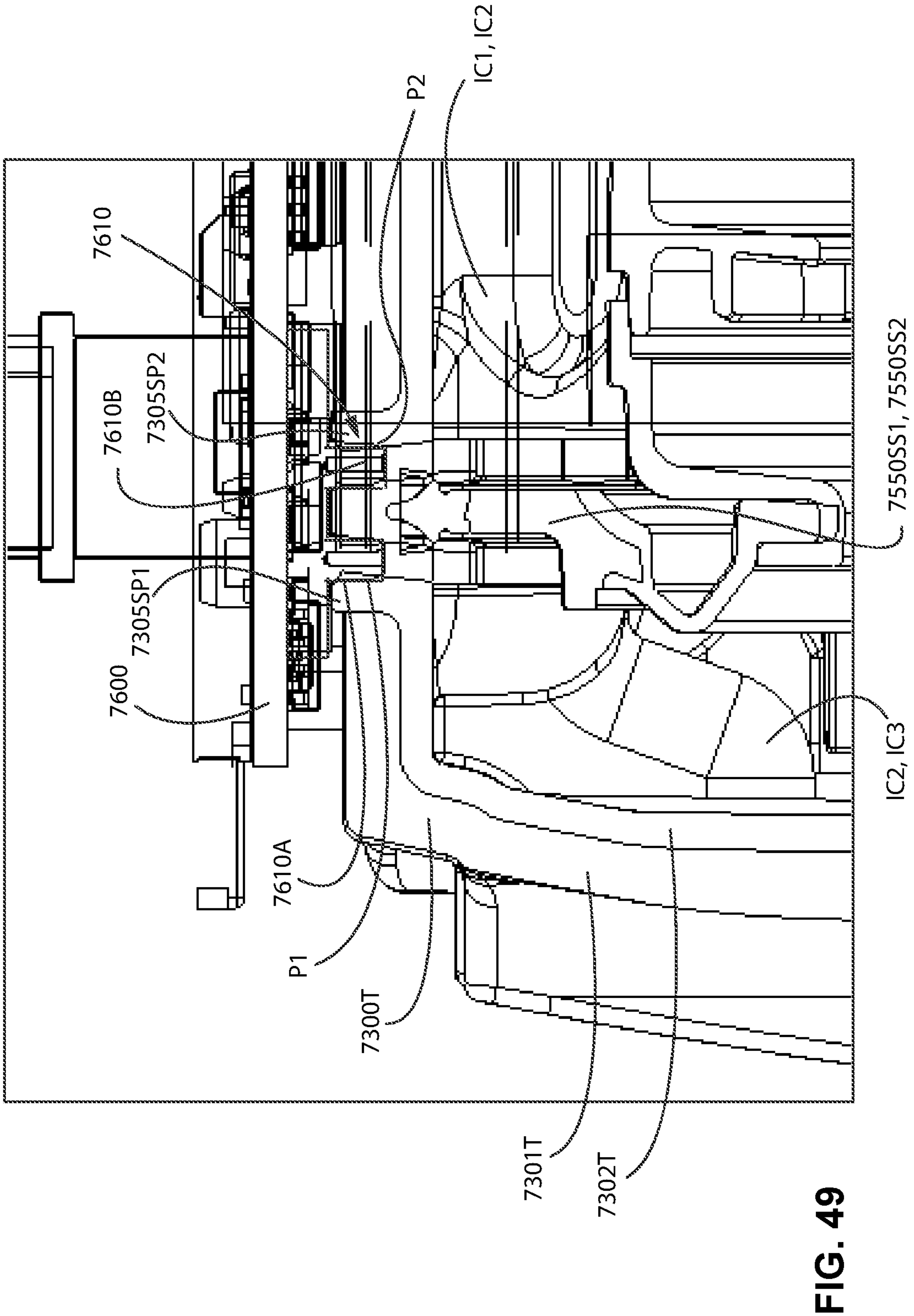

FIG. 49 is a cross-sectional view showing an arrangement of a flow sensor according to an example of the present technology.

Figure 50:
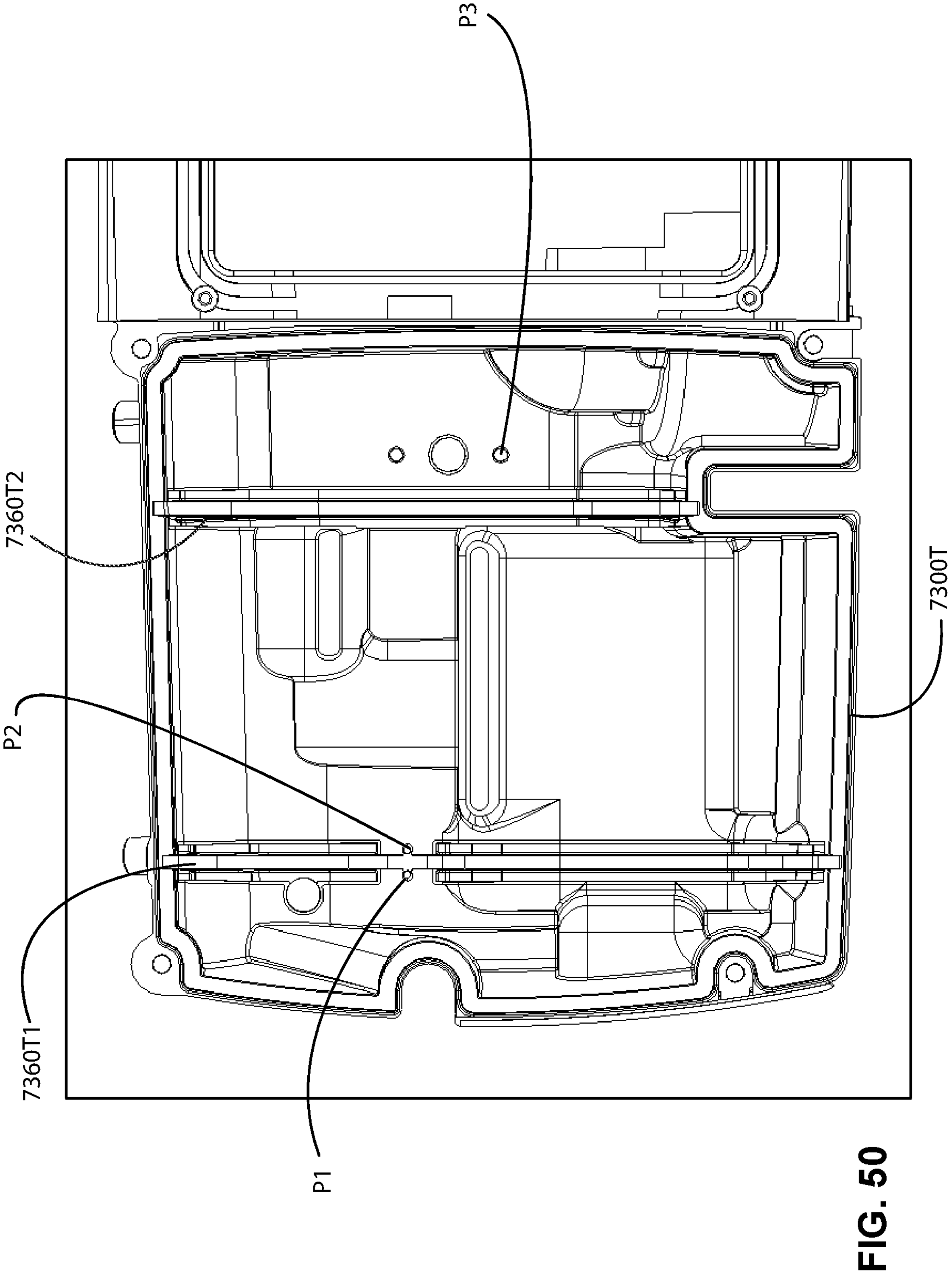

FIG. 50 is a bottom view of a top chassis of a chassis assembly showing flow and pressure ports according to an example of the present technology.

Figure 51:
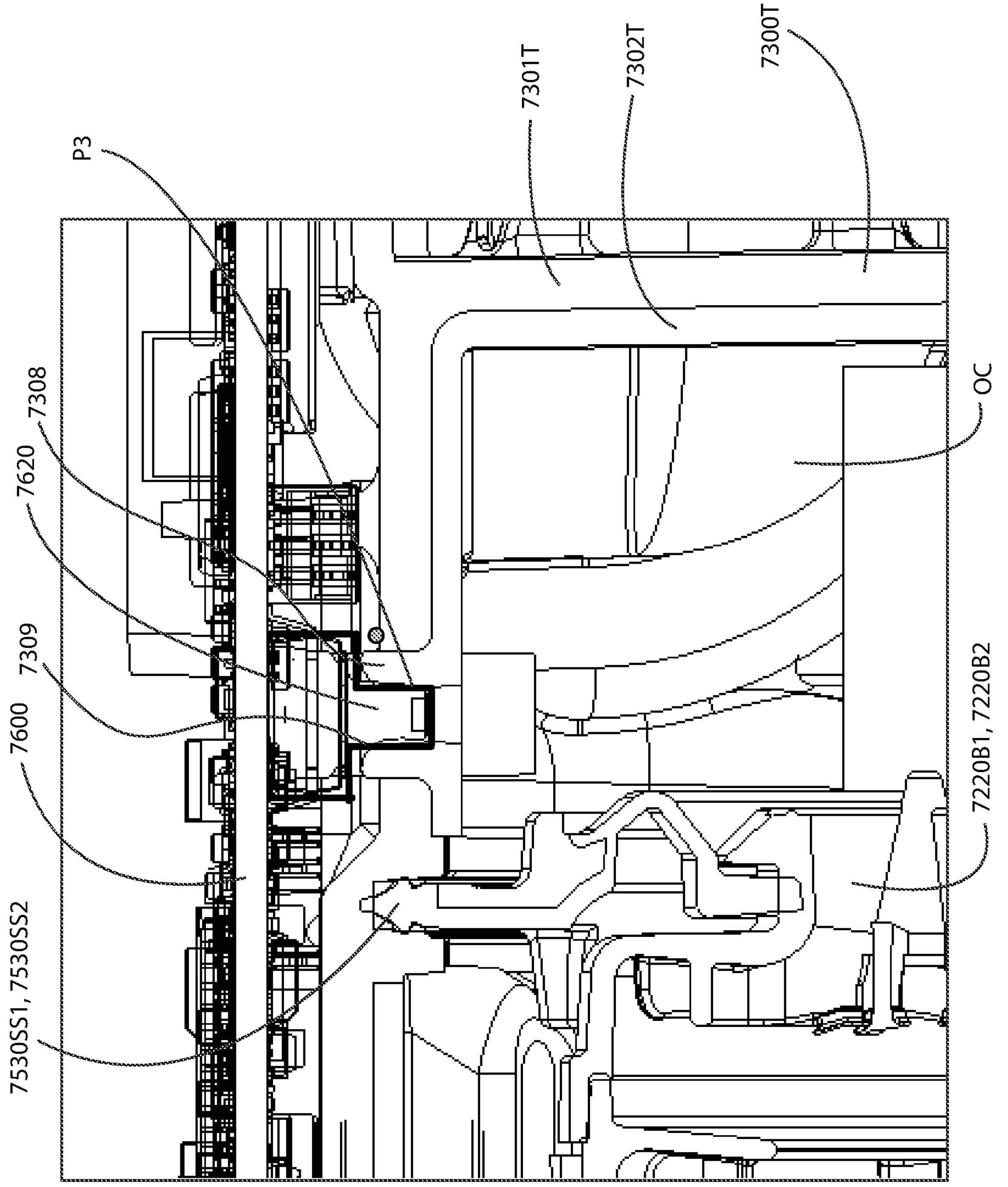

FIG. 51 is a cross-sectional view showing arrangement of a pressure sensor according to an example of the present technology.

Figure 52:
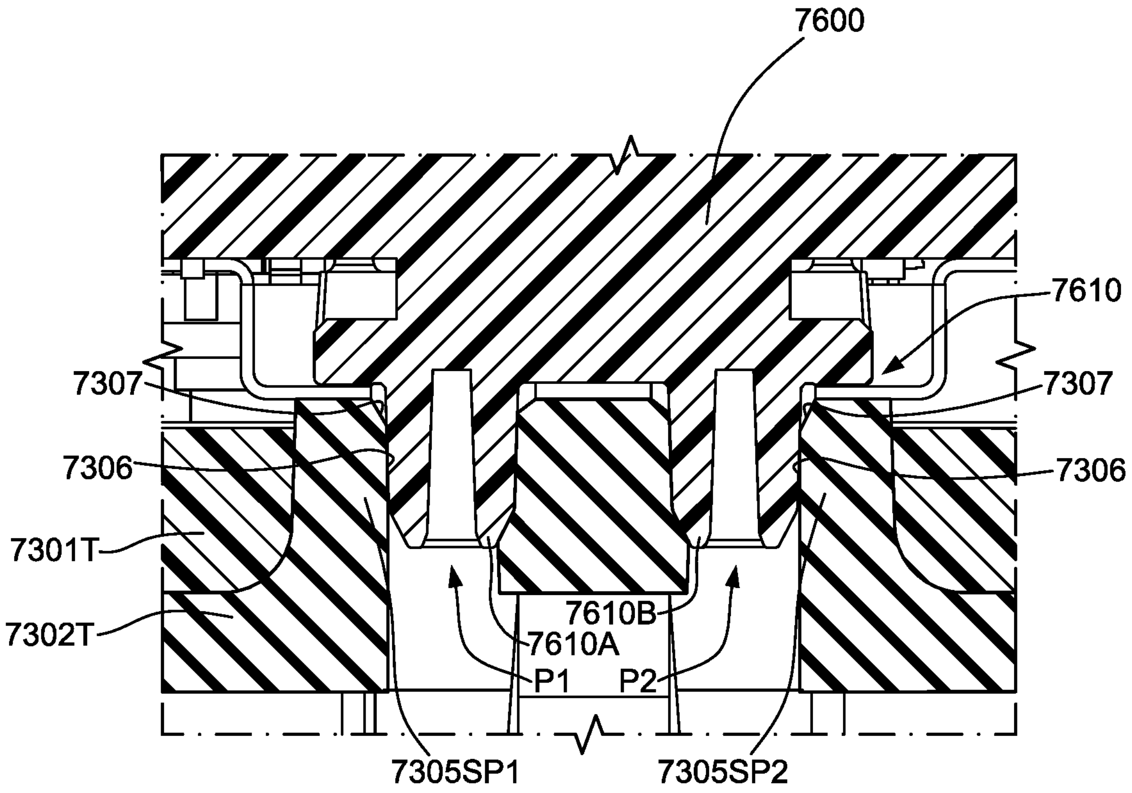

FIG. 52 is a cross-sectional view showing sealing portions for a flow sensor according to an example of the present technology.

Figure 53:
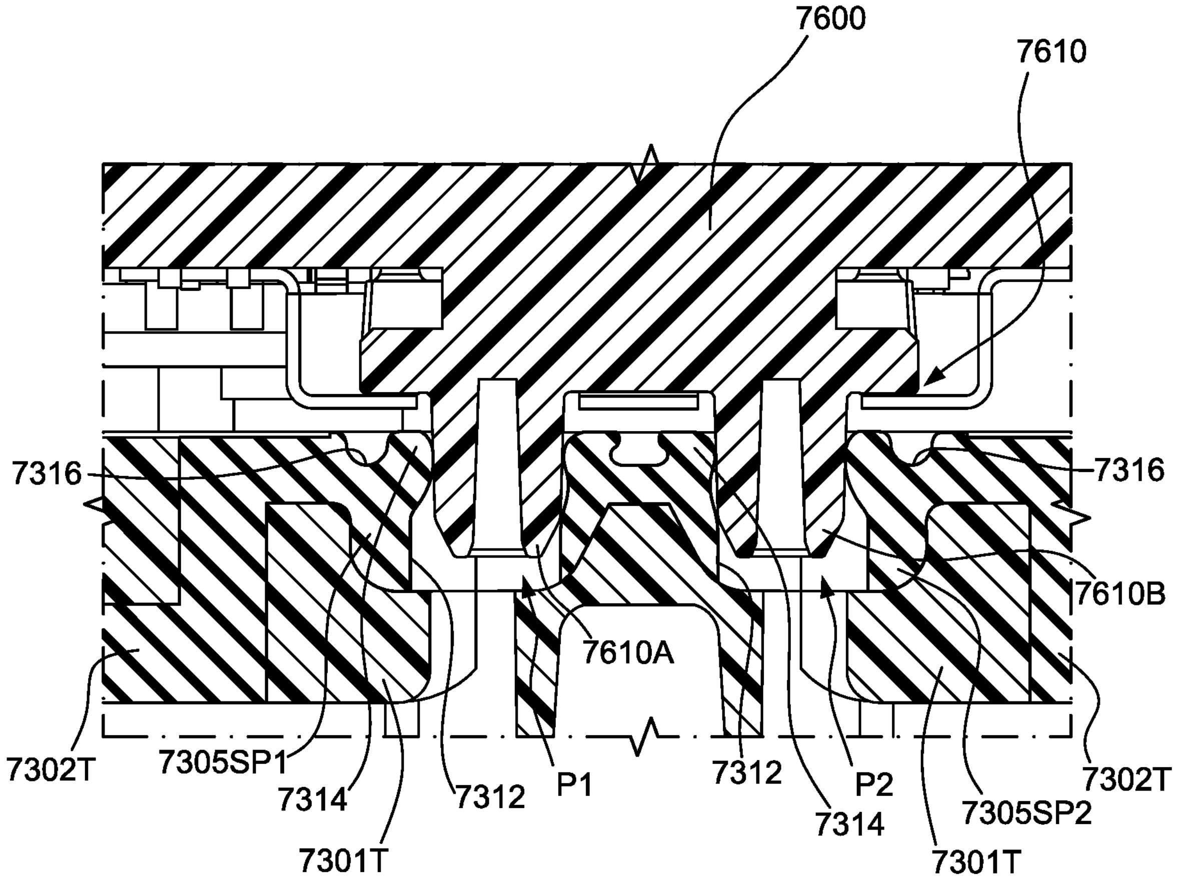

FIG. 53 is a cross-sectional view showing sealing portions for a flow sensor according to another example of the present technology.

Figure 54:
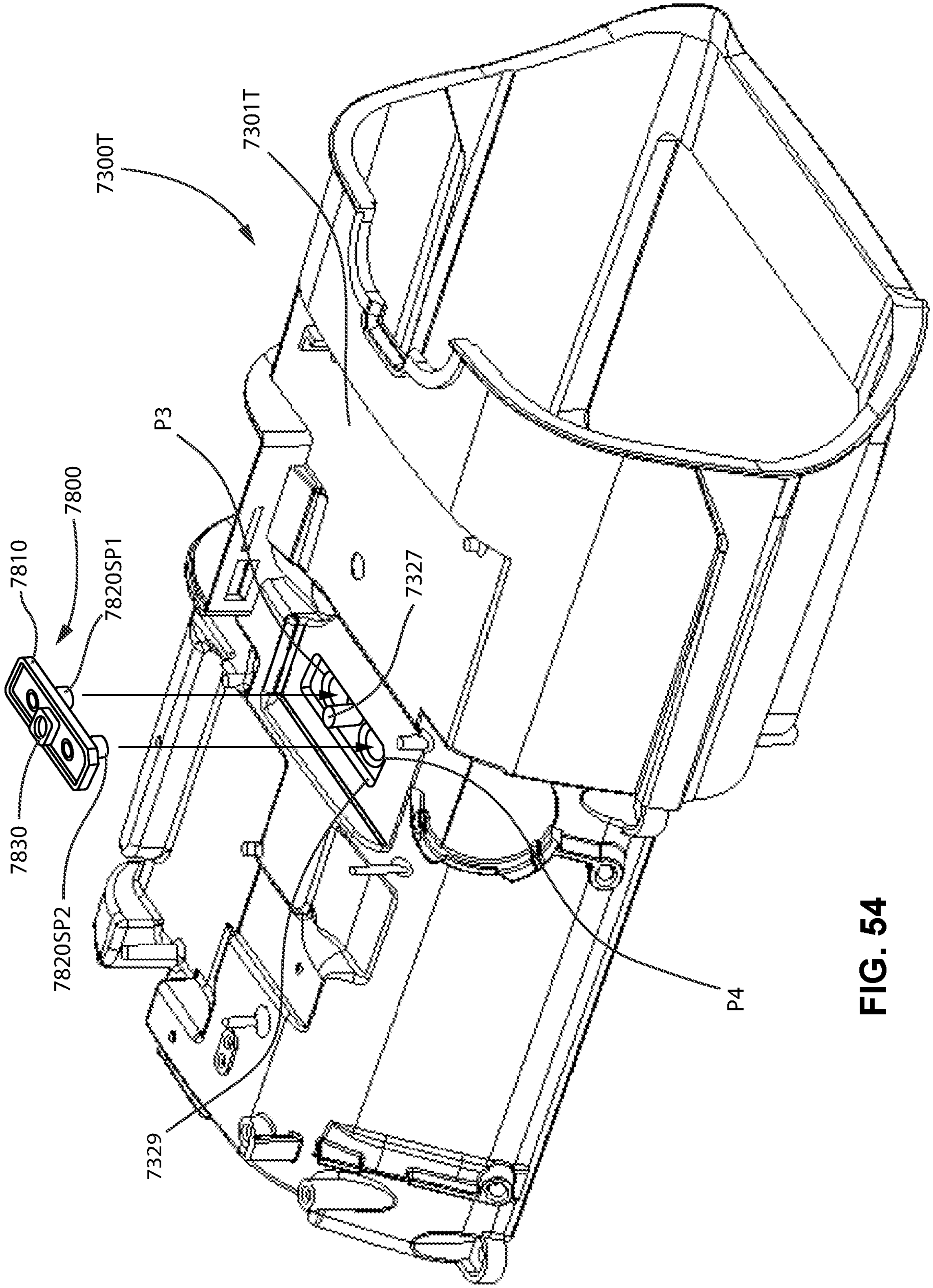

FIG. 54 is a perspective view of a chassis assembly and a pressure sensor seal according to an example of the present technology.

Figure 55:
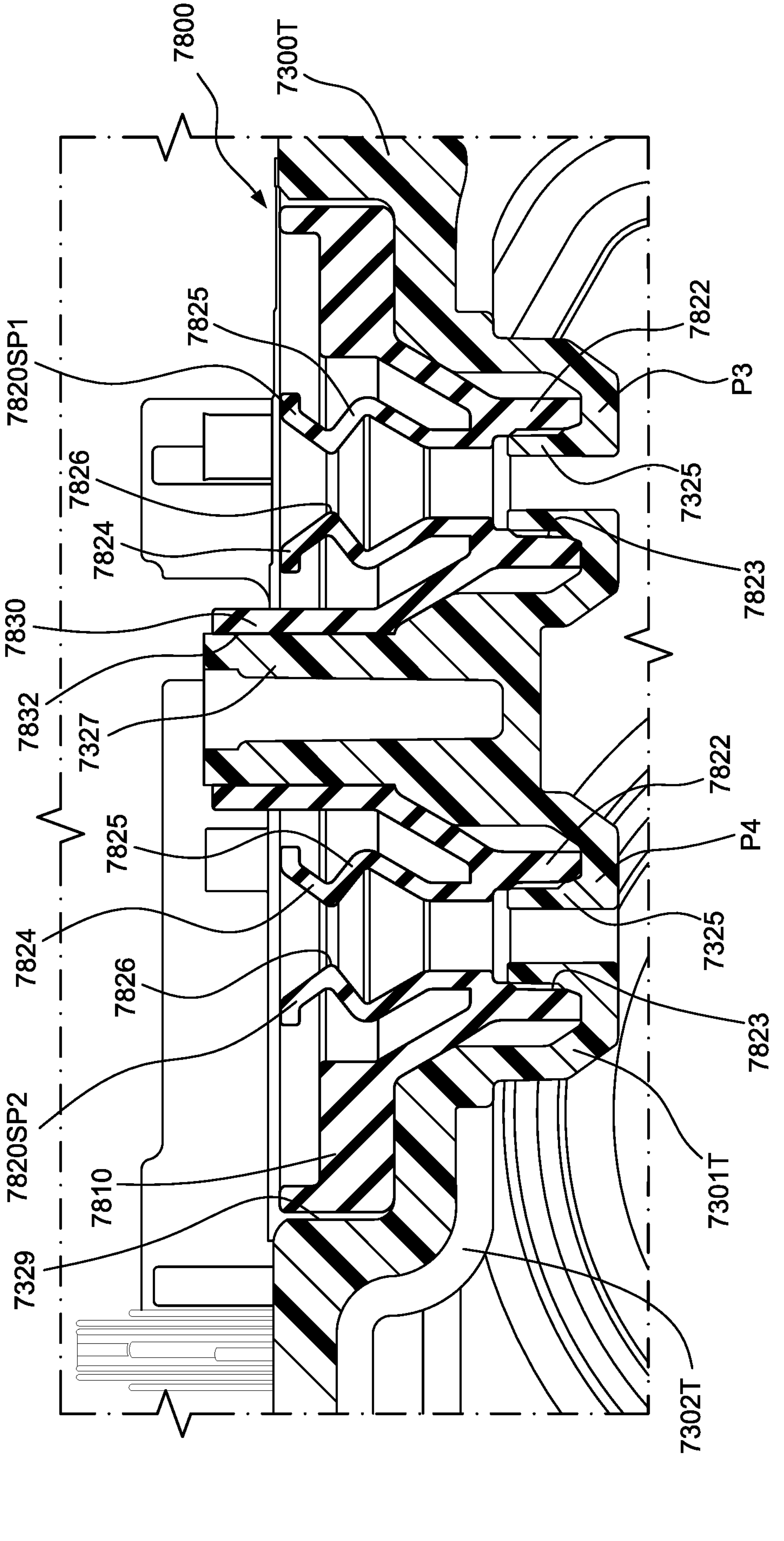

FIG. 55 is a cross-sectional view showing the pressure sensor seal of FIG. 54 connected to the chassis assembly according to an example of the present technology.

Figure 56:
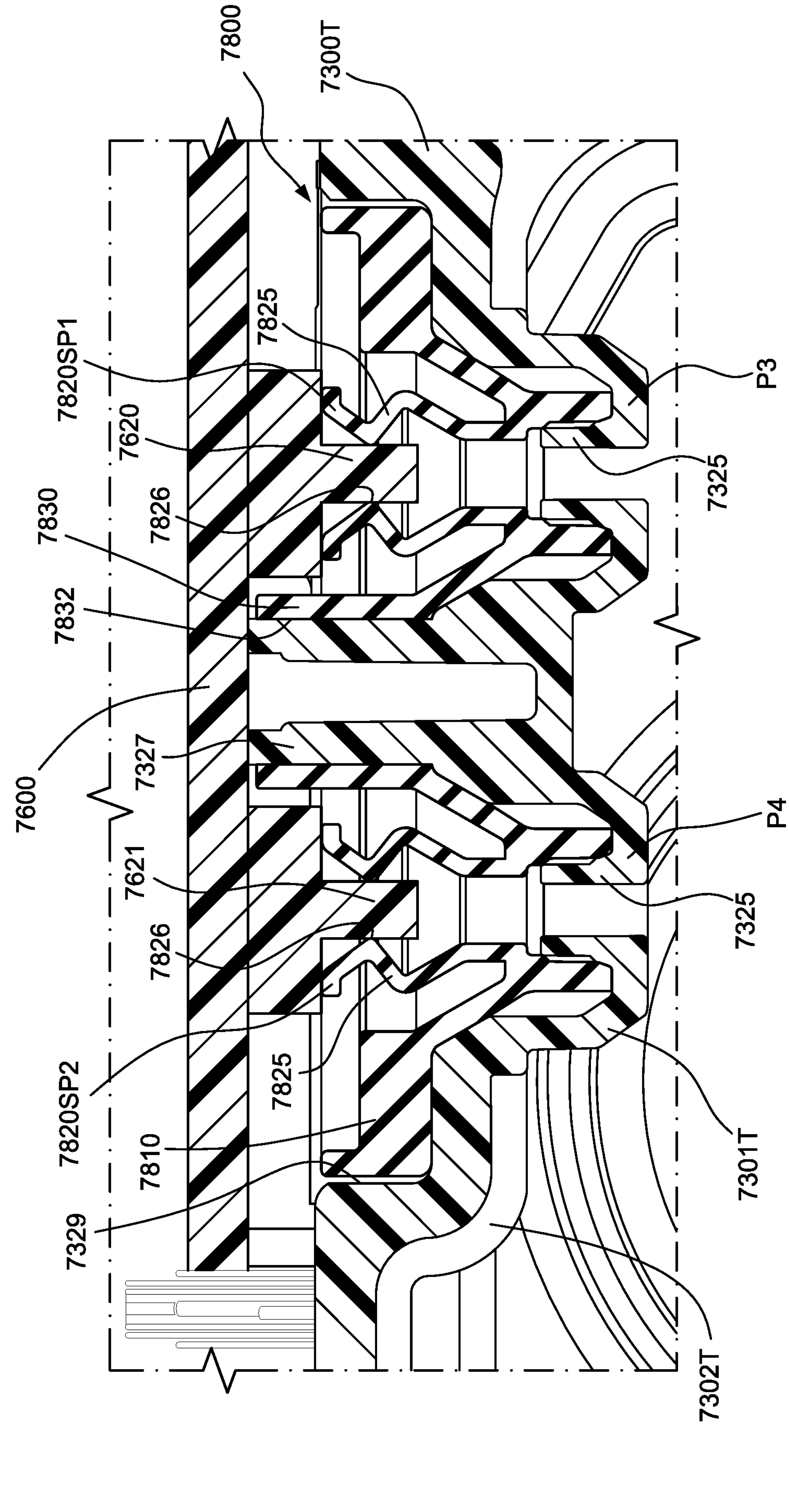

FIG. 56 is a cross-sectional view showing the pressure sensor seal of FIG. 54 connected to the chassis assembly and the pressure sensors of the PCBA according to an example of the present technology.

Figure 57:
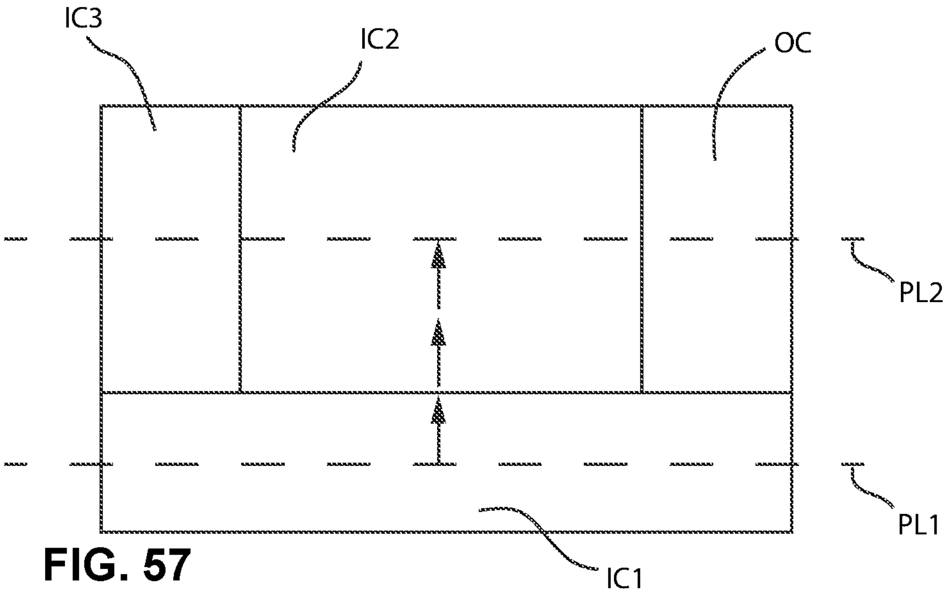

FIG. 57 is a schematic view showing a first configuration of a pneumatic block according to an example of the present technology.

Figure 58:
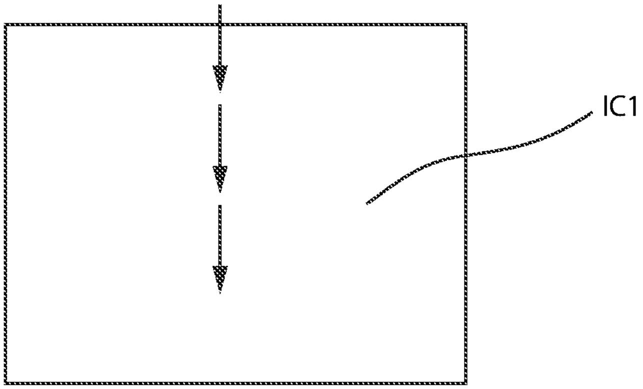

FIG. 58 is a schematic view through a first plane of the first configuration of the pneumatic block of FIG. 57.

Figure 59:
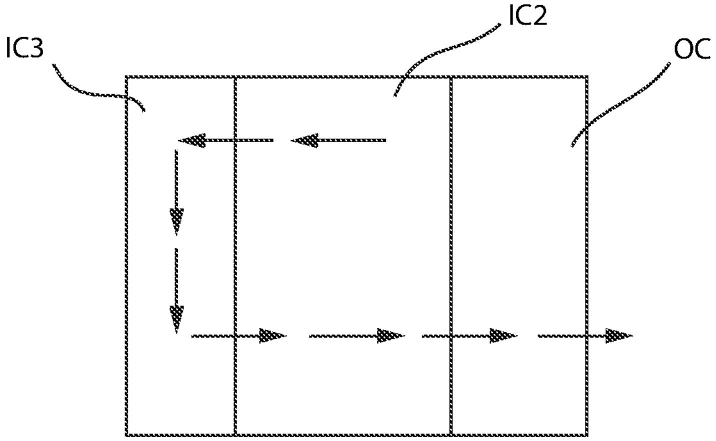

FIG. 59 is a schematic view through a second plane of the first configuration of the pneumatic block of FIG. 57.

Figure 60:
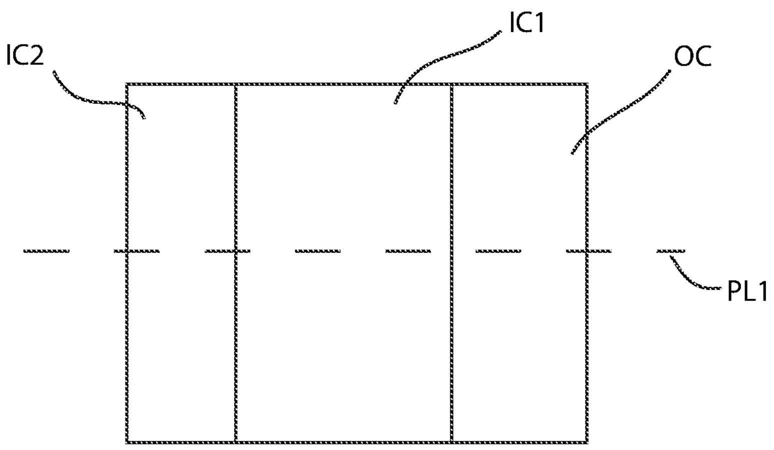

FIG. 60 is a schematic view showing a second configuration of a pneumatic block according to an example of the present technology.

Figure 61:
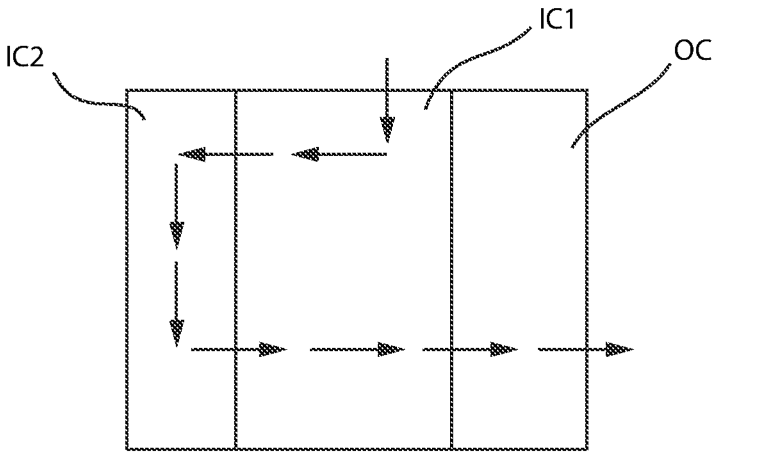

FIG. 61 is a schematic view through a first plane of the second configuration of the pneumatic block of FIG. 60.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

Figure 1A:
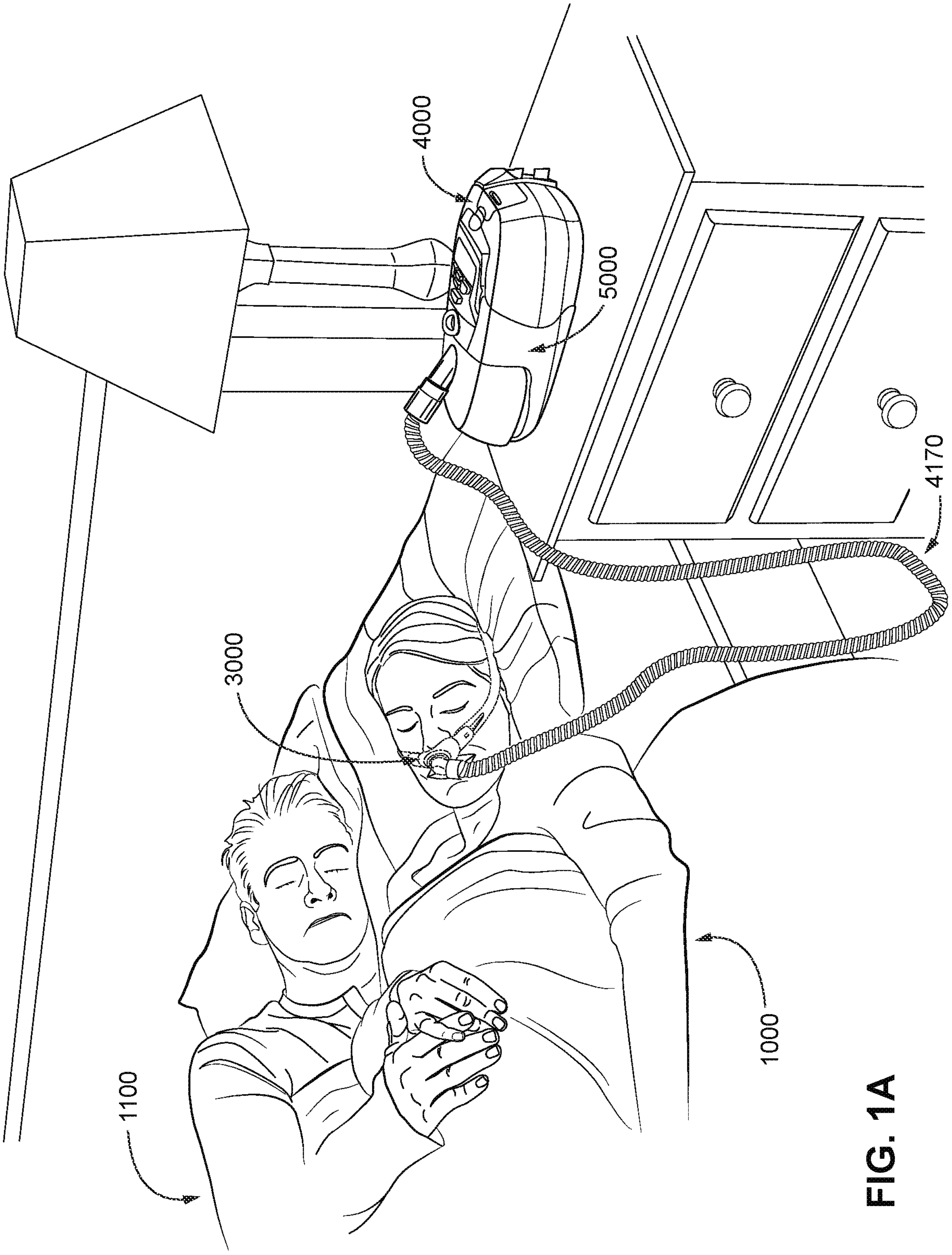
Figure 1B:
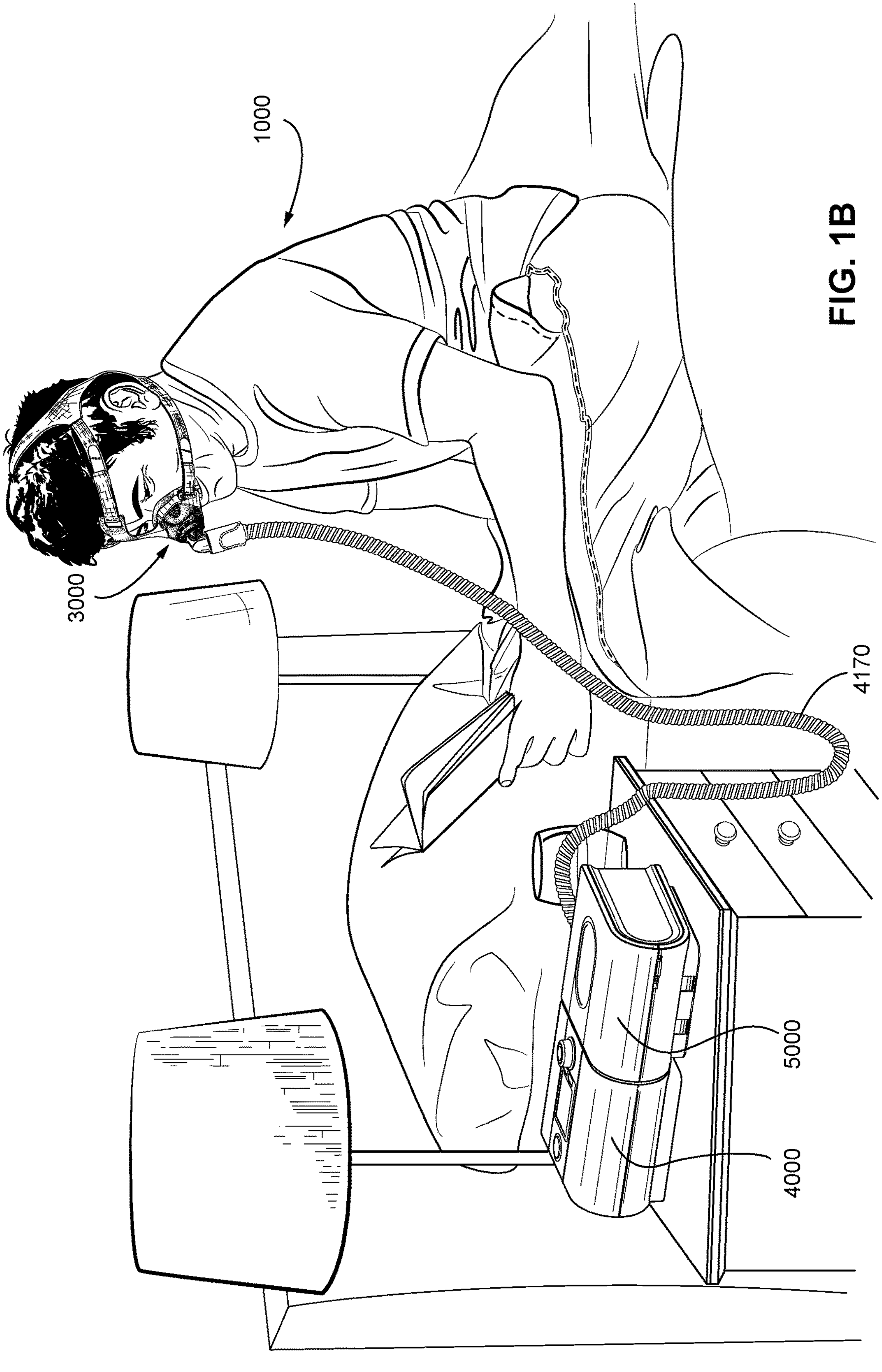
Figure 1C:
Figure 2A:
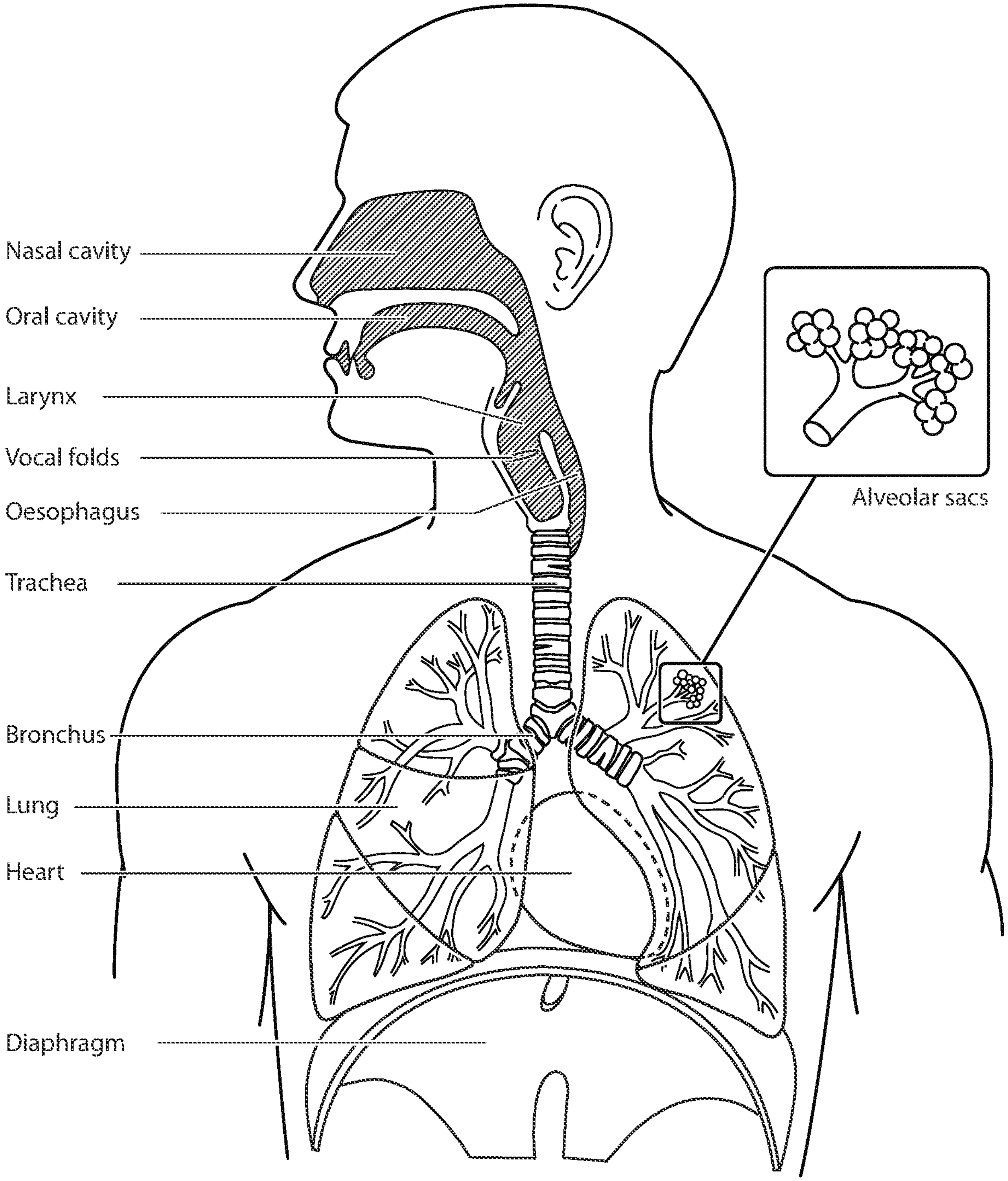
FIG. 2A shows an overview of a human respiratory system including the nasal and oral cavities, the larynx, vocal folds, oesophagus, trachea, bronchus, lung, alveolar sacs, heart and diaphragm.
Figure 2B:
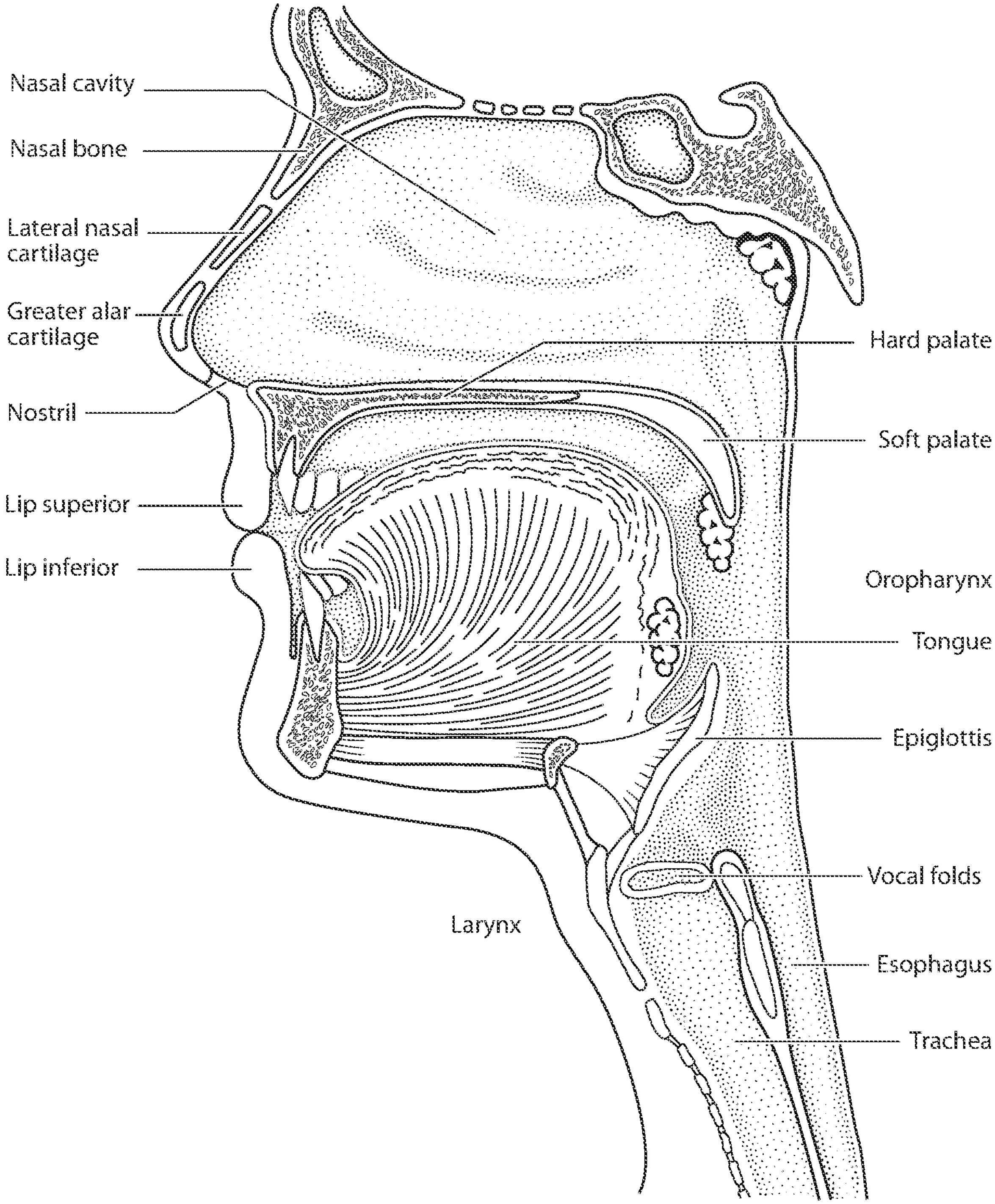
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

In one form, the present technology comprises an apparatus or device for treating a respiratory disorder. The apparatus or device may comprise an RPT device 4000 for supplying pressurised air to the patient 1000 via an air circuit 4170 to a patient interface 3000, e.g., see FIGS. 1A to 1C.

5.3 Patient Interface

FIG. 3A shows a non-invasive patient interface 3000 in accordance with one aspect of the present technology comprising the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

5.4 RPT Device

An exploded view of an RPT device 4000 in accordance with one aspect of the present technology is shown in FIG. 5A. An RPT device 4000 may comprise mechanical, pneumatic, and/or electrical components and is configured to execute one or more algorithms. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10$cmH_2O$, or at least 20 $cmH_2O$.

The RPT device 4000 may include an external housing having one or more panel(s) such as a main panel 4010, a front panel 4012 and a side panel 4014. The RPT device 4000 may also comprise an outlet muffler 4124 as shown in FIGS. 5A and 5B. The outlet muffler 4124 may be removable and replaced with a water reservoir 5110 (see FIG. 5C). In such forms, the RPT device 4000 may be considered to include an integrated humidifier 5000. Thus, the RPT device 4000 may be used with or without humidification depending upon whether the water reservoir 5110 or the outlet muffler 4124 respectively is attached. Preferably the RPT device 4000 comprises a chassis 4016 that supports one or more internal components of the RPT device 4000. In one form the RPT device 4000 comprises a pressure generator 4140, which may be housed in a pneumatic block 4020 coupled to the chassis 4016.

Further examples and details of an exemplary RPT device are described in PCT Publication No. WO 2015/089582, which is incorporated herein by reference in its entirety.

The pneumatic path of the RPT device 4000 (e.g. shown in FIG. 5D) may comprise an inlet air filter 4112, an inlet muffler 4122, a pressure generator 4140 capable of supplying air at positive pressure (preferably a blower 4142) and an outlet muffler 4124 (or a water reservoir 5110 if humidification is required). One or more transducers 4270, such as pressure sensors and flow sensors may be included in the pneumatic path. The pneumatic path may also include anti-spill back valve 4160 to prevent water from the humidifier 5000 spilling back to the electrical components of the RPT device 4000.

As shown in FIG. 5E, the RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202 (e.g., see FIG. 5A). In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of noncontact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components 5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure “0”, to eight logical signals indicating whether the eight respective segments are to be activated to display a particular character or symbol.

5.4.3 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules, e.g., see FIG. 5F.

5.4.3.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface or mask pressure Pm, the respiratory flow rate Qr, and the leak flow rate Ql.

In various forms of the present technology, the pre-processing module 4310 comprises one or more of the following algorithms: pressure compensation 4312, vent flow rate estimation 4314, leak flow rate estimation 4316, and respiratory flow rate estimation 4318.

5.4.3.1.1 Pressure Compensation

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 4170 and provides as an output an estimated pressure, Pm, in the patient interface 3000.

5.4.3.1.2 Vent Flow Rate Estimation

In one form of the present technology, a vent flow rate estimation algorithm 4314 receives as an input an estimated pressure, Pm, in the patient interface 3000 and estimates a vent flow rate of air, Qv, from a vent 3400 in a patient interface 3000.

5.4.3.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

5.4.3.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

5.4.3.2 Therapy Engine Module

In one form of the present technology, a therapy engine module 4320 receives as inputs one or more of a pressure, Pm, in a patient interface 3000, and a respiratory flow rate of air to a patient, Qr, and provides as an output one or more therapy parameters.

In one form of the present technology, a therapy parameter is a treatment pressure Pt.

In one form of the present technology, therapy parameters are one or more of an amplitude of a pressure variation, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

5.4.3.2.1 Phase Determination

In one form of the present technology, the RPT device 4000 does not determine phase.

In one form of the present technology, a phase determination algorithm 4321 receives as an input a signal indicative of respiratory flow rate, Qr, and provides as an output a phase Φ of a current breathing cycle of a patient 1000.

In some forms, known as discrete phase determination, the phase output Φ is a discrete variable. One implementation of discrete phase determination provides a bi-valued phase output Φ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output Φ is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold. The inhalation time Ti and the exhalation time Te may be estimated as typical values over many respiratory cycles of the time spent with phase Φ equal to 0 (indicating inspiration) and 0.5 (indicating expiration) respectively.

Another implementation of discrete phase determination provides a tri-valued phase output Φ with a value of one of inhalation, mid-inspiratory pause, and exhalation.

In other forms, known as continuous phase determination, the phase output Φ is a continuous variable, for example varying from 0 to 1 revolutions, or 0 to 27π radians. RPT devices 4000 that perform continuous phase determination may trigger and cycle when the continuous phase reaches 0 and 0.5 revolutions, respectively. In one implementation of continuous phase determination, a continuous value of phase Φ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.

4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the phase Φ is first discretely estimated from the respiratory flow rate Qr as described above, as are the inhalation time Ti and the exhalation time Te. The continuous phase Φ at any instant may be determined as the half the proportion of the inhalation time Ti that has elapsed since the previous trigger instant, or 0.5 revolutions plus half the proportion of the exhalation time Te that has elapsed since the previous cycle instant (whichever instant was more recent).

5.4.3.2.2 Waveform Determination

In one form of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase Φ of a respiratory cycle of a patient according to a waveform template Π(Φ).

In one form of the present technology, a waveform determination algorithm 4322 provides a waveform template Π(Φ) with values in the range [0, 1] on the domain of phase values Φ provided by the phase determination algorithm 4321 to be used by the therapy parameter determination algorithm 4329.

In one form, suitable for either discrete or continuously-valued phase, the waveform template Π(Φ) is a square-wave template, having a value of 1 for values of phase up to and including 0.5 revolutions, and a value of 0 for values of phase above 0.5 revolutions. In one form, suitable for continuously-valued phase, the waveform template Π(Φ) comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. In one form, suitable for continuously-valued phase, the waveform template Π(Φ) is based on a square wave, but with a smooth rise from 0 to 1 for values of phase up to a "rise time" that is less than 0.5 revolutions, and a smooth fall from 1 to 0 for values of phase within a "fall time" after 0.5 revolutions, with a "fall time" that is less than 0.5 revolutions.

In some forms of the present technology, the waveform determination algorithm 4322 selects a waveform template $\Pi(\Phi)$ from a library of waveform templates, dependent on a setting of the RPT device. Each waveform template $\Pi(\Phi)$ in the library may be provided as a lookup table of values $\Pi$ against phase values $\Phi$. In other forms, the waveform determination algorithm 4322 computes a waveform template $\Pi(\Phi)$ "on the fly" using a predetermined functional form, possibly parametrised by one or more parameters (e.g. time constant of an exponentially curved portion). The parameters of the functional form may be predetermined or dependent on a current state of the patient 1000.

In some forms of the present technology, suitable for discrete bi-valued phase of either inhalation ($\Phi$=0 revolutions) or exhalation ($\Phi$=0.5 revolutions), the waveform determination algorithm 4322 computes a waveform template $\Pi$ "on the fly" as a function of both discrete phase $\Phi$ and time t measured since the most recent trigger instant. In one such form, the waveform determination algorithm 4322 computes the waveform template $\Pi(\Phi, t)$ in two portions (inspiratory and expiratory) as follows:

$$\prod(\Phi, t) = \begin{cases} \prod_i(t), & \Phi = 0 \\ \prod_e(t - T_i), & \Phi = 0.5 \end{cases}$$

where $\Pi_i(t)$ and $\Pi_e(t)$ are inspiratory and expiratory portions of the waveform template $\Pi(\Phi, t)$. In one such form, the inspiratory portion $\Pi_i(t)$ of the waveform template is a smooth rise from 0 to 1 parametrised by a rise time, and the expiratory portion $\Pi_e(t)$ of the waveform template is a smooth fall from 1 to 0 parametrised by a fall time.

5.4.3.2.3 Ventilation Determination

In one form of the present technology, a ventilation determination algorithm 4323 receives an input a respiratory flow rate Qr, and determines a measure indicative of current patient ventilation, Vent.

In some implementations, the ventilation determination algorithm 4323 determines a measure of ventilation Vent that is an estimate of actual patient ventilation. One such implementation is to take half the absolute value of respiratory flow rate, Qr, optionally filtered by low-pass filter such as a second order Bessel low-pass filter with a corner frequency of 0.11 Hz.

In other implementations, the ventilation determination algorithm 4323 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where $0<K<1$. There is an arbitrarily large number of measures that are exactly proportional to ventilation if the flow rate shape is constant.

5.4.3.2.4 Determination of Inspiratory Flow Limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow rate-time curve for each breath. The curve described by the points is then scaled by a scalar to have unity length (duration/period) and unity area to remove the effects of changing breathing rate and depth. The scaled breaths are then compared in a comparator with a pre-stored template representing a normal unobstructed breath, similar to the inspiratory portion of the breath shown in FIG. 6A. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty five scaled data points are generated by the central controller 4230, and represent a moving average of the preceding several inspiratory events, e.g., three events. The moving average of continuously updated values of the (e.g., sixty five) points are hereinafter called the "scaled flow rate", designated as Qs(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g. thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical patient.

Shape factor 2 is calculated as the RMS deviation from unit scaled flow rate, taken over the middle (e.g. thirty two) points. An RMS deviation of about 0.2 units is taken to be normal. An RMS deviation of zero is taken to be a totally flow— limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can be other than those described.

5.4.3.2.5 Determination of Apneas and Hypopneas

In one form of the present technology, the central controller 4230 executes an apnea/hypopnea determination algorithm 4325 for the determination of the presence of apneas and/or hypopneas.

In one form, the apnea/hypopnea determination algorithm 4325 receives as an input a respiratory flow rate signal Qr and provides as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

5.4.3.2.6 Determination of Snore

In one form of the present technology, the central controller 4230 executes one or more snore determination algorithms 4326 for the determination of the extent of snore.

In one form, the snore determination algorithm 4326 receives as an input a respiratory flow rate signal Qr and provides as an output a metric of the extent to which snoring is present.

The snore determination algorithm 4326 may comprise the step of determining the intensity of the flow rate signal in the range of 30-300 Hz. Further, the snore determination algorithm 4326 may comprise a step of filtering the respiratory flow rate signal Qr to reduce background noise, e.g., the sound of airflow in the system from the blower.

5.4.3.2.7 Determination of Airway Patency

In one form of the present technology, the central controller 4230 executes one or more airway patency determination algorithms 4327 for the determination of the extent of airway patency.

In one form, the airway patency determination algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In one form, airway patency determination algorithm 4327 receives as an input a respiratory flow rate signal Qr, and determines the presence or absence of a cardiogenic signal. The absence of a cardiogenic signal is taken to be an indication of a closed airway.

5.4.3.2.8 Determination of Target Ventilation

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4328 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

5.4.3.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt=A\Pi(\Phi,t)+P_0 \tag{1}$$

where:

A is the amplitude, $\Pi(\Phi, t)$ is the waveform template value (in the range 0 to 1) at the current value $\Phi$ of phase and t of time, and $P_0$ is a base pressure.

If the waveform determination algorithm 4322 provides the waveform template $\Pi(\Phi, t)$ as a lookup table of values $\Pi$ indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen respiratory pressure therapy mode in the manner described below.

5.4.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose mask pressure Pm at the patient interface 3000 is equal to the treatment pressure Pt.

5.4.3.4 Detection of Fault Conditions

In one form of the present technology, the central controller 4230 executes one or more methods 4340 for the detection of fault conditions. The fault conditions detected by the one or more methods 4340 may include at least one of the following:

- Power failure (no power, or insufficient power)
- Transducer fault detection
- Failure to detect the presence of a component
- Operating parameters outside recommended ranges (e.g. pressure, flow rate, temperature, $PaO_2$)
- Failure of a test alarm to generate a detectable alarm signal.

Upon detection of the fault condition, the corresponding algorithm 4340 signals the presence of the fault by one or more of the following:

- Initiation of an audible, visual &/or kinetic (e.g. vibrating) alarm
- Sending a message to an external device
- Logging of the incident

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier 5.6.1 Humidifier Overview

In one form of the present technology there is provided a humidifier 5000 (e.g. as shown in FIG. 5C) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet to receive a flow of air, and a humidifier outlet to deliver a humidified flow of air. The humidifier 5000 may further comprise a humidifier base, which may be adapted to receive the humidifier reservoir and comprise a heating element.

5.6.2 RPT Device and Humidifier

FIGS. 6-8 illustrates a humidifier 6000 according to an example of the present technology. As illustrated, the humidifier 6000 includes a reservoir dock 6050 structured and arranged to receive a water reservoir 6100. In the illustrated example, the humidifier 6000 is integrated with an RPT device 7000 such that a pneumatic block 7100 of the RPT device 7000 comprises components that perform the function of the RPT device 7000 as well as components that perform the function of the humidifier 6000. For example, as shown in FIG. 8, the reservoir dock 6050 is integrated with the pneumatic block 7100 of the RPT device to provide an integral unit, with the reservoir dock 6050 structured and arranged to receive the water reservoir 6100.

It should be appreciated that the humidifier 6000 (e.g., reservoir dock 6050) may be provided separately to the RPT device 7000 in an alternative arrangement. In such arrangement, additional interfaces may be used to connect the humidifier 6000 (e.g., reservoir dock 6050) to the RPT device 7000.

The RPT device 7000 comprises a blower 7200B1 or 7200B2 supported within the pneumatic block 7100, e.g. see FIGS. 30 and 46. Each blower is structured and arranged for producing a flow, or a supply, of air at positive pressure, e.g., in the range of about 2-50 $cmH_2O$. Each blower is operable to draw a supply of air into the pneumatic block 7100, e.g., through one or more inlet openings in the pneumatic block, and into an inlet thereof (blower inlet), and provide a pressurized supply of air at an outlet (blower outlet). The blower outlet is communicated with the humidifier 6000, e.g., an inlet of the water reservoir 6100.

The pneumatic block 7100 according to an example of the present technology is configured and arranged to support different blowers, e.g., depending on the therapy required. In the illustrated example, the pneumatic block 7100 is configured and arranged to support a selected one of at least two different blowers 7200B1 or 7200B2, e.g. see FIGS. 30 and 46. For example, the pneumatic block 7100 may be configured and arranged to support a blower 7200B1 of a first type, e.g., configured for CPAP or APAP therapy, and the pneumatic block 7100 may be configured and arranged to support a blower 7200B2 of a second type, e.g., configured for bi-level therapy. However, it should be appreciated that the pneumatic block 7100 may be configured and arranged to support a selected one or more than two different blowers. In an example, each of the blowers may include a single stage design or a multi-stage design, e.g., two or more stage designs.

Pneumatic Block

As shown in FIGS. 8-15, the pneumatic block 7100 includes a chassis assembly 7300 including an upper or top chassis 7300T (also referred to as an upper or top case) and a lower or bottom chassis 7300B (also referred to as a lower or bottom case). The chassis assembly 7300 includes a chassis inlet 7310, e.g., in the bottom chassis 7300B, and a chassis outlet 7320, e.g., in the top chassis 7300T. In an example, an external housing 8002 including one or more panels and/or one or more user inputs/displays may enclose the pneumatic block 7100, e.g., see FIGS. 6-7.

The chassis assembly 7300 supports and/or houses internal components of the pneumatic block 7100 including a selected blower sub-assembly 7400SUB1 or 7400SUB2 (each including a blower 7200B1 or 7200B2 and a corresponding support structure 7500SS1 or 7500SS2), e.g., depending on the therapy required. The chassis assembly 7300 also supports a printed circuit board assembly (PCBA) 7600.

The chassis assembly 7300 and internal components, e.g., selected blower sub-assembly 7400SUB1 or 7400SUB2, of the pneumatic block cooperate to form the pneumatic air flow path that extends from the chassis inlet 7310 to the blower inlet of the blower 7200B1 or 7200B2 and from the blower outlet of the blower 7200B1 or 7200B2 to the chassis outlet 7320.

As described below, the pneumatic air flow path includes a tortuous path extending from the chassis inlet 7310 to the chassis outlet 7320, which may extend in more than one plane. The pneumatic air flow path may vary, e.g., depending on the selected blower sub-assembly 7400SUB1 or 7400SUB2 supported within the chassis assembly 7300.

Also, the chassis assembly 7300 and internal components, e.g., selected blower sub-assembly 7400SUB1 or 7400SUB2, of the pneumatic block cooperate to form multiple chambers along the air flow path, e.g., to reduce noise output of the RPT device 7000.

Chassis Assembly

The top and bottom chassis 7300T, 7300B are connected to one another to form a pneumatic block cavity 7350. The pneumatic block cavity 7350 is structured and arranged to support a selected blower sub-assembly 7400SUB1 or 7400SUB2.

In addition, top and bottom chassis 7300T, 7300B are connected to one another to form a reservoir dock 6050 configured to receive the water reservoir 6100.

As best shown in FIGS. 10, 11, 14, and 15, the top chassis 7300T includes a pneumatic block portion 7350T forming a top portion of the pneumatic block cavity 7350 and a dock portion 6050T forming a portion of the reservoir dock 6050. As best shown in FIGS. 12, 13, 14, and 15, the bottom chassis 7300B includes a pneumatic block portion 7350B forming a bottom portion of the pneumatic block cavity 7350 and a dock portion 6050B forming a portion of the reservoir dock 6050.

In the illustrated example, the top and bottom chassis 7300T, 7300B comprise the same materials. For example, the top chassis 7300T includes a first part or base mold 7301T constructed of a relatively rigid material (e.g., thermoplastic polymer (e.g., PC, ABS)) and a second part or overmold 7302T constructed of a relatively soft material (e.g., thermoplastic elastomer (TPE) or silicone) that is provided (e.g., by overmolding) to the first part 7301T. In the illustrated example, the overmold 7302T is provided to an interior surface of the base mold 7301T along the pneumatic block portion 7350T (internal skin), however, it should be appreciated that the overmold may be provided to other surfaces of the base mold.

Similarly, the bottom chassis 7300B includes a first part or base mold 7301B constructed of a relatively rigid material (e.g., thermoplastic polymer (e.g., PC, ABS)) and a second part or overmold 7302B constructed of a relatively soft material (e.g., thermoplastic elastomer (TPE) or silicone) that is provided (e.g., by overmolding) to the first part 7301B. In the illustrated example, the overmold 7302B is provided to an interior surface of the base mold 7301B along the pneumatic block portion 7350B (internal skin), however, it should be appreciated that the overmold may be provided to other surfaces of the base mold.

As best shown in FIGS. 14 and 15, the overmold 7302T, 7302B on the top and bottom chassis 7300T, 7300B may provide noise damping properties to attenuate wall-radiated noise and sealing properties to provide a sealing interface between the top and bottom chassis, i.e., sealed pneumatic block cavity 7350.

In an alternative example, the top and bottom chassis 7300T, 7300B may comprise dissimilar materials, e.g., the top chassis 7300T comprises 10% glass filed PC and the bottom chassis 7300B comprises PC/ABS.

The upper wall of the top chassis 7300T is structured and arranged to support the PCBA 7600, e.g., see FIG. 8. As described below, the upper wall includes openings that allow sensors (e.g., flow sensor, pressure sensor) on the PCBA 7600 to protrude into and communicate with the pneumatic block cavity 7350.

The top chassis 7300T includes chassis outlet 7320 adapted to communicate with an inlet of the water reservoir 6100 when the water reservoir is received in the reservoir dock 6050. The top chassis 7300T also includes an opening 7330 to support one or more components configured and arranged to allow communication between an outlet of the water reservoir 6100 and the air circuit 4170.

The bottom chassis 7300B includes a side wall with a plurality of inlet openings 7340 that provide the chassis inlet 7310. The plurality of openings 7340 allow sufficient airflow while preventing the ingress of larger objects. A recessed chamber 7342 is provided to the bottom chassis 7300B in communication with the plurality of openings 7340. The recessed chamber 7342 leads to a long inlet tube 7345 in communication with the pneumatic block cavity 7350. In use, air flows through the plurality of openings 7340 into the recessed chamber 7342, and from the recessed chamber 7342 through the long inlet tube 7345 into the pneumatic block cavity 7350. In an example, the side wall with inlet openings 7340 may be in the form of a removable door structured and arranged to removably retain and support an inlet air filter within the recessed chamber 7342. In use, the inlet air filter is arranged to filter incoming air to the pneumatic block cavity 7350. Also, the inlet air filter may be structured to reduce noise radiated back through the chassis inlet 7310.

The top chassis 7300T and the bottom chassis 7300B each comprise structure to locate and support each of at least two different blower sub-assemblies 7400SUB1 or 7400SUB2. For example, as shown in FIGS. 10-13, the top chassis 7300T includes internal locational grooves 7360T1, 7360T2 (e.g., each formed by spaced apart side walls), and the bottom chassis 7300B includes internal locational grooves 7360B1, 7360B2 (e.g., each formed by spaced apart side walls). Each internal locational groove 7360T1, 7360T2, 7360B1, 7360B2 is structured and arranged to receive and support a respective plate of a blower sub-assembly 7400SUB1 or 7400SUB2.

The bottom chassis 7300B includes internal ribs 7365 axially spaced between the internal locational grooves, e.g., see FIGS. 12 and 13. In an example, the internal ribs 7365 are structured and arranged to at least partially surround a blower 7200B2 of a blower sub-assembly 7400SUB2, e.g., to increase case rigidity and provide support, shock resistance and/or damping properties for the blower. In an example, the top chassis 7300T may also include one or more internal ribs, e.g., for case rigidity and blower support.

Also, the side walls of the bottom chassis 7300B are structured and arranged to provide a support structure for a chassis plate 7510SS1 of a blower sub-assembly 7400SUB1. For example, the side walls of the bottom chassis 7300B include one or more support surfaces, ledges, and/or ribs along a perimeter of the pneumatic block portion 7350B arranged to engage and support a chassis plate 7510SS1 of a blower sub-assembly 7400SUB1.

In an example, the reservoir dock 6050 formed by the top and bottom chassis 7300T, 7300B may include a guiding structure 6060 to facilitate alignment and connection of the water reservoir 6100. For example, each side of the reservoir dock 6050 may include a guiding structure 6060 in the form of a rail to define an assembly path for the water reservoir 6100, e.g., see FIG. 7.

The top and bottom chassis 7300T, 7300B may be connected to one another in any suitable manner, e.g., mechanical fasteners, mechanical interlock and/or snap-fit connection.

Blower Sub-Assemblies

As noted above, the chassis assembly 7300 is structured to locate and support a selected one of at least two different blower sub-assemblies 7400SUB1 or 7400SUB2 that are different structurally from one another in at least one aspect, e.g., depending on the therapy required. That is, the chassis assembly 7300 comprises a common component between first and second configurations of the RPT device, i.e., the first configuration including the first blower sub-assembly 7400SUB1 and the second configuration including the second blower sub-assembly 7400SUB2.

The first blower sub-assembly 7400SUB1 includes a blower 7200B1 of a first type, e.g., configured for CPAP or APAP therapy. The second blower sub-assembly 7400SUB2 includes a blower 7200B2 of a second type, e.g., configured for bi-level therapy. As described below, the air flow path and chamber arrangement along the air flow path varies depending on the selected blower sub-assembly 7400SUB1 or 7400SUB2 supported within the chassis assembly 7300.

First Blower Sub-Assembly

As shown in FIGS. 16-19, the first blower sub-assembly 7400SUB1 includes a first blower 7200B1 and a support structure 7500SS1 to support the first blower 7200B1 within the chassis assembly 7300.

In the illustrated example, the first blower 7200B1 includes a three-stage design structured and arranged for producing a flow, or a supply, of air at positive pressure, e.g., up to about 30 $cmH_2O$, e.g., in the range of about 4-30 $cmH_2O$.

The first blower 7200B1 includes a housing including an axial air inlet 7210B1 (blower inlet) and axial air outlet 7220B1 (blower outlet) between which are located three stages with three corresponding impellers, i.e., first and second impellers positioned on one side of the motor and a third impeller positioned on the other side of the motor. However, other suitable impeller arrangements are possible. Each impeller is followed by a set of stator vanes structured and configured to direct the air flow to the next stage. The blower housing is relatively rigid and forms a substantially sealed structure structured and arranged to sealingly separate air flow through an interior of the first blower from the pneumatic block cavity.

Further examples and details of the first blower 7200B1 are described in PCT Publication No. WO 2013/020167, which is incorporated herein by reference in its entirety.

The support structure 7500SS1 includes a chassis plate 7510SS1, an outlet plate assembly 7530SS1, and a flow plate assembly 7550SS1.

The flow plate assembly 7550SS1 includes a base plate 7552SS1, a flow tube array 7554SS1, and a blower suspension 7556SS1 (inlet end suspension) supported within an opening provided to the base plate 7552SS1. In addition, a sealing lip or sealing flange 7558SS1 is provided along the edge or perimeter of the base plate 7552SS1.

In an example, the base plate 7552SS1 and the flow tube array 7554SS1 comprise a first part or base mold constructed of a relatively rigid material (e.g., thermoplastic polymer), and the blower suspension 7556SS1 and sealing lip 7558SS1 comprise a second part or overmold constructed of a relatively soft material (e.g., TPE or silicone) that is provided (e.g., by overmolding) to the first part.

In an example, the flow plate assembly 7550SS1 is formed as a separate and distinct structure from the chassis plate 7510SS1, and then connected thereto. For example, the chassis plate 7510SS1 includes a locational groove 7512SS1 (e.g., formed by spaced apart side walls) to locate and support the flow plate assembly 7550SS1. As illustrated, the base plate 7552SS1 of the flow plate assembly 7550SS1 extends generally perpendicular to the chassis plate 7510SS1 when connected thereto. Also, the base plate 7552SS1 of the flow plate assembly 7550SS1 may be secured to the chassis plate 7510SS1, e.g., via a clip structure (e.g., flexible tabs on the base plate 7552SS1 inserted into respective openings on the chassis plate 7510SS1).

The outlet plate assembly 7530SS1 includes a base plate 7532SS1 and a blower suspension 7536SS1 (outlet end suspension) supported within an opening provided to the base plate 7532SS1. In addition, a sealing lip or sealing flange 7538SS1 is provided along the edge or perimeter of the base plate 7532SS1.

In an example, the outlet plate assembly 7530SS1 is formed in one piece with the chassis plate 7510SS1. As illustrated, base plate 7532SS1 extends generally perpendicular to the chassis plate 7510SS1.

The chassis plate 7510SS1 also includes a flow tube 7515SS1. In the example, the flow tube 7515SS1 includes an axis that extends generally perpendicular to the chassis plate 7510SS1.

In an example, the chassis plate 7510SS1 and base plate 7532SS1 comprises a first part or base mold constructed of a relatively rigid material (e.g., thermoplastic polymer), and the blower suspension 7536SS1 and sealing lip 7538SS1 comprise a second part or overmold constructed of a relatively soft material (e.g., TPE or silicone) that is provided (e.g., by overmolding) to the first part.

A sealing lip or sealing flange 7518SS1 may also be provided along the edge or perimeter of the chassis plate 7510SS1, e.g., overmold constructed of a relatively soft material (e.g., TPE or silicone).

The first blower 7200B1 is suspended by the support structure 7500SS1 between the flow plate assembly 7550SS1 and the outlet plate assembly 7530SS1. The flow plate assembly 7550SS1 and the outlet plate assembly 7530SS1 each include a blower suspension 7556SS1, 7536SS1 that cooperate to support the first blower 7200B1 within the chassis assembly 7300, provide seals for the air path, isolate vibrations of the first blower 7200B1, and provide shock resistance. The blower suspension 7556SS1, 7536SS1 may provide additional spring and damping to isolate vibrations and provide shock resistance. Specifically, the flow plate assembly 7550SS1 provides an inlet end suspension 7556SS1 to support the first blower 7200B1 adjacent the blower inlet 7210B1 and the outlet plate assembly 7530SS1 provides an outlet end suspension 7536SS1 to support the first blower 7200B1 adjacent the blower outlet 7220B1, i.e., a suspension is located at each end of the first blower 7200B1. Such arrangement also provides a keying feature to ensure repeatable alignment of the first blower 7200B1 within the first blower sub-assembly 7400SUB1.

In an example, as shown in FIGS. 16 and 18, the base plate 7552SS1 of the flow plate assembly 7550SS1 and/or the base plate 7532SS1 of the outlet plate assembly 7530SS1 may each include one or more flanges 7560SS1 along the perimeter of the blower suspension 7556SS1, 7536SS1, e.g., to act as a rigid stop or bump stop that limits the range of movement provided by the blower suspension 7556SS1, 7536SS1.

In an example, the first blower 7200B1 may be inserted into or otherwise assembled to the flow plate assembly 7550SS1, and then the first blower 7200B1 is inserted into or otherwise assembled to the outlet plate assembly 7530SS1. As noted above, the flow plate assembly 7550SS1 may be secured to the chassis plate 7510SS1 (i.e., by locating and securing the base plate 7552SS1 of the flow plate assembly 7550SS1 within the locational groove 7512SS1 of the chassis plate 7510SS1) to form the first blower sub-assembly 7400SUB1.

In addition, acoustic foam, i.e., outlet foam 7570SS1, is retained by the chassis plate 7510SS1 to increase acoustic resistance and reduce noise. In the illustrated example, the chassis plate 7510SS1 includes a retaining arm 7513SS1 adapted to engage within a slot provided to the outlet foam 7570SS1.

Assembly of First Blower Sub-Assembly to Chassis Assembly

The first blower sub-assembly 7400SUB1 is assembled to the chassis assembly 7300 to form a first configuration of the pneumatic block 7100, e.g., configured for CPAP or APAP therapy.

FIGS. 20-24 show assembly of the first blower sub-assembly 7400SUB1 to the chassis assembly 7300. As shown in FIG. 20, acoustic foam, i.e., inlet foam 7700, is placed into the pneumatic block portion 7350B of the bottom chassis 7300B to increase acoustic resistance and reduce noise. In the illustrated example, the inlet foam 7700 includes a generally U-shape adapted to extend along side walls of the pneumatic block portion 7350B. The first blower sub-assembly 7400SUB1, along with the outlet foam 7570SS1 retained thereto, is then lowered onto the bottom chassis 7300B as shown in FIGS. 20 and 21. As illustrated in FIGS. 22 and 23, edges of the chassis plate 7510SS1 are supported by one or more of support surfaces, ledges, and/or ribs along the perimeter of the pneumatic block portion 7350B. In addition, the underside of the chassis plate 7510SS1 may include a support plate 7519SS1 arranged to engage a bottom wall of the bottom chassis 7300B to further support the first blower sub-assembly 7400SUB1 within the bottom chassis 7300B, e.g., see FIG. 30.

As shown in FIG. 22, the top chassis 7300T is then lowered onto the bottom chassis 7300B, ensuring that the base plate 7552SS1 of the flow plate assembly 7550SS1 and the base plate 7532SS1 of the outlet plate assembly 7530SS1 engage within respective internal locational grooves 7360T1, 7360T2 in the top chassis 7300T to locate and support the first blower sub-assembly 7400SUB1 within the top chassis 7300T. The top and bottom chassis 7300T, 7300B may be retained to one another in any suitable manner, e.g., via mechanical fasteners (e.g., screws) and/or retaining clips.

Finally, as shown in FIG. 24, the PCBA 7600 is attached to an upper wall of the top chassis 7300T, e.g., via mechanical fasteners (e.g., screws), outside the pneumatic block cavity 7350. In the illustrated example, the PCBA 7600 includes a flow sensor and a pressure sensor communicated with the pneumatic block cavity 7350.

The electrical connection between the PCBA 7600 and the first blower 7200B1 may be made via a flexible circuit board (FCB), flexible printed circuits (FPC) and/or flexible flat cables (FFC) extending from the first blower 7200B1 within the pneumatic block cavity 7350 up to the PCBA 7600.

Chamber Arrangement and Pneumatic Air Flow Path Provided by First Blower Sub-Assembly When assembled, the first blower sub-assembly 7400SUB1 and the chassis assembly 7300 cooperate to provide a first configuration of the pneumatic block 7100 including three inlet muffler chambers IC1, IC2, IC3 and an outlet chamber OC along the air flow path, e.g., see FIG. 30.

In the illustrated example, as shown in FIGS. 26-33, the chassis plate 7510SS1 and the bottom chassis 7300B cooperate to form a first inlet muffler chamber IC1; the chassis plate 7510SS1, the base plate 7552SS1 of the flow plate assembly 7550SS1, the base plate 7532SS1 of the outlet plate assembly 7530SS1, and the top chassis 7300T cooperate to form a second inlet muffler chamber IC2; the chassis plate 7510SS1, the base plate 7552SS1 of the flow plate assembly 7550SS1, and the top chassis 7300T cooperate to form a third inlet muffler chamber IC2; and the chassis plate 7510SS1, the base plate 7532SS1 of the outlet plate assembly 7530SS1, and the top chassis 7300T cooperate to form an outlet chamber OC.

In the illustrated example, each of the chambers IC1, IC2, IC3, OC is sealed. The sealing is created via the overmolded sealing lips 7518SS1, 7538SS1, 7558SS1 (e.g., silicone) along the perimeter of the chassis plate 7510SS1 and the base plates 7532SS1, 7552SS1, with controlled compression against the top and bottom chassis 7300T, 7300B, e.g., see FIG. 30.

In the illustrated example, e.g., see FIG. 30, the bottom of the RPT device 7000 includes a bottom surface defining a bottom plane BP that is substantially horizontal when the RPT device 7000 is in a working orientation. As illustrated, in the first configuration of the pneumatic block 7100, the first blower 7200B1 is arranged such that an axis AX1 of the first blower 7200B1 (extending through the air inlet 7210B1 and the air outlet 7220B1) is parallel to the bottom plane BP. That is, the axis AX1 of the first blower 7200B1 extends in a generally horizontal plane when the RPT device 7000 is in a working orientation.

In the illustrated example, the pneumatic air flow path of the first configuration of the pneumatic block 7100 includes a tortuous path extending from the chassis inlet 7310 to the chassis outlet 7320, which extends in more than one plane. For example, the first inlet muffler chamber IC1 extends in a first plane, and the second inlet muffler chamber IC2, the third inlet muffler chamber IC3, and the outlet chamber OC extend in a second plane spaced vertically upward from the first plane, e.g., see FIGS. 30, 32, and 33.

As illustrated, the air flow path of the first configuration of the pneumatic block 7100 is structured and arranged such that air enters the chassis assembly 7300 via the inlet openings 7340 (e.g., see FIG. 25) and into the recessed chamber 7342 (e.g., including an inlet air filter as discussed above), passes from the recessed chamber 7342 through the long inlet tube 7345, and into the first inlet muffler chamber IC1 as shown in FIGS. 26. The long inlet tube 7345 is relatively long to allow for noise reduction (due to high inertance) as air passes from the inlet openings 7340 to the first inlet muffler chamber IC1. The large volume of inlet foam 7700 in the first inlet muffler chamber IC1 increases acoustic resistance and reduces inlet noise.

Air passes from the first inlet muffler chamber IC1 to the second inlet muffler chamber IC2 via the flow tube 7515SS1 in the chassis plate 7510SS1 as shown in FIGS. 27 and 31. The flow tube 7515SS1 is relatively long to allow for noise reduction. As illustrated, the first blower 7200B1 is supported in the second inlet muffler chamber IC2, and receives air at the blower inlet 7210B1 from the third inlet muffler chamber IC3.

Air passes from the second inlet muffler chamber IC2 to the third inlet muffler chamber IC3 via the flow tube array 7554SS1 provided by the flow plate assembly 7550SS1 as shown in FIG. 28. The third inlet muffler chamber IC3 receives air from the flow tube array 7554SS1 and delivers the air to the blower inlet 7210B1 of the first blower 7200B1.

The blower suspension 7556SS1 of the flow plate assembly 7550SS1 may be secured to the first blower 7200B1 in any suitable manner, e.g., wrap around an inlet flange provided to the blower inlet 7210B1 of the first blower 7200B1. The blower suspension 7556SS1 provides a seal along the blower inlet 7210B1, thereby sealing the blower inlet 7210B1 from the second inlet muffler chamber IC2 and providing an air path for air entering the blower inlet 7210B1 from the third inlet muffler chamber IC3. Also, in the illustrated example, the blower suspension 7556SS1 provides structure, e.g., gusset portion, which allows flexibility and relative movement to isolate vibrations of the first blower 7200B1 and provide shock absorption.

The flow tube array 7554SS1 includes a plurality of flow tubes 7555SS1 structured and arranged to extend from the base plate 7552SS1 into the second inlet muffler chamber IC2, e.g., flow tubes 7555SS1 extend generally perpendicular with respect to the base plate 7552SS1. Thus, the air flow path extends from second inlet muffler chamber IC2, through the flow tube array 7554SS1, and into the third inlet muffler chamber IC3. The flow tubes 7555SS1 are structured and arranged to allow laminar flow, provide a defined pressure drop, and provide sufficient length to reduce noise.

In the illustrated example, the flow tube array 7554SS1 includes twelve, spaced-apart flow tubes 7555SS1, e.g., generally arranged in three rows of four tubes. However, it should be appreciated that other suitable number of tubes 7555SS1 are possible (e.g., one or more flow tubes, e.g., 5-15 flow tubes) and the tubes 7555SS1 may be arranged in other suitable manners (e.g., aligned in rows and/or columns, circular arrangement).

In the illustrated example, each of the plurality of flow tubes 7555SS1 includes a circular cross-sectional shape, however it should be appreciated that each of the tubes may include other cross-sectional shapes, e.g., circular shape or noncircular shape. Also, each of the plurality of flow tubes 7555SS1 may include any suitable length, diameter, wall thickness, and cross-sectional area, e.g., depending on the desired noise characteristic. Further, the plurality of flow tubes 7555SS1 may comprise flow tubes of equal lengths and/or unequal lengths.

The first, second, and third inlet muffler chambers IC1, IC2, IC3 cooperate to increase compliance and reduce inlet noise along the air flow path to the blower inlet 7210B1 of the first blower 7200B1.

Air flows through the first blower 7200B1 such that a flow of air at positive pressure is provided at the blower outlet 7220B1 of the first blower 7200B1. The outlet chamber OC receives pressurized air exiting the blower outlet 7220B1 of the first blower 7200B1 as shown in FIG. 29. The pressured air from the outlet chamber OC exits the pneumatic block via the chassis outlet 7320. In an example, the outlet chamber OC of the first configuration of the pneumatic block 7100 may be at a positive pressure of up to about to 30 $cmH_2O$.

The blower suspension 7536SS1 of the outlet plate assembly 7530SS1 may be secured to the first blower 7200B1 in any suitable manner, e.g., wrap around an outlet flange provided to the blower outlet 7220B1 of the first blower 7200B1. The blower suspension 7536SS1 provides a seal along the blower outlet 7220B1, thereby sealing the blower outlet 7220B1 from the second inlet muffler chamber IC2 and providing an air path for air exiting the blower outlet 7220B1 into the outlet chamber OC. Also, in the illustrated example, the blower suspension 7536SS1 provides structure, e.g., gusset portion, which allows flexibility and relative movement to isolate vibrations of the first blower 7200B1 and provide shock absorption.

The outlet chamber OC is relatively large to increase compliance and reduce outlet noise, e.g., attenuate outlet or forward conducted noise. Also, the outlet foam 7570SS1 (supported by the chassis plate 7510SS1) in the outlet chamber OC increases acoustic resistance and reduces outlet noise, e.g., see FIG. 30.

In an example, acoustic foam may be provided in one or more of the first, second, and third inlet muffler chambers IC1, IC2, IC3 and the outlet chamber OC, e.g., acoustic foam provided in each of the first, second, and third inlet muffler chambers IC1, IC2, IC3 and the outlet chamber OC. In one example, acoustic foam is provided in the first and third inlet muffler chambers IC1, IC3 and the outlet chamber OC, i.e., not in the second inlet muffler chamber IC2. However, it should be appreciated that alternative arrangements for acoustic foam are possible.

In the illustrated example, the chassis outlet 7320 may be communicated with an inlet of the water reservoir 6100 when the water reservoir 6100 is received in the reservoir dock 6050. In an alternative example, the chassis outlet 7320 may be directly communicated with the air circuit 4170.

FIGS. 57 to 59 are schematic views that schematically show the vertically offset chamber arrangement of the first configuration of the pneumatic block and the pneumatic air flow path of the first configuration of the pneumatic block. For example, as shown in FIG. 57, the first inlet muffler chamber IC1 extends in a first plane PL1, and the second inlet muffler chamber IC2, the third inlet muffler chamber IC3, and the outlet chamber OC extend in a second plane PL2 that is spaced vertically upward from the first plane PL1. FIG. 58 is a schematic view through the first plane PL1, and FIG. 59 is a schematic view through the second plane PL2.

FIGS. 57-59 include arrows showing an exemplary air flow path through the first, second, and third inlet chambers IC1, IC2, IC3 and the outlet chamber OC. As shown in FIG. 58, air enters the first inlet chamber IC1 in the first plane PL1, e.g., via the chassis inlet. As shown in in FIG. 57, air then passes from the first inlet chamber IC1 in the first plane PL1 to the second inlet chamber IC2 in the second plane PL2, e.g., via the flow tube 7515SS1. As shown in FIG. 59, air passes from the second inlet chamber IC2 in the second plane PL2 to the third inlet chamber IC3 in the second plane PL2, e.g., via the flow tube array 7554SS1. Air passes through the third inlet chamber IC3 in the second plane PL2 to the blower inlet 7210B1 of the first blower 7200B1 positioned in the second inlet chamber IC2 in the second plane PL2. Air flows through the first blower 7200B1 positioned in the second inlet chamber IC2 in the second plane PL2 and exits into the outlet chamber OC in the second plane PL2 as shown in FIG. 59. Pressurized air from the outlet chamber OC exits the pneumatic black via the chassis outlet.

As illustrated in FIGS. 57-59, the air flow path of the first configuration of the pneumatic block extends in different directions and in different planes from the chassis inlet to the chassis outlet. For example, the direction of air flow at the chassis inlet (see FIG. 58) extends transverse the direction of air flow at the chassis outlet (see FIG. 59). Also, as shown in FIG. 59, air flow through the second and third inlet chambers IC2, IC3 and the outlet chamber OC in the second plane PL2 extends in general J-shape, with air flow passing from the second inlet chamber IC2 to the third inlet chamber IC3 extending in the opposite direction from air flow passing from the third inlet chamber IC3, through the blower in the second inlet chamber IC2, and into the outlet chamber OC.

Second Blower Sub-Assembly

As shown in FIGS. 34-38, the second blower sub-assembly 7400SUB2 includes a second blower 7200B2 and a support structure 7500SS2 to support the second blower 7200B2 within the chassis assembly 7300.

In the illustrated example, the second blower 7200B2 includes a two-stage design structured and arranged for producing a flow, or a supply, of air at positive pressure, e.g., up to about 50 $cmH_2O$, e.g., in the range of about 4-50 $cmH_2O$.

The second blower 7200B2 includes a housing including an axial air inlet 7210B2 (blower inlet) and axial air outlet 7220B2 (blower outlet) between which are located two stages with two corresponding impellers, i.e., a first impeller positioned on one side of the motor and a second impeller positioned on the other side of the motor. However, other suitable impeller arrangements are possible. Each impeller is followed by a set of stator vanes structured and configured to direct the air flow to the next stage.

In the illustrated example, the second blower 7200B2 is mounted within a suspension 7250B2, e.g., comprising silicone, that forms a substantially sealed structure configured and arranged to sealingly separate air flow through an interior of the second blower 7200B2 from the pneumatic block cavity 7350. In addition, the suspension 7250B2 forms a shroud to isolate blower vibration, provide shock absorption, and provide a keying feature to ensure repeatable alignment of the second blower 7200B2 within the second blower sub-assembly 7400SUB2.

Further examples and details of the second blower 7200B2 are described in U.S. Pat. No. 8,636,479, which is incorporated herein by reference in its entirety.

The support structure 7500SS2 includes an outlet plate assembly 7530SS2 and a flow plate assembly 7550SS2.

The flow plate assembly 7550SS2 includes a base plate 7552SS2, a flow tube array 7554SS2, and a blower suspension 7556SS2 (inlet end suspension) supported within an opening provided to the base plate 7552SS2. In addition, a sealing lip or sealing flange 7558SS2 is provided along the edge or perimeter of the base plate 7552SS2.

In an example, the base plate 7552SS2 and the flow tube array 7554SS2 comprise a first part or base mold constructed of a relatively rigid material (e.g., thermoplastic polymer), and the blower suspension 7556SS2 and sealing lip 7558SS2 comprise a second part or overmold constructed of a relatively soft material (e.g., TPE or silicone) that is provided (e.g., by overmolding) to the first part.

The outlet plate assembly 7530SS2 includes a base plate 7532SS2 and a blower suspension 7536SS2 (outlet end suspension) supported within an opening provided to the base plate 7532SS2. In addition, a sealing lip or sealing flange 7538SS2 is provided along the edge or perimeter of the base plate 7532SS2.

In an example, the base plate 7532SS2 comprises a first part or base mold constructed of a relatively rigid material (e.g., thermoplastic polymer), and the blower suspension 7536SS2 and sealing lip 7538SS2 comprise a second part or overmold constructed of a relatively soft material (e.g., TPE or silicone) that is provided (e.g., by overmolding) to the first part.

The second blower 7200B2 is suspended by the support structure 7500SS2 between the flow plate assembly 7550SS2 and the outlet plate assembly 7530SS2. The flow plate assembly 7550SS2 and the outlet plate assembly 7530SS2 each include a blower suspension 7556SS2, 7536SS2 that cooperate to support the second blower 7200B2 within the chassis assembly 7300, provide seals for the air path, isolate vibrations of the second blower 7200B2, and provide shock resistance. The blower suspension 7556SS2, 7536SS2 may provide additional spring and damping to isolate vibrations and provide shock resistance. Specifically, the flow plate assembly 7550SS2 provides an inlet end suspension 7556SS2 to support the second blower 7200B2 adjacent the blower inlet 7210B2 and the outlet plate assembly 7530SS2 provides an outlet end suspension 7536SS2 to support the second blower 7200B2 adjacent the blower outlet 7220B2, i.e., a suspension is located at each end of the second blower 7200B2. Such arrangement also provides a keying feature to ensure repeatable alignment of the second blower 7200B2 within the second blower sub-assembly 7400SUB2.

In an example, as shown in FIGS. 37 and 38, the base plate 7552SS2 of the flow plate assembly 7550SS2 and/or the base plate 7532SS2 of the outlet plate assembly 7530SS2 may each include one or more flanges 7560SS2 along the perimeter of the blower suspension 7556SS2, 7536SS2, e.g., to act as a rigid stop or bump stop that limits the range of movement provided by the blower suspension 7556SS2, 7536SS2.

In an example, the second blower 7200B2 may be inserted into or otherwise assembled to the flow plate assembly 7550SS2, and then the second blower 7200B2 is inserted into or otherwise assembled to the outlet plate assembly 7530SS2. In an example, the second blower 7200B2 may be assembled to the flow plate assembly 7550SS2 using locational support tabs 7252B2 provided to the suspension 7250B2, e.g., pulling the locational support tabs 7252B2 through the blower suspension 7556SS2 to engage an inlet flange of the second blower 7200B2 with the blower suspension 7556SS2. In an example, the second blower 7200B2 may be assembled to the outlet plate assembly 7530SS2 using an outlet funnel 7254B2 provided to the suspension 7250B2, e.g., pulling the outlet funnel 7254B2 through the blower suspension 7536SS2 to engage the outlet funnel 7254B2 associated with the blower outlet of the second blower 7200B2 with the blower suspension 7536SS2.

Assembly of Second Blower Sub-Assembly to Chassis Assembly

The second blower sub-assembly 7400SUB2 is assembled to the chassis assembly 7300 to form a second configuration of the pneumatic block 7100, e.g., configured for bi-level therapy.

FIGS. 39-41 show assembly of the second blower sub-assembly 7400SUB2 to the chassis assembly 7300. The second blower sub-assembly 7400SUB2 is first lowered into the bottom chassis 7300B as shown in FIG. 39. As illustrated, the base plate 7552SS2 of the flow plate assembly

7550SS2 and the base plate 7532SS2 of the outlet plate assembly 7530SS2 are arranged to engage within respective internal locational grooves 7360B1, 7360B2 in the bottom chassis 7300B to locate and support the second blower sub-assembly 7400SUB2 within the bottom chassis 7300B. In addition, the internal ribs 7365 provided to the bottom chassis 7300B may further support the suspension 7250B2 and second blower 7200B2 therewithin within the bottom chassis 7300B.

In an example, acoustic foam, i.e., inlet foam, may be placed into the pneumatic block portion of the bottom chassis 7300B to increase acoustic resistance and reduce noise.

As shown in FIG. 40, the top chassis 7300T is then lowered onto the bottom chassis 7300B, ensuring that the base plate 7552SS2 of the flow plate assembly 7550SS2 and the base plate 7532SS2 of the outlet plate assembly 7530SS2 engage within respective internal locational grooves 7360T1, 7360T2 in the top chassis 7300T to locate and support the second blower sub-assembly 7400SUB2 within the top chassis 7300T. The top and bottom chassis 7300T, 7300B may be retained to one another in any suitable manner, e.g., via mechanical fasteners (e.g., screws) and/or retaining clips.

Finally, as shown in FIG. 41, the PCBA 7600 is attached to an upper wall of the top chassis 7300T, e.g., via mechanical fasteners (e.g., screws), outside the pneumatic block cavity 7350. As described above, the PCBA 7600 includes a flow sensor and a pressure sensor arranged to communicate with the pneumatic block cavity 7350.

The electrical connection between the PCBA 7600 and the second blower 7200B2 may be made via a flexible circuit board (FCB), flexible printed circuits (FPC) and/or flexible flat cables (FFC) extending from the second blower 7200B2 within the pneumatic block cavity 7350 up to the PCBA 7600. FIGS. 34-38 show an example a flexible flat cable 7260B2 extending from the second blower 7200B2.

Chamber Arrangement and Pneumatic Air Flow Path Provided By Second Blower Sub-Assembly When assembled, the second blower sub-assembly 7400SUB2 and the chassis assembly 7300 cooperate to provide a second configuration of the pneumatic block 7100 including two inlet muffler chambers IC1, IC2 and an outlet chamber OC along the air flow path, e.g. see FIG. 36.

In the illustrated example, as shown in FIGS. 42-48, the bottom chassis 7300B, the top chassis 7300T, the base plate 7552SS2 of the flow plate assembly 7550SS2, and the base plate 7532SS2 of the outlet plate assembly 7530SS2 cooperate to form a first inlet muffler chamber IC1; the bottom chassis 7300B, the top chassis 7300T, and the base plate 7552SS2 of the flow plate assembly 7550SS2 cooperate to form a second inlet muffler chamber IC2; and the top chassis 7300T, the bottom chassis 7300B, and the base plate 7532SS2 of the outlet plate assembly 7530SS2 cooperate to form an outlet chamber OC.

In the illustrated example, each of the chambers IC1, IC2, OC is sealed. The sealing is created via the overmolded sealing lips 7538SS2, 7558SS2 (e.g., silicone) along the perimeter of the base plates 7532SS2, 7552SS2, with controlled compression against the top and bottom chassis 7300T, 7300B.

In the illustrated example, e.g., see FIG. 46, the bottom of the RPT device 7000 includes a bottom surface defining a bottom plane BP that is substantially horizontal when the RPT device 7000 is in a working orientation. As illustrated, in the second configuration of the pneumatic block 7100, the second blower 7200B2 is arranged such that an axis AX2 of the second blower 7200B2 (extending through the air inlet 7210B2 and the air outlet 7220B2) is parallel to the bottom plane BP. That is, the axis AX2 of the second blower 7200B2 extends in a generally horizontal plane when the RPT device 7000 is in a working orientation.

In the illustrated example, the pneumatic air flow path of the second configuration of the pneumatic block 7100 includes a tortuous path extending from the chassis inlet 7310 to the chassis outlet 7320. In an example, the air flow path extends generally in one plane, e.g., the first inlet muffler chamber IC1, the second inlet muffler chamber IC2, and the outlet chamber OC extend in one plane, e.g., see FIG. 46.

As illustrated, the air flow path of the second configuration of the pneumatic block 7100 is structured and arranged such that air enters the chassis assembly 7300 via the inlet openings 7340 (e.g., see FIG. 25) and into the recessed chamber 7342, passes from the recessed chamber 7342 through the long inlet tube 7345, and into the first inlet muffler chamber IC1 as shown in FIGS. 42 and 43. The long inlet tube 7345 is relatively long to allow for noise reduction (due to high inertance) as air passes from the inlet openings 7340 to the first inlet muffler chamber IC1. In an example, inlet foam may be provided in the first inlet muffler chamber IC1 to increase acoustic resistance and reduce inlet noise.

Air passes from the first inlet muffler chamber IC1 to the second inlet muffler chamber IC2 via the flow tube array 7554SS2 provided by the flow plate assembly 7550SS2 as shown in FIG. 44. The second inlet muffler chamber IC2 receives air from the flow tube array 7554SS2 and delivers the air to the blower inlet 7210B2 of the second blower 7200B2. As illustrated, the second blower 7200B2 is supported in the first inlet muffler chamber IC1, and receives air at the blower inlet 7210B2 from the second inlet muffler chamber IC2. In an example, inlet foam may be provided in the second inlet muffler chamber IC2 to increase acoustic resistance and reduce inlet noise.

The blower suspension 7556SS2 of the flow plate assembly 7550SS2 may be secured to the second blower 7200B2 in any suitable manner, e.g., wrap around an inlet flange provided to the blower inlet 7210B2 of the second blower 7200B2. The blower suspension 7556SS2 provides a seal along the blower inlet 7210B2, thereby sealing the blower inlet 7210B2 from the first inlet muffler chamber IC1 and providing an air path for air entering the blower inlet 7210B2 from the second inlet muffler chamber IC2. Also, in the illustrated example, the blower suspension 7556SS2 provides structure, e.g., gusset portion, which allows flexibility and relative movement to isolate vibrations of the second blower 7200B2 and provide shock absorption.

The flow tube array 7554SS2 includes a plurality of flow tubes 7555SS2 structured and arranged to extend from the base plate 7552SS2 into the first inlet muffler chamber IC1, e.g., flow tubes 7555SS2 extend generally perpendicular with respect to the base plate 7552SS2. Thus, the air flow path extends from first inlet muffler chamber IC1, through the flow tube array 7554SS2, and into the second inlet muffler chamber IC2. The flow tubes 7555SS2 are structured and arranged to allow laminar flow, provide a defined pressure drop, and provide sufficient length to reduce noise.

In the illustrated example, the flow tube array 7554SS2 includes twelve, spaced-apart flow tubes 7555SS2, e.g., generally arranged in four rows of three tubes. However, it should be appreciated that other suitable number of tubes 7555SS2 are possible (e.g., one or more flow tubes, e.g., 5-15 flow tubes) and the tubes 7555SS2 may be arranged in other suitable manners (e.g., aligned in rows and/or columns, circular arrangement).

In the illustrated example, each of the plurality of flow tubes 7555SS2 includes a circular cross-sectional shape, however it should be appreciated that each of the tubes 7555SS2 may include other cross-sectional shapes, e.g., circular shape or noncircular shape. Also, each of the plurality of flow tubes 7555SS2 may include any suitable length, diameter, wall thickness, and cross-sectional area, e.g., depending on the desired noise characteristic. Further, the plurality of flow tubes 7555SS2 may comprise flow tubes of equal lengths and/or unequal lengths.

The first and second inlet muffler chambers IC1, IC2 cooperate to increase compliance and reduce inlet noise along the air flow path to the blower inlet 7210B2 of the second blower 7200B2.

Air flows through the second blower 7200B2 such that a flow of air at positive pressure is provided at the blower outlet 7220B2 of the second blower 7200B2. The outlet chamber OC receives pressurized air exiting the blower outlet 7220B2 of the second blower 7200B2 as shown in FIG. 45. The pressured air from the outlet chamber OC exits the pneumatic block via the chassis outlet 7320. In an example, the outlet chamber OC of the second configuration of the pneumatic block 7100 may be at a positive pressure of up to about to 50 $cmH_2O$.

The blower suspension 7536SS2 of the outlet plate assembly 7530SS2 may be secured to the second blower 7200B2 in any suitable manner, e.g., wrap around the outlet funnel 7254B2 of the suspension 7250B2 associated with the blower outlet 7220B2 of the second blower 7200B2. The blower suspension 7536SS2 provides a seal along the blower outlet 7220B2, thereby sealing the blower outlet 7220B2 from the first inlet muffler chamber IC1 and providing an air path for air exiting the blower outlet 7220B2 into the outlet chamber OC. Also, in the illustrated example, the blower suspension 7536SS2 provides structure, e.g., gusset portion, which allows flexibility and relative movement to isolate vibrations of the second blower 7200B2 and provide shock absorption.

The outlet chamber OC is relatively large to increase compliance and reduce outlet noise. Also, acoustic foam, i.e., outlet foam, may be provided in the outlet chamber OC to increase acoustic resistance and reduce outlet noise.

In an example, acoustic foam may be provided in one or more of the first and second inlet muffler chambers IC1, IC2 and the outlet chamber OC, e.g., acoustic foam provided in each of the first and second inlet muffler chambers IC1, IC2 and the outlet chamber OC. It should be appreciated that alternative arrangements for acoustic foam are possible.

In the illustrated example, the chassis outlet 7320 may be communicated with an inlet of the water reservoir 6100 when the water reservoir 6100 is received in the reservoir dock 6050. In an alternative example, the chassis outlet 7320 may be directly communicated with the air circuit 4170.

FIGS. 60 to 61 are schematic views that schematically show the chamber arrangement of the second configuration of the pneumatic block and the pneumatic air flow path of the second configuration of the pneumatic block. For example, as shown in FIG. 60, the first inlet muffler chamber IC1, the second inlet muffler chamber IC2, and the outlet chamber OC all extend in one plane PL1. FIG. 61 is a schematic view through the plane PL1 of FIG. 60.

FIG. 61 includes arrows showing an exemplary air flow path through the first and second inlet chambers IC1, IC2 and the outlet chamber OC. As illustrated, air enters the first inlet chamber IC1, e.g., via the chassis inlet. Air then passes from the first inlet chamber IC1 to the second inlet chamber IC2, e.g., via the flow tube array 7554SS2. Air passes through the second inlet chamber IC2 to the blower inlet 7210B2 of the second blower 7200B2 positioned in the first inlet chamber IC1. Air flows through the second blower 7200B2 positioned in the first inlet chamber IC1 and exits into the outlet chamber OC. Pressurized air from the outlet chamber OC exits the pneumatic black via the chassis outlet.

As illustrated in FIG. 61, the air flow path of the second configuration of the pneumatic block extends in different directions from the chassis inlet to the chassis outlet. For example, the direction of air flow at the chassis inlet extends transverse the direction of air flow at the chassis outlet. Also, as shown in FIG. 61, air flow through the first and second inlet chambers IC1, IC2 and the outlet chamber OC extends in general J-shape, with air flow passing from the first inlet chamber IC1 to the second inlet chamber IC2 extending in the opposite direction from air flow passing from the second inlet chamber IC1, through the blower in the first inlet chamber IC1, and into the outlet chamber OC.

Flow and Pressure Sensors

As noted above, the PCBA 7600 includes a flow sensor 7610 and a pressure sensor 7620 to monitor and control air flow and pressure in the pneumatic block 7100. The upper wall of the top chassis 7300T includes openings or ports P1, P2, P3 (e.g., see FIGS. 9, 15, and 50) that allow the sensors 7610, 7620 to communicate with the pneumatic block cavity 7350.

In the illustrated example, the flow sensor 7610 includes a pair of sensors 7610A, 7610B communicated with respective flow sensor ports P1, P2 in the top chassis 7300T as shown in FIG. 49. The flow sensors ports P1, P2 are arranged on opposite sides of the flow plate assembly 7550SS1, 7550SS2, i.e., on opposite sides of the internal locational groove 7360T1 in the top chassis 7300T adapted to support the flow plate assembly 7550SS1, 7550SS2, e.g., see FIG. 50. The pair of sensors 7610A, 7610B are sealed in respective flow sensor ports P1, P2, e.g., via the overmold 7302T (internal skin) provided to the interior surface of the top chassis 7300T.

For example, as shown in FIGS. 49 and 52, the overmold 7302T of the top chassis 7300T provides a first sealing portion 7305SP1 along flow sensor port P1 and a second sealing portion 7305SP2 along flow sensor port P2. As illustrated, each of the first and second sealing portions 7305SP1, 7305SP2 provides a tubular sealing surface or interface 7306 adapted to sealingly engage along the exterior surface of respective flow sensors 7610A, 7610B. The outer end of each of the first and second sealing portions 7305SP1, 7305SP2 includes a chamfer edge 7307 to facilitate engagement of each of the first and second sealing portions 7305SP1, 7305SP2 with respective flow sensors 7610A, 7610B, i.e., chamfer edge 7307 guides respective flow sensors 7610A, 7610B into engagement with respective tubular sealing surfaces 7306.

However, the first and second sealing portions 7305SP1, 7305SP2 may have alternative geometries configured for sealing with respective flow sensors 7610A, 7610B. For example, in an alternative example as shown in FIG. 53, each of the first and second sealing portions 7305SP1, 7305SP2 provides an inner tubular section 7312 and an outer ring section 7314 that protrudes radially inwardly relative to the inner tubular section 7312. The outer end of each of the first and second sealing portions 7305SP1, 7305SP2 includes an annular groove 7316 which provides a flexing space for the outer ring section 7314. The flexing space provided by annular groove 7316 is configured and arranged to allow the outer ring section 7314 to resiliently deflect radially outwardly to facilitate engagement of the outer ring section 7314 of each of the first and second sealing portions 7305SP1, 7305SP2 with respective flow sensors 7610A, 7610B. Moreover, such resilient deflection of the outer ring section 7314 provides a bias for sealing of the outer ring section 7314 with respective flow sensors 7610A, 7610B.

In the first configuration of the pneumatic block 7100, the flow sensor 7610 is communicated with respective flow sensor ports P1, P2 to measure the drop in pressure between the second and third chambers IC2, IC3 in the pneumatic block, i.e., bypass flow proportional to the differential pressure between the second and third chambers IC2, IC3. That is, one of the pair of sensors 7610B of the flow sensor is arranged to measure a first pressure in the second chamber IC2 and the other of the pair of sensors 7610A of the flow sensor is arranged to measure a second pressure in the third chamber IC3 to determine an air flow rate.

In the second configuration of the pneumatic block, the flow sensor 7610 is communicated with respective flow sensor ports P1, P2 to measure the drop in pressure between the first and second chambers IC1, IC2 in the pneumatic block, i.e., bypass flow proportional to the differential pressure between the first and second chambers IC1, IC2. That is, one of the pair of sensors 7610B of the flow sensor is arranged to measure a first pressure in the first chamber IC1 and the other of the pair of sensors 7610A of the flow sensor is arranged to measure a second pressure in the second chamber IC2 to determine an air flow rate.

In the illustrated example, the pressure sensor 7620 is communicated with a pressure sensor port P3 in the top chassis 7300T as shown in FIGS. 50 and 51. The pressure sensor port P3 is arranged on the outlet chamber side formed by the outlet plate assembly 7530SS1, 7530SS2, i.e., on a side of the internal locational groove 7360T2 in the top chassis 7300T adapted to support the outlet plate assembly 7530SS1, 7530SS2, e.g., see FIG. 50. The pressure sensor 7620 is sealed in the pressure sensor port P3, e.g., via the overmold 7302T (internal skin) provided to the interior surface of the top chassis 7300T.

For example, as shown in FIG. 51, the overmold 7302T of the top chassis 7300T provides a sealing portion 7308 along pressure sensor port P3. As illustrated, the sealing portion 7308 provides a tubular sealing surface or interface 7309 adapted to sealingly engage along the exterior surface of the pressure sensor 7620.

In both the first and second configuration of the pneumatic block, the pressure sensor 7620 is arranged to measure the pressure in the outlet chamber OC in the pneumatic block, e.g., measures static pressure perpendicular to the air flow direction.

In an example, a secondary pressure sensor may be provided, e.g., to provide a secondary measure of the pressure in the outlet chamber OC. In an example, if either the primary pressure sensor 7620 or the secondary pressure sensor reads unusually, the controller will initiate a shutdown of the RPT device. The secondary pressure sensor may act as a backup so the RPT device does not rely on a single sensor or single fault condition, e.g., to enhance safety.

FIGS. 54 to 56 show a pressure sensor seal 7800 structured and arranged to sealingly engage both a primary pressure sensor 7620 and a secondary pressure sensor 7621 provided to the PCBA 7600. In this example, the pressure sensor seal 7800 is formed as a separate and distinct structure (separately molded component, e.g., of silicone) from the top chassis 7300T, and then connected thereto.

As shown in FIG. 55, the pressure sensor seal 7800 includes a base portion 7810, first and second sealing portions 7820SP1, 7820SP2 supported by the base portion 7810, and central connecting portion 7830 to facilitate alignment and releasable connection of the pressure sensor seal 7800 to the top chassis 7300T.

As illustrated, each of the first and second sealing portions 7820SP1, 7820SP2 includes a port engaging side 7822 and a sensor engaging side 7824. Each port engaging side 7822 provides a tubular sealing surface or interface 7823 adapted to sealingly engage along the exterior surface of a respective spigot 7325 for pressure sensor ports P3, P4 formed in the base mold 7301T (e.g., thermoplastic polymer (e.g., PC, ABS)) of the top chassis 7300T.

Each sensor engaging side 7824 includes a concertina-type interface 7825 with one or more folds to facilitate engagement with a respective pressure sensor 7620, 7621. In use, the concertina-type interface 7825 is configured and arranged to compress axially and/or flex laterally in order to align and sealing engage along the exterior surface of a respective pressure sensor 7620, 7621. This flexibility provided by the concertina-type interface 7825 accommodates any manufacturing tolerances of the top chassis 7300T and the PCBA 7600. For example, the concertina-type interface 7825 can accommodate any misalignment between the sensors 7620, 7621 and respective spigots 7325, e.g., so the sensors 7620, 7621 are not forced laterally which can potentially alter readings or damage the PCBA 7600.

In the illustrated example, an inwardly-extending fold of the concertina-type interface 7825 provides a sealing surface 7826 adapted to sealingly engage a respective pressure sensor 7620, 7621.

In the illustrated example, the central connecting portion 7830 provides a tubular surface or interface 7832 adapted to engage along the exterior surface of a mounting post 7327 formed in the base mold 7301T of the top chassis 7300T. Such engagement facilitates alignment of the first and second sealing portions 7820SP1, 7820SP2 with respective spigots 7325 of the top chassis 7300T and releasably secures, e.g., via frictional engagement, the pressure sensor seal 7800 to the top chassis 7300T.

In the illustrated example, the base portion 7810 provides thickened wall portions along at least a portion of the perimeter of the pressure sensor seal 7800 adapted to be supported within a recess 7329 on the outer side of the top chassis 7300T.

FIG. 56 shows the pressure sensor seal 7800 connected to the top chassis 7300T and sealingly engaged with the spigots 7325 and pressure sensors 7620, 7621 thereby pneumatically connecting the pressure sensors 7620, 7621 with the outlet chamber OC in the pneumatic block. As illustrated, an intermediate portion of each sealing portion 7820SP1, 7820SP2 may form at least part of a passageway between the respective pressure sensor 7620, 7621 and the respective spigot 7325 for pressure sensor ports P3, P4.

In an alternative example, one or more portions of the pressure sensor seal 7800 may be integrated with the overmold 7302T of the top chassis 7300T.

5.6.3 Humidifier Components 5.6.3.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.3.2 Conductive Portion

According to one arrangement, the reservoir 5110 comprises a conductive portion configured to allow efficient transfer of heat from the heating element to the volume of liquid in the reservoir 5110. In one form, the conductive portion may be arranged as a plate, although other shapes may also be suitable. All or a part of the conductive portion may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.3.3 Humidifier Reservoir Dock

In one form, the humidifier 5000 may comprise a humidifier reservoir dock configured to receive the humidifier reservoir 5110. In some arrangements, the humidifier reservoir dock may comprise a locking feature such as a locking lever configured to retain the reservoir 5110 in the humidifier reservoir dock.

5.6.3.4 Water Level Indicator

The humidifier reservoir 5110 may comprise a water level. In some forms, the water level indicator 5150 may provide one or more indications to a user such as the patient 1000 or a care giver regarding a quantity of the volume of water in the humidifier reservoir 5110. The one or more indications provided by the water level indicator may include an indication of a maximum, predetermined volume of water, any portions thereof, such as 25%, 50% or 75% or volumes such as 200 ml, 300 ml or 400 ml.

5.6.3.5 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5G. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.6.3.5.1 Pressure Transducer

One or more pressure transducers 5212 may be provided to the humidifier 5000 in addition to, or instead of, a pressure sensor 4272 provided in the RPT device 4000.

5.6.3.5.2 Flow Rate Transducer

One or more flow rate transducers 5214 may be provided to the humidifier 5000 in addition to, or instead of, a flow rate sensor 4274 provided in the RPT device 4000.

5.6.3.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet. In some forms, the humidifier 5000 may further comprise a temperature sensor 5216 to detect the temperature of the ambient air.

5.6.3.5.4 Humidity Transducer

In one form, the humidifier 5000 may comprise one or more humidity sensors 5218 to detect a humidity of a gas, such as the ambient air. The humidity sensor 5218 may be placed towards the humidifier outlet in some forms to measure a humidity of the gas delivered from the humidifier 5000. The humidity sensor may be an absolute humidity sensor or a relative humidity sensor.

5.6.3.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base where heat may be provided to the humidifier reservoir 5110 primarily by conduction.

5.6.3.7 Humidifier Controller

According to one arrangement of the present technology, a humidifier 5000 may comprise a humidifier controller 5250 as shown in FIG. 5G. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5G, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.7 Breathing Waveforms

FIG. 4 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak−0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.8.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.5 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.8.5.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.5.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.5.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix. A typical human right ear comprises a helix, which is a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule, or alternatively by a left-hand rule.

Osculating plane: The plane containing the unit tangent vector and the unit principal normal vector.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path).

With reference to the right-hand rule, a space curve turning towards the direction of the right-hand binormal may be considered as having a right-hand positive torsion. A space curve turning away from the direction of the right-hand binormal may be considered as having a right-hand negative torsion (e.g. a left-hand helix).

Equivalently, and with reference to a left-hand rule, a space curve turning towards the direction of the left-hand binormal may be considered as having a left-hand positive torsion (e.g. a left-hand helix). Hence left-hand positive is equivalent to right-hand negative.

5.8.5.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3G, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. In a yet another example, a conduit may comprise a one-dimension hole (e.g. at its entrance or at its exit), and a two-dimension hole bounded by the inside surface of the conduit. See also the two dimensional hole through the structure shown in FIG. 3I, bounded by a surface as shown.

5.9 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.10 REFERENCE SIGNS LIST

| Feature Item | Number |
|---|---|
| patient | 1000 |
| bed partner | 1100 |
| patient interface | 3000 |
| seal - forming structure | 3100 |
| plenum chamber | 3200 |
| positioning and stabilising structure | 3300 |
| vent | 3400 |
| connection port | 3600 |
| forehead support | 3700 |
| RPT device | 4000 |
| main panel | 4010 |
| front panel | 4012 |
| side panel | 4014 |
| chassis | 4016 |
| pneumatic block | 4020 |
| air filter | 4110 |
| inlet air filter | 4112 |
| outlet air filter | 4114 |
| mufflers | 4120 |
| inlet muffler | 4122 |
| outlet muffler | 4124 |
| pressure generator | 4140 |
| blower | 4142 |
| motor | 4144 |
| anti - spill back valve | 4160 |
| air circuit | 4170 |
| air circuit | 4171 |
| supplemental oxygen | 4180 |
| electrical components | 4200 |
| PCBA | 4202 |
| power supply | 4210 |
| input device | 4220 |
| central controller | 4230 |
| clock | 4232 |
| therapy device controller | 4240 |
| protection circuits | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| algorithms | 4300 |
| pre - processing module | 4310 |
| pressure compensation algorithm | 4312 |
| vent flow rate estimation algorithm | 4314 |
| leak flow rate estimation algorithm | 4316 |
| respiratory flow rate estimation algorithm | 4318 |
| therapy engine module | 4320 |
| phase determination algorithm | 4321 |
| waveform determination algorithm | 4322 |
| ventilation determination algorithm | 4323 |
| inspiratory flow limitation determination algorithm | 4324 |
| apnea/hypopnea determination algorithm | 4325 |
| snore determination algorithm | 4326 |
| airway patency determination algorithm | 4327 |
| therapy parameter determination algorithm | 4329 |
| therapy control module | 4330 |
| methods | 4340 |
| humidifier | 5000 |
| humidifier reservoir | 5110 |
| humidifier transducer | 5210 |

-continued

| Feature Item | Number |
|---|---|
| pressure transducer | 5212 |
| flow rate transducer | 5214 |
| temperature transducer | 5216 |
| humidity sensor | 5218 |
| heating element | 5240 |
| humidifier controller | 5250 |
| central humidifier controller | 5251 |
| heating element controller | 5252 |
| air circuit controller | 5254 |
| humidifier | 6000 |
| reservoir dock | 6050 |
| dock portion | 6050T |
| dock portion | 6050B |
| guiding structure | 6060 |
| water reservoir | 6100 |
| RPT device | 7000 |
| pneumatic block | 7100 |
| first blower | 7200B1 |
| second blower | 7200B2 |
| blower inlet | 7210B1 |
| blower inlet | 7210B2 |
| blower outlet | 7220B1 |
| blower outlet | 7220B2 |
| suspension | 7250B2 |
| support tabs | 7252B2 |
| funnel | 7254B2 |
| flexible flat cable | 7260B2 |
| chassis assembly | 7300 |
| top chassis | 7300T |
| bottom chassis | 7300B |
| base mold | 7301T |
| base mold | 7301B |
| overmold | 7302T |
| overmold | 7302B |
| first sealing portion | 7305SP1 |
| second sealing portion | 7305SP2 |
| sealing surface | 7306 |
| chamfer edge | 7307 |
| sealing portion | 7308 |
| sealing surface | 7309 |
| chassis inlet | 7310 |
| inner tubular section | 7312 |
| outer ring section | 7314 |
| annular groove | 7316 |
| chassis outlet | 7320 |
| spigot | 7325 |
| mounting post | 7327 |
| recess | 7329 |
| opening | 7330 |
| inlet openings | 7340 |
| recessed chamber | 7342 |
| inlet tube | 7345 |
| pneumatic block cavity | 7350 |
| block portion | 7350T |
| block portion | 7350B |
| locational groove | 7360T1 |
| locational groove | 7360T2 |
| locational groove | 7360B1 |
| locational groove | 7360B2 |
| internal ribs | 7365 |
| first blower sub-assembly | 7400SUB1 |
| second blower sub-assembly | 7400SUB2 |
| support structure | 7500SS1 |
| support structure | 7500SS2 |
| chassis plate | 7510SS1 |
| locational groove | 7512SS1 |
| arm | 7513SS1 |
| flow tube | 7515SS1 |
| sealing lip | 7518SS1 |
| support plate | 7519SS1 |
| outlet plate assembly | 7530SS1 |
| outlet plate assembly | 7530SS2 |
| base plate | 7532SS1 |
| base plate | 7532SS2 |
| blower suspension | 7536SS1 |
| blower suspension | 7536SS2 |
| sealing lip | 7538SS1 |

-continued

| Feature Item | Number |
| --- | --- |
| sealing lip | 7538SS2 |
| flow plate assembly | 7550SS1 |
| flow plate assembly | 7550SS2 |
| base plate | 7552SS1 |
| base plate | 7552SS2 |
| flow tube array | 7554SS1 |
| flow tube array | 7554SS2 |
| flow tubes | 7555SS1 |
| flow tubes | 7555SS2 |
| blower suspension | 7556SS1 |
| blower suspension | 7556SS2 |
| sealing lip | 7558SS1 |
| sealing lip | 7558SS2 |
| flanges | 7560SS1 |
| flanges | 7560SS2 |
| outlet foam | 7570SS1 |
| PCBA | 7600 |
| flow sensor | 7610 |
| sensor | 7610A |
| sensor | 7610B |
| pressure sensor | 7620 |
| pressure sensor | 7621 |
| inlet foam | 7700 |
| pressure sensor seal | 7800 |
| base portion | 7810 |
| first sealing portion | 7820SP1 |
| second sealing portion | 7820SP2 |
| port engaging side | 7822 |
| sealing surface | 7823 |
| sensor engaging side | 7824 |
| concertina-type interface | 7825 |
| sealing surface | 7826 |
| central connecting portion | 7830 |
| tubular surface | 7832 |
| external housing | 8002 |

The invention claimed is:

1. Apparatus for providing air at positive pressure for respiratory therapy to a patient, the apparatus comprising:

a pneumatic block comprising:

a blower sub-assembly including a blower configured to produce a flow of air at a therapeutic pressure; and a chassis assembly forming a pneumatic block cavity configured to locate and support the blower sub-assembly, the chassis assembly including a chassis inlet and a chassis outlet, wherein the pneumatic block forms an air flow path extending from the chassis inlet to a blower inlet of the blower and from a blower outlet of the blower to the chassis outlet, wherein the pneumatic block forms a chamber arrangement including a plurality of chambers along the air flow path, wherein the blower sub-assembly includes a support structure configured to support the blower within the chassis assembly, wherein the support structure is configured and arranged to sealingly separate the air flow path into the plurality of chambers of the chamber arrangement, wherein the plurality of chambers of the chamber arrangement includes a first inlet muffler chamber, a second inlet muffler chamber, a third inlet muffler chamber, and an outlet chamber along the air flow path, wherein the plurality of chambers of the chamber arrangement extend in more than one plane, and wherein the first inlet muffler chamber extends in a first plane, and the second inlet muffler chamber, the third inlet muffler chamber, and the outlet chamber extend in a second plane that is vertically spaced upward from the first plane.

2. Apparatus according to claim 1, wherein air flow through the second inlet muffler chamber, the third inlet muffler chamber, and the outlet chamber in the second plane extends in a general J-shape.

3. Apparatus according to claim 1, wherein air flow passing from the second inlet muffler chamber to the third inlet muffler chamber extends in an opposite direction from air flow passing from the third inlet muffler chamber, through the blower, and into the outlet chamber.

4. Apparatus according to claim 1, wherein the first inlet muffler chamber, the second inlet muffler chamber, and the third inlet muffler chamber are positioned upstream of the blower inlet of the blower, and the outlet chamber is positioned downstream of the blower outlet of the blower.

5. Apparatus according to claim 1, wherein the first inlet muffler chamber receives air from the chassis inlet, and wherein the blower is provided in the second inlet muffler chamber and receives air at the blower inlet of the blower from the third inlet muffler chamber.

6. Apparatus according to claim 1, wherein the support structure includes a flow tube array including a plurality of flow tubes configured to allow air to pass from the second inlet muffler chamber to the third inlet muffler chamber.

7. Apparatus according to claim 1, wherein the support structure includes a blower suspension configured to support the blower and isolate vibrations.

8. Apparatus according to claim 1, wherein the blower is configured for CPAP or APAP therapy.

9. Apparatus according to claim 1, wherein the chassis assembly includes a reservoir dock configured to receive a water reservoir.

10. Apparatus according to claim 1, further comprising a printed circuit board assembly supported by the pneumatic block outside the air flow path.

11. Apparatus according to claim 10, wherein the chassis assembly includes one or more ports configured to allow one or more sensors provided to the printed circuit board assembly to communicate with the air flow path.

12. Apparatus according to claim 1, further comprising acoustic foam provided within one or more of the plurality of chambers of the chamber arrangement.

13. Apparatus according to claim 1, wherein the chassis assembly includes a top chassis and a bottom chassis forming the pneumatic block cavity configured to receive the blower sub-assembly.

14. Apparatus according to claim 13, wherein each of the top chassis and the bottom chassis includes an elastomeric overmold along an interior surface thereof to provide a seal for the pneumatic block cavity.

15. Apparatus according to claim 1, wherein a direction of air flow at the chassis inlet extends transverse to a direction of air flow at the chassis outlet.

* * * * *